US010046005B2

(12) United States Patent
Mousa

(10) Patent No.: US 10,046,005 B2
(45) Date of Patent: Aug. 14, 2018

(54) COMPOSITION AND METHOD OF USE FOR COMBINATIONS OF ANTI-VIRAL PROTEASE, POLYMERASE INHIBITORS AND NATURAL BIOACTIVE COMPOUNDS IN THE TREATMENT OF HEPATITIS C INFECTION

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 36 days.

(21) Appl. No.: 15/234,291

(22) Filed: Aug. 11, 2016

(65) Prior Publication Data

US 2016/0346308 A1 Dec. 1, 2016

Related U.S. Application Data

(63) Continuation-in-part of application No. 14/614,496, filed on Feb. 5, 2015, now Pat. No. 9,597,351.

(60) Provisional application No. 61/936,944, filed on Feb. 7, 2014, provisional application No. 62/237,615, filed on Oct. 6, 2015.

(51) Int. Cl.
| | |
|---|---|
| *A61K 31/353* | (2006.01) |
| *A61K 31/7032* | (2006.01) |
| *A61K 31/7072* | (2006.01) |
| *A61K 31/726* | (2006.01) |
| *A61K 45/06* | (2006.01) |
| *A61K 47/48* | (2006.01) |
| *A61K 9/00* | (2006.01) |
| *A61K 9/16* | (2006.01) |
| *A61K 9/20* | (2006.01) |
| *A61K 31/7056* | (2006.01) |
| *A61K 31/198* | (2006.01) |
| *A61K 31/728* | (2006.01) |
| *A61K 31/734* | (2006.01) |
| *A61K 31/737* | (2006.01) |
| *A61K 47/69* | (2017.01) |

(52) U.S. Cl.
CPC ........ *A61K 31/7056* (2013.01); *A61K 9/0053* (2013.01); *A61K 9/167* (2013.01); *A61K 9/1635* (2013.01); *A61K 9/1647* (2013.01); *A61K 9/1652* (2013.01); *A61K 9/20* (2013.01); *A61K 31/198* (2013.01); *A61K 31/353* (2013.01); *A61K 31/7072* (2013.01); *A61K 31/728* (2013.01); *A61K 31/734* (2013.01); *A61K 31/737* (2013.01); *A61K 45/06* (2013.01); *A61K 47/6937* (2017.08)

(58) Field of Classification Search
None
See application file for complete search history.

(56) References Cited

U.S. PATENT DOCUMENTS

| | | | |
|---|---|---|---|
| 2004/0147549 A1* | 7/2004 | Tyms | A61K 31/00 514/306 |
| 2014/0017329 A1 | 1/2014 | Mousa | |
| 2015/0224134 A1 | 8/2015 | Mousa | |

OTHER PUBLICATIONS

Gane, N Engl J Med 368;1, Jan. 3, 2013.*
Dihman, Journal of Clinical and Experimental Hepatology, Dec. 2011, vol. 1, No. 3, 159-160.*
Cutler, HCV and the Body's Most Important Antioxidant, www.hepatitiscentral.com/news/hcv_and_the_bod/, Jul. 13, 2007.*
Zaman, Taribavirin vs. Ribavirin for Chronic Hepatitis C Virus Infection, Gastroenterology, Dec. 17, 2010.*
PCT ISR WO; PCT/US2016/014795; dated Mar. 31, 2016, 8 pages.
Belousova, Vet al. Recent Advances and Future Directions in the Management of Hepatitis C Infections. Pharmacology & Therapeutics. 2015 (available online Sep. 2014). vol. 145, p. 96, first column, third-fourth paragraphs; p. 99, second column, fifth-sixth paragraphs, 11 pages.
Ozgur, E et al. Mobile Phone Radiation-Induced Free Radical Damage in the liver is Inhibited by the Antioxidants N-Acetyl Cysteine and Epigallocatechin-Gallate. International Journal of Radiation Biology. Nov. 2010. vol. 86, No. 11; p. 936, first column, second-third paragraphs; p. 942; second column, third paragraph, 12 pages.
Sudha, T et al. Suppression of Pancreatic Cancer by Sulfated Non-Anticoagulant Low Molecular Weight Heparin. Cancer Letters. Aug. 1, 2014 vol. 350, No. O; p. 2, third-fourth paragraphs; p. 8, fifth paragraph, 20 pages.
Xu, X et al. Heparin: An Intervenor in Cell Communications. Journal of Cellular and Molecular Medicine. 2010. vol. 14, No. 1-2; p. 176, second column, second paragraph, 6 pages.
Wang, Wet al. Galactosylated Solid Lipid Nanoparticles with Cucurbitacin B Improves the liver Targetability. Drug Delivery. 2010. vol. 17, No. 3; abstract, 2 pages.
Office Action (dated May 17, 2016) for U.S. Appl. No. 14/614,496, filed Feb. 5, 2015.
Amendment (dated Aug. 25, 2016) for U.S. Appl. No. 14/614,496, filed Feb. 5, 2015.
Pritee S. Mahajan, Kishor B Mahajan and A. B. Darekar, "A Review on Solid Lipid Nanoparticle (SLN): An Advanced Treatment Modality", 13 pages, International Journal of Pharmaceutical Sciences and Research, retrieved on Aug. 5, 2016 from the Internet: <URL: http://ijpsr.com/bft-article/a-review-on-solid-lipid-nanoparticle-sln-an-advanced-treatment-modality/?view=fulltext >.

* cited by examiner

*Primary Examiner* — Layla D Berry
(74) *Attorney, Agent, or Firm* — Schmeiser, Olsen & Watts, LLP

(57) ABSTRACT

A composition and associated method for treating a hepatitis C virus (HCV) infection in a subject who is human being. The composition includes: an anti-viral agent and/or a protease inhibitor; a polymerase inhibitor; one or more viral entry inhibitors; and one or more anti-fibrotic agents and/or anti-hemolytic agents including one or more Polyphenols and/or one or more Thiols. The composition may also include one or more sulfated oligosaccharide or non-anticoagulant glycosaminoglycans (GAGs). The method administers, to the subject, a therapeutic dose of the composition to treat the subject for the HCV infection.

18 Claims, 24 Drawing Sheets

COMPOSITION AND METHOD OF USE FOR COMBINATIONS OF ANTI-VIRAL PROTEASE, POLYMERASE INHIBITORS AND NATURAL BIOACTIVE COMPOUNDS IN THE TREATMENT OF HEPATITIS C INFECTION

This application is a continuation-in-part application claiming priority to Ser. No. 14/614,496, filed Feb. 5, 2015 which is incorporated herein by reference in its entirety and which claims priority to U.S. Provisional application No. 61/936,944 filed on Feb. 7, 2014. This application also claims priority to U.S. Provisional application No. 62/237,615 filed on Oct. 6, 2015 which is incorporated herein by reference in its entirety.

TECHNICAL FIELD

The present invention provides a composition effective for treating Hepatitis C Virus (HCV) infection in humans along with minimizing side effects, accelerating response to anti-viral, preventing relapse, and suppressing hepatic fibrosis.

BACKGROUND

The severe health conditions associated with chronic Hepatitis C Virus (HCV) infection remain a global concern. Various antiviral protease and polymerase inhibitors demonstrated significant anti-HCV efficacy against the different Geno types but associated with serious adverse effects and excessive cost along with significant relapse. Therefore, there is an urgent need for targeted antiviral agents for the treatment of HCV infection along viral entry inhibitors.

It is estimated that over 300 million people are infected with Hepatitis C virus (HCV) worldwide. Africa and the Eastern Mediterranean region have the highest documented infection rates, and Egypt has the highest infection rate for a single country in the world. In the United States, an estimated 4.1 million people are infected with HCV, representing approximately 1.8% of the population). Of these 4.1 million HCV-infected individuals, approximately 3.2 million have chronic Hepatitis C infection, and can therefore potentially spread HCV to others. Because of the low survival rate (~50%) of individuals with Hepatitis C and the high cost of treatment, Hepatitis C continues to be one of the most dangerous diseases in the world. It is therefore imperative to develop a novel, safe and effective formulation for the treatment of HCV infection that can quickly move into the clinical trials in comparison to the standard of care.

SUMMARY

The present invention provides a composition, comprising: an anti-viral agent and/or a protease inhibitor; a polymerase inhibitor; one or more viral entry inhibitors; and one or more anti-anti-fibrotic agents and/or anti-hemolytic agents comprising one or more Polyphenols and/or one or more Thiols. The composition may also comprise one or more non-anticoagulant glycosaminoglycans (GAGs).

The present invention provides a method of treating a hepatitis C virus (HCV) infection in a subject who is human being. The method comprises: administering to the subject a therapeutic dose of the composition to treat the subject for the HCV infection.

Figure 1:
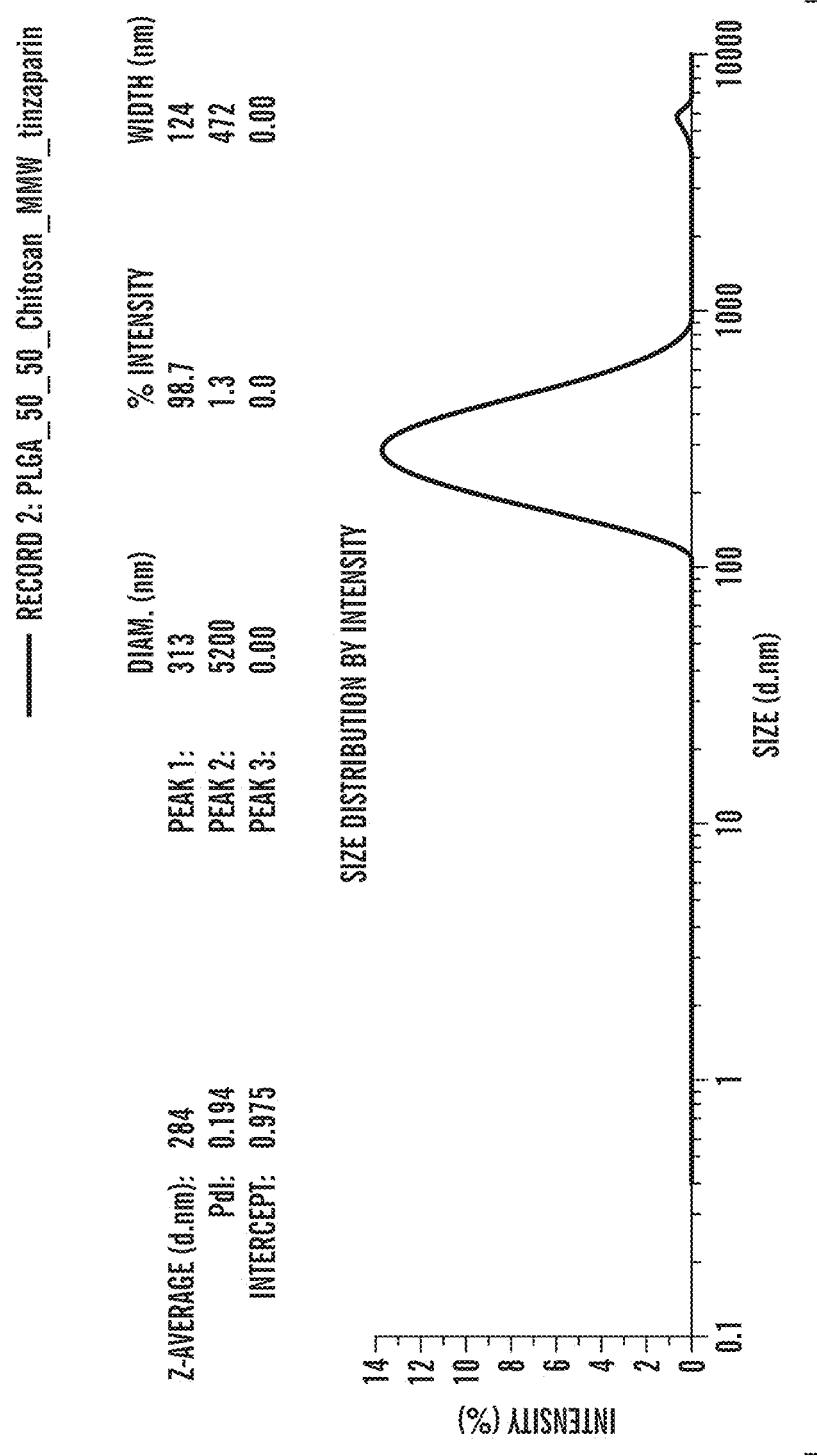
FIG. 1 depicts size measurement of chitosan grafted PLGA nanoparticles by dynamic light scattering (DLS), in accordance with embodiments of the present invention.
Figure 1:
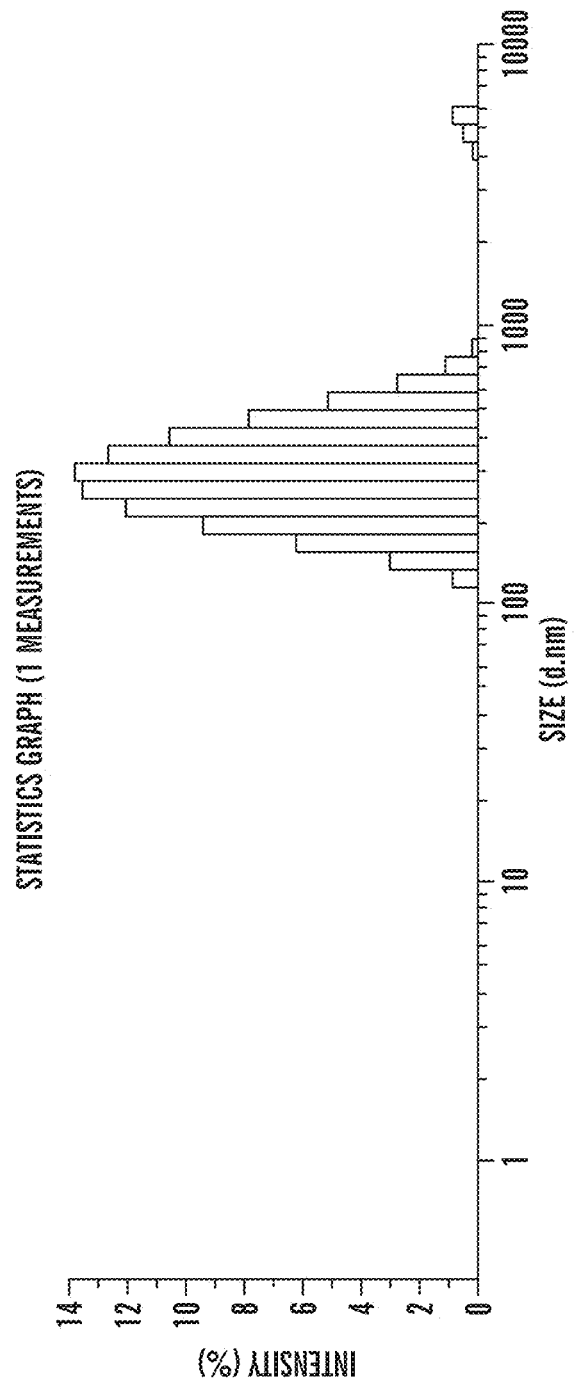

The natural bioactive ingredients (NBI) formulation containing EGCG, EGCG polymer, Lycopene, resveratrol, and other related derivatives could be used to improve the efficacy and safety of other anti-viral compounds such as Ribavirin combined in the same formulation (e.g., tablet, chewable tablet or capsule). This NBI formulation could be used with Daclatasvir, which inhibits the HCV nonstructural protein NS5A, which requires Ribavirin. The above NBI formulation could also be enhanced with other direct-acting antiviral agents including asunaprevir and sofosbuvir. Furthermore, the NBI formulation could be used with Ledipasvir, which inhibits hepatitis C virus NS5A protein and can be combined with sofosbuvir in the presence of viral entry inhibitors such as the polyphenol EGCG and sulfated glycosaminoglycans.

It is imperative that a new sensitive, cost effective, safe and efficient technology is developed in order to overcome this silent killer HCV. The application of nanotechnology in medicine provides unprecedented opportunities for addressing many of the current gaps in clinical diagnosis and therapy. Potential applications of this cutting edge technology could have a revolutionary impact on the treatment of Hepatitis C. In the past few decades, the development of controlled release systems based on nanoparticles that permit a sustained or pulsed release of encapsulated drug has attracted much interest. Polymeric particles are of particular interest, since the polymeric particles are more stable and permit administration by the parenteral route as well as oral route.

The novel composition and method of use in the present invention for eradication of Hepatitis C may comprise Natural Bioactive ingredients (NBI) selected from naturally derived polyphenols including EGCG, Resveratrol, Ellagic acid, Lycopene, sulfated glycosaminoglycans, and other NBI ingredients.

The use of PEGylated IFN γ with ribavirin has serious side effects and a significant proportion of patients infected with HCV have an unsatisfactory outcome with this therapy. Major advances have been realized in the development of specific non-nucleoside inhibitors of the viral NS5B RNA-dependent RNA polymerase. Clinical proof-of-concept for allosteric non-nucleoside HCV polymerase inhibitors has been reported and several compounds have progressed into preclinical and clinical studies. It is likely that in the future NS5B inhibitors will form an integral part of more effective anti-HCV therapies, combining the use of small-molecule antiviral drugs with or without the assistance of immune modulators such as IFNs. The combination of antiviral agent such as ribavirin in the presence of viral entry inhibitors, anti-fibrotic/anti-hemolytic agents, and with the polymerase inhibitor would result in synergistic effects and minimize the emergence of resistance and relapse. In one embodiment, the present invention combines known polymerase inhibitor such as Sofosbuvir (Isopropyl (2S)-2-[(2R, 3R, 4R, 5R)-5-(2, 4-dioxopyrimidin-1-yl)-4-fluoro-3-hydroxy-4-methyl-tetrahydrofuran-2-yl]methoxy-phenoxy-phosphoryl] amino] propionate) with known protease inhibitor such as 1-[(2R, 3R,4S,5R)-3,4-dihydroxy-5-(hydroxymethyl)oxolan-2-yl]-1H-1,2,4-triazole-3-carbox amide at 400 mg and 1000 mg in a solid dosage form, respectively, in combinations with anti-fibrotic/anti-hemolytic agents. Viral entry inhibitors, anti-fibrotic/anti-hemolytic agents that protect against live fibrosis and hemolytic anemia induced by ribavirin would include the following naturally driven polyphenols: (Resveratrol, Catchin EGCG, Ellagic acid, punicagilin, and other polyphenols) and Thiols (allin, N-acetyl cysteine, Sulforaphane, glutathione, and other Thiols). Additionally, polyanionic non-anticoagulant glycosaminoglycans such as non-anticoagulant Low Molecular Weight Heparins (NACH), heparan, dermatan, and other non-anticoagulant GAGs that bind and sequester Hepatitis C Virus lowering viral load would also be co-encapsulated or combined with the other components of the inventive composition in one embodiment. Other embodiments do not use the non-anticoagulant GAGs.

It is imperative that a new sensitive, cost effective, safe and efficient technology is developed in order to overcome this silent killer. The application of nanotechnology in medicine provides unprecedented opportunities for addressing many of the current gaps in clinical diagnosis and therapy. Polymeric nanoparticles are of particular interest, as the polymeric nanoparticles are more stable and permit administration by the parenteral route (subcutaneous) as well as oral route as tablet, chewable tablet or capsule. Furthermore, it is well known that nanoparticulate carriers not only have the potential to incorporate multiple drugs (either by encapsulation or chemical conjugation), but also have tremendous potential for targeted delivery. Keeping this in mind, the present invention in one embodiment provides a polymeric nanoparticle-based technology platforms incorporating the antiviral agent ribavirin or taribavirin and various types of polymerase inhibitors in the treatment of Hepatitis C, along with viral entry inhibitors and, in some embodiments, anti-fibrotic/anti-hemolytic agents as well. In one embodiment, the present invention conjugates a therapeutic peptide, p14 (NS3 peptide) that confers the ability to target viral NS3 helicase, which is anticipated to increase the efficacy of the drugs encapsulated into the nanoparticle platforms. In one embodiment, these drug loaded nanoparticles are attached to a monoclonal antibody (FAb fragments) directed against epitopes conserved on HCV surface E2 glycoprotein of genotypes 1a, 1b, 2a, 2b and 4. Thus, the incorporation of protease inhibitors and polymerase inhibitors (along with viral entry inhibitors and anti-fibrotic/anti-hemolytic agents, and Non-anticoagulant GAGs inside the nanoparticle would allow for optimal anti-viral efficacy and optimal safety profiles. At the same time, targeted delivery through αvβ3 ligand conjugation and combination therapy with incorporation of taribavirin or ribavirin in the same nanoparticle is expected to increase the efficacy of the formulation via targeted delivery to HCV and/or the liver.

The present invention may be accomplished, in various embodiments, as follows.

I: Synthesis and characterization of different nanoformulations incorporating an antiviral agent such as ribavirin or other anti-viral agents, polymerase inhibitors such as sofosbuvir along with viral entry inhibitors, anti-fibrotic/anti-hemolytic such as polyphenol/thiol, and Non-anticoagulant GAGs such as (NACH, Oligosaccharide, dermatan sulfate, . . . );

II: Determine the efficacy of the nanoformulation in cells in vitro using confocal imaging and qualitative in vitro anti-HCV screening;

III: Determine the efficacy of selected nanoformulations in vivo using chimeric urokinase-type plasminogen activator (uPA)-severe combined immunodeficiency (SCID) (uPA-SCID) mice engrafted with human hepatocytes.

Figure 8:
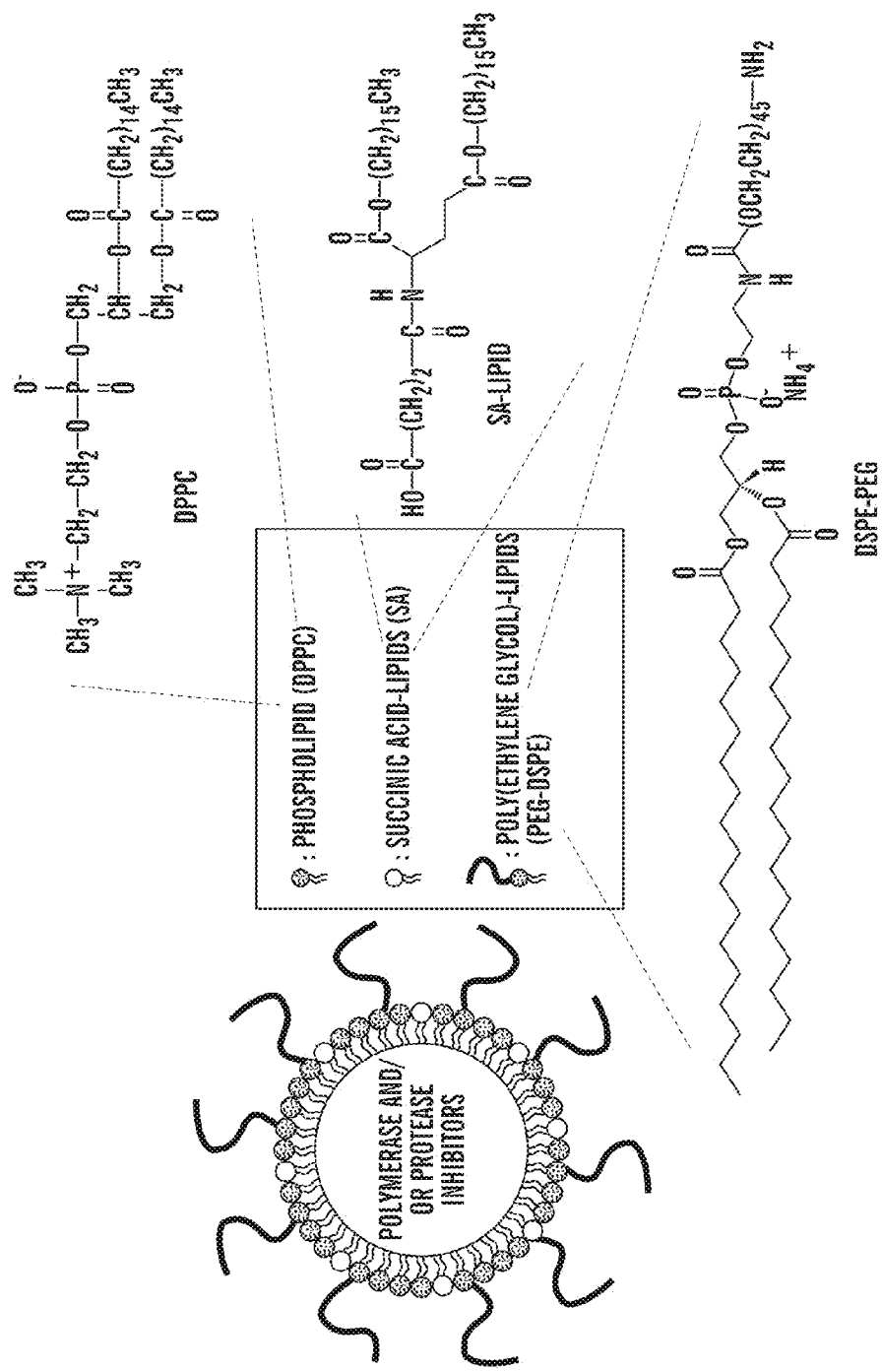
FIG. 8 depicts a sketch illustrating the design of nanoparticles for drug delivery wherein Nanoformulation are synthesized for the encapsulation of antiviral polymerase and protease inhibitors containing viral entry inhibitors and anti-fibrotic agents along with targeting for hepatic cells using coating/conjugation with Lactobionic acid, glycyrrhizin, and/or Galactosylated, in accordance with embodiments of the present invention.

The following formulations and nanoformulations were derived:

1. Solid dosage form combining anti-viral agent such as Ribavirin (1-[(2R,3R,4S,5R)-3,4-dihydroxy-5-(hydroxymethyl) oxolan-2-yl]-1H-1,2,4-triazole-3-carboxamide at 500-1000 mg/tablet or capsule in sustained release formulation plus polymerase inhibitor such as Sofosbuvir (Isopropyl (2S)-2-[(2R,3R,4R,5R)-5-(2,4-dioxopyrimidin-1-yl)-4-fluoro-3-hydroxy-4-methyl-tetrahydrofuran-2-yl]methoxy-phenoxyphosphoryl]amino] propionate) at 200-400 mg/tablet, chewable tablet or capsule, along with anti-fibrotic/anti-hemolytic agents combination of naturally driven Polyphenol/Thiols, and Non-anticoagulant GAGs inside the nanoparticle would allow for optimal anti-viral efficacy and optimal safety profiles.
2. Nanoformulation containing Ribavirin (100-200 mg) and Sofosbuvir (40-100 mg), along with anti-fibrotic/anti-hemolytic agents' combination of naturally driven Polyphenol/Thiols, and Non-anticoagulant GAGs in solid lipid nanoparticles, PLGA-PEG nanoparticles, Chitosan-fatty acid, Chitosan-PLGA, Chitosan-Hyaluronic acid coated with Lactobionic, glycyrrhizin and/or galactosylated for hepatic targeting.
3. Nanoformulation containing Ribavirin (100 mg) and Sofosbuvir (40 mg) and lower doses in solid lipid nanoparticles, PLGA-PEG nanoparticles, Chitosan-fatty acid, Chitosan-PLGA, Chitosan-Hyaluronic acid, along with anti-fibrotic/anti-hemolytic agents' combination of naturally driven Polyphenol/Thiols, and Non-anticoagulant GAGs and conjugated with avb3 integrin ligand and/or p14 peptide (NS3 peptide) for HCV targeting.
4. Nanoformulation containing Ribavirin (10-20 mg) and Sofosbuvir (4-10 mg) in solid lipid nanoparticles, PLGA-PEG nanoparticles, Chitosan-fatty acid, Chitosan-PLGA, Chitosan-Hyaluronic acid, along with anti-fibrotic/anti-hemolytic agents' combination of naturally driven Polyphenol/Thiols, and Non-anticoagulant GAGs and conjugated with avb3 integrin ligand and/or p14 peptide (NS3 peptide) for HCV targeting and coated or conjugated with Lactobionic, glycyrrhizin and/or galactosylated for hepatic targeting.

Application of nanotechnology in medicine provides unprecedented opportunities for addressing many of the current gaps in the diagnosis and therapy. Potential applications of this cutting edge technology could have a revolutionary impact on the treatment of Hepatitis C. In last few decades, the development of controlled release systems based on nanoparticles that permit a sustained or pulsed release of encapsulated drug has attracted much interest. Polymeric particles are especially interesting as the polymeric particles are more stable and permit administration by the parenteral route as well as oral route. Furthermore, it is well known that nanoparticulate carriers not only have the potential to incorporate multiple drugs (either by encapsulation or chemical conjugation), but also have the tremendous potential for targeted delivery. Many studies have documented that custom-synthesized nanoparticles accumulate in the liver. Proper delivery of antiviral drugs to the HCV and/or the liver, is a prerequisite for efficient Hepatitis C treatment. Thus, nanoparticles could provide the added advantage of delivering drugs into the liver effectively, thereby increasing the efficacy of the drugs. In one embodiment, nanoparticulate carrier systems can be fluorescently labeled with different dyes, which enable investigation of the pathways and accumulation of nano-carriers in real time. Tracking of the Nano-carriers allow identification of mechanistic pathways of localization and activity, thereby providing the basis for optimized formulations for better results. Conjugation of a therapeutic peptide, such as p14 (NS3 peptide), that has the ability to target viral NS3 helicase, increases the efficacy of nano-encapsulated drugs. Monoclonal antibodies (Fab fragments) or TAT peptide targeting HCV also can be useful for efficient targeted delivery vehicles that can be conjugated on the surface of the drug loaded nanoparticles with protease inhibitors and RNA polymerase inhibitors.

One effective therapy for Hepatitis C is combination therapy using PEGylated IFN γ (PEG-IFNγ) and ribavirin. This combination therapy involved multiple doses of PEG-IFN and ribavirin and takes more than 48 weeks to complete. However, the success rate is only around 50%. In addition, the cost of IFNγ combination therapy is high, efficiency is low, and the therapy has serious side effects. It is therefore imperative to develop novel, sensitive, cost effective, safe and efficient technologies that can effectively overcome this latent killer. With this in mind, the present invention provides a polymeric nanoparticle-based technology antiviral drug for the treatment of Hepatitis C. Conjugation of a therapeutic peptide, p14 (NS3 peptide), that has the ability to target viral NS3 helicase, is also used in order to increase the efficacy of the drugs. Conjugation of Monoclonal antibodies (Fab fragments) or TAT peptide targeting HCV, on the surface of the drug loaded nanoparticles can be highly efficient and can be used for the treatment most of the types of the HCV including genotype 1a, 1b, 2a, 2b, 4 etc.

FIG. 4 depicts a sketch illustrating the Design of Solid lipid nanoparticles (SLN) for drug delivery wherein nanoformulations are synthesized for the encapsulation of protease and polymerase inhibitors with or without interferon, with anti-fibrotic/anti-hemolytic agents' combination of naturally driven Polyphenol/Thiols, and Non-anticoagulant GAGs, along with targeting for hepatic cells using Lactobionic acid, glycyrrhizin, and/or Galactosylated, in accordance with embodiments of the present invention.

FIG. 5 depicts a sketch illustrating the Design of Solid lipid nanoparticles (SLN) for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatitis C virus can be targeted by conjugation of high affinity □v□3 ligand and coating/conjugation for hepatic cells using Lactobionic acid, glycyrrhizin, and/or Galactosylated, in accordance with embodiments of the present invention.

FIG. 6 depicts a sketch illustrating the Design of nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

FIG. 7 depicts a sketch illustrating the Design of nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

FIG. 8 depicts a sketch illustrating the Design of nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 9:
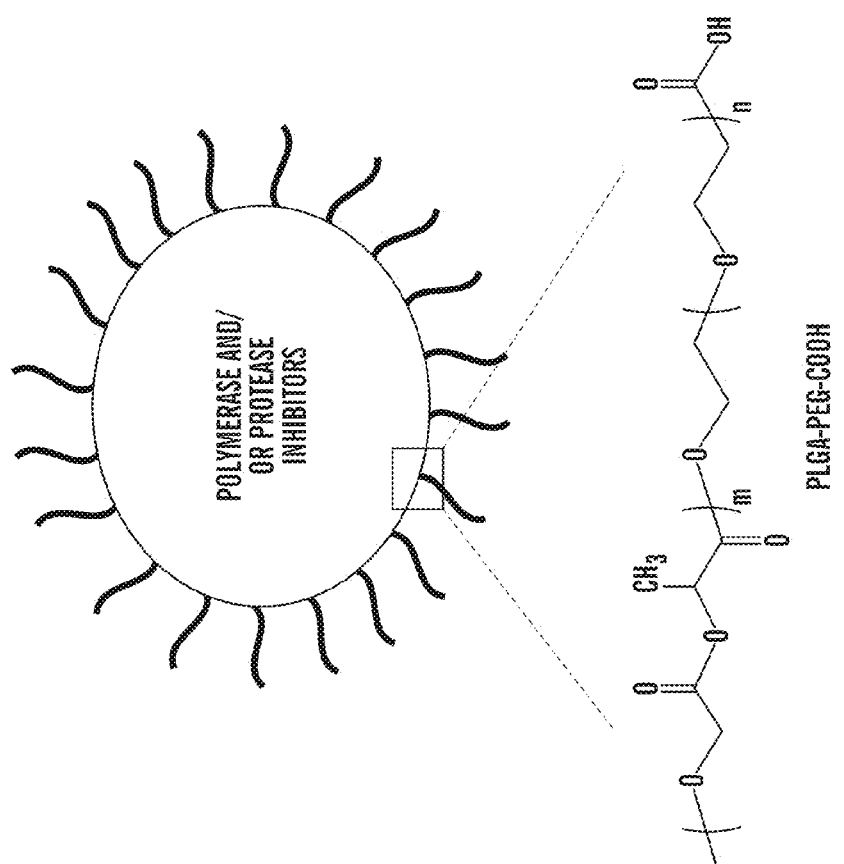
FIG. 9 depicts Aa sketch illustrating the design of PLGA-PEG nanoparticles for drug delivery wherein nanoformulations are synthesized for the encapsulation of antiviral polymerase and protease inhibitors containing viral entry inhibitors and anti-fibrotic agents along with targeting for hepatic cells using coating/conjugation with Lactobionic acid, glycyrrhizin, and/or Galactosylated, in accordance with embodiments of the present invention.

FIG. 9 depicts a sketch illustrating the Design of PLGA-PEG nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 10:
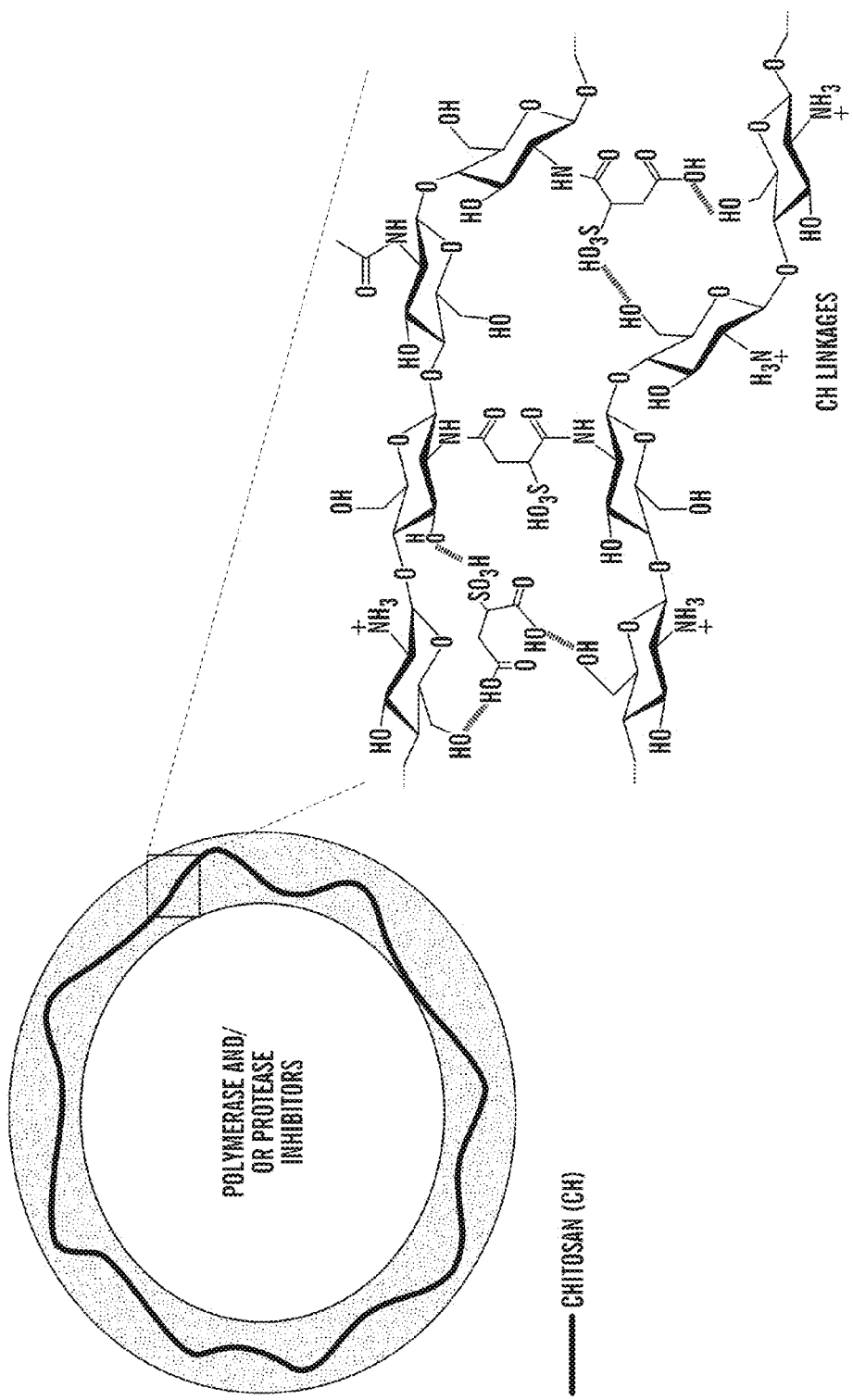
FIG. 10 depicts a sketch illustrating the design of cross-linked chitosan nanoparticles for drug delivery wherein nanoformulations are synthesized for the encapsulation of polymerase and protease inhibitors containing viral entry inhibitors and anti-fibrotic agents along with targeting for hepatic cells using coating/conjugation with Lactobionic acid, glycyrrhizin, and/or Galactosylated, in accordance with embodiments of the present invention.

FIG. 10 depicts a sketch illustrating the Design of cross-linked Chitosan nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 11:
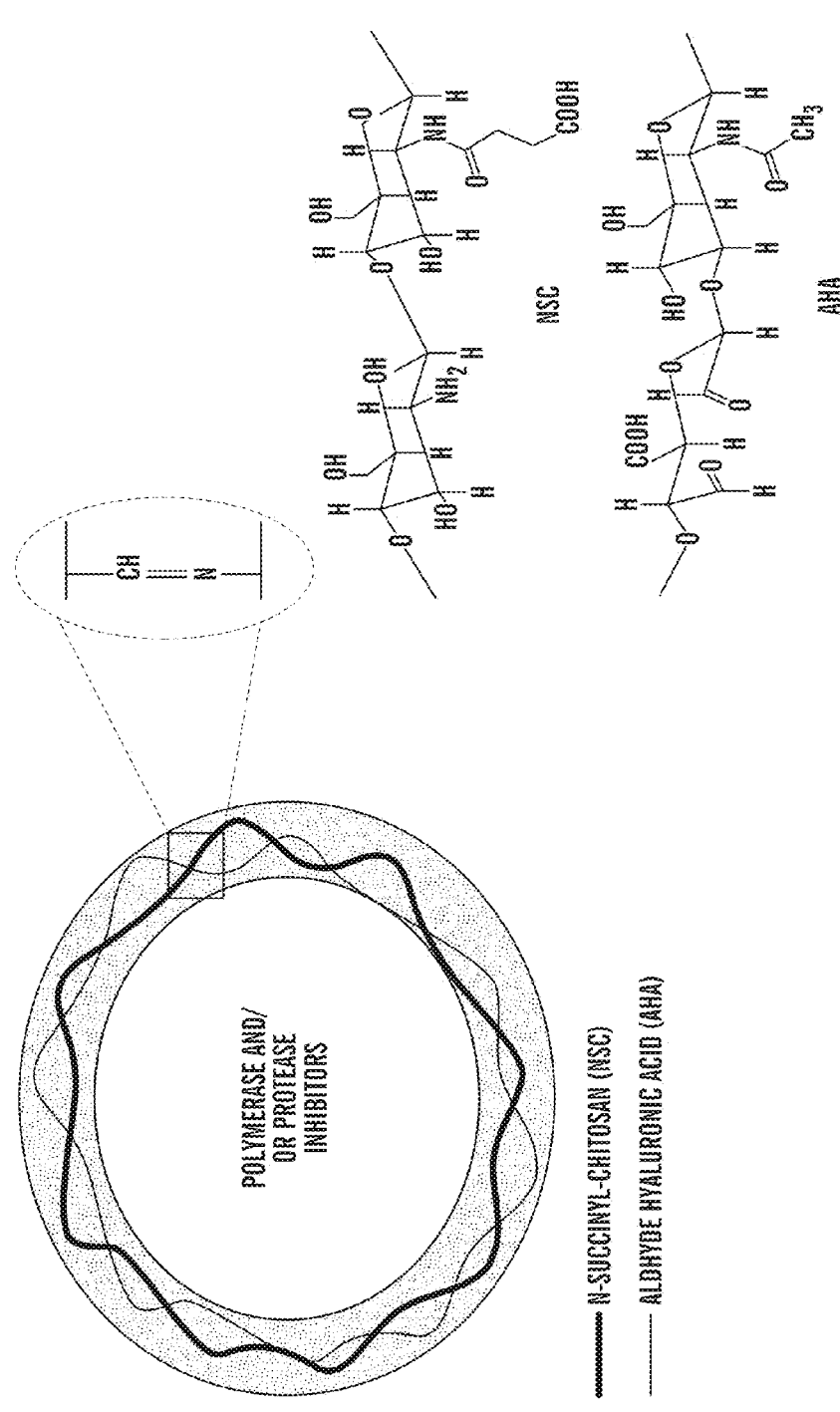
FIG. 11 depicts a sketch illustrating the design of hyaluronic acid (HA) cross-linked, via covalent bonding, with Chitosan nanoparticles for drug delivery wherein nanoformulations are synthesized for the encapsulation of polymerase and protease inhibitors containing viral entry inhibitors and anti-fibrotic agents, and along with targeting for hepatic cells using coating/conjugation with Lactobionic acid, glycyrrhizin, and/or Galactosylated, in accordance with embodiments of the present invention.

FIG. 11 depicts a sketch illustrating the Design of Hyaluronic acid (HA) cross-linked with Chitosan nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 12:
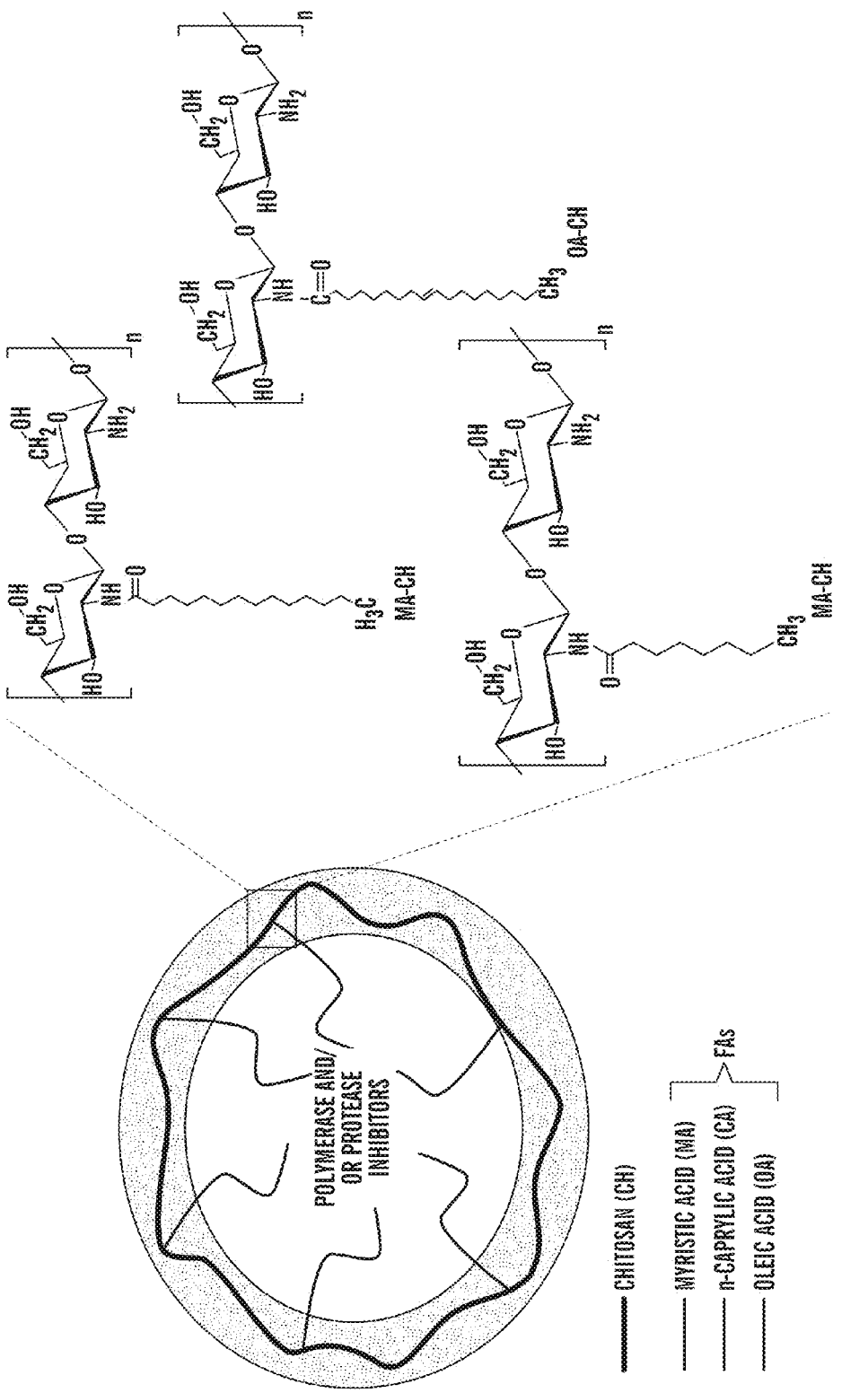
FIG. 12 depicts a sketch illustrating the design of fatty acids (FA) cross-linked, via covalent bonding, with chitosan nanoparticles for drug delivery wherein nanoformulations are synthesized for the encapsulation of polymerase and protease inhibitors containing viral entry inhibitors and anti-fibrotic/anti-hemolytic agents along with targeting for hepatic cells using coating/conjugation with Lactobionic acid, glycyrrhizin, and/or Galactosylated, in accordance with embodiments of the present invention.

FIG. 12 depicts a sketch illustrating the Design of fatty acids (FA) cross-linked with Chitosan nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 13:
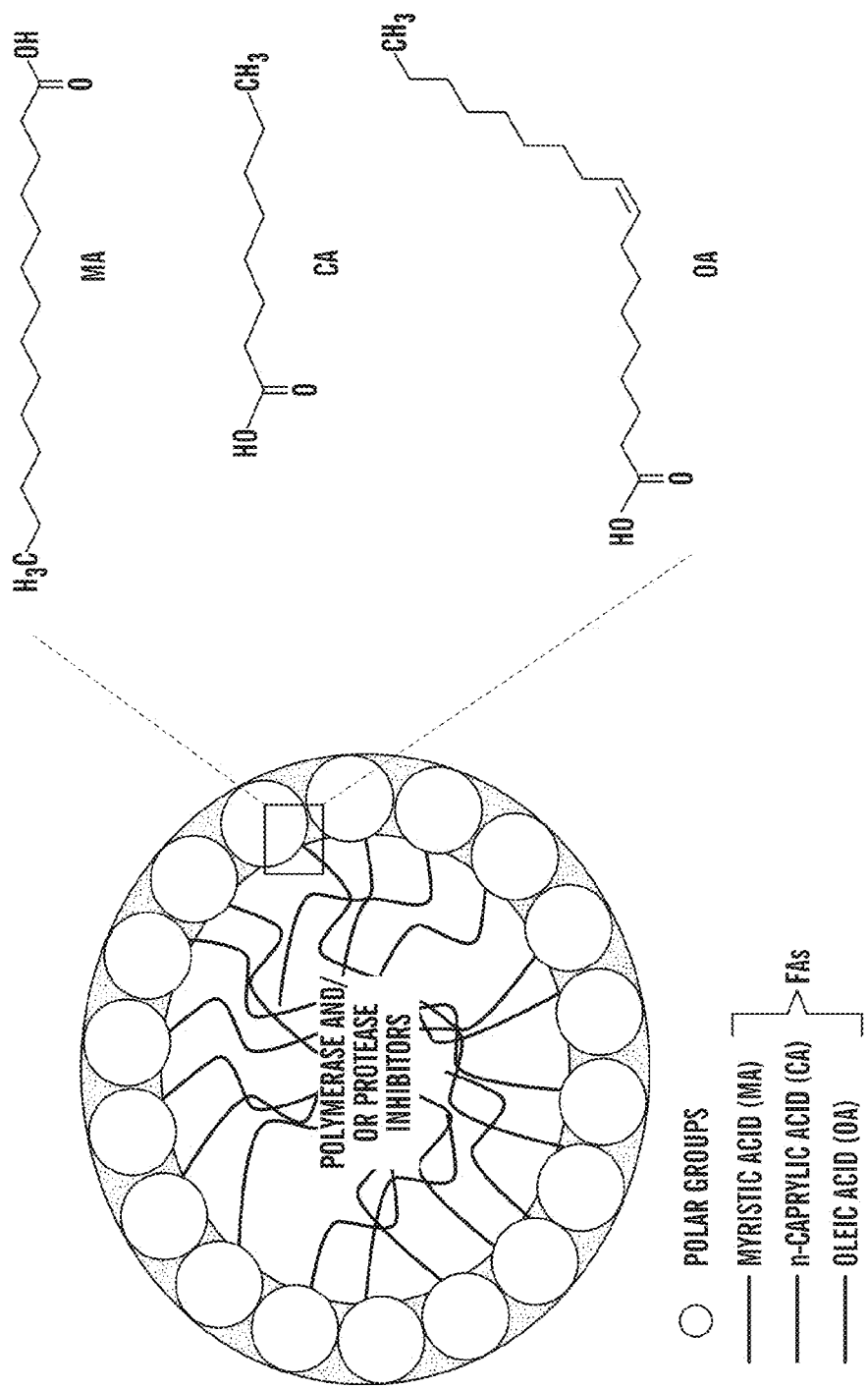
FIG. 13 depicts a sketch illustrating the design of fatty acids (FA) nanoparticles for covalent bonding, with Glycyrrhizic acid or Lactobionic acid and then encapsulated with polymerase and protease inhibitors may be utilized. Glycyrrhizin is a substance found in liquorice. Active targeting to HCV may use αvβ3 integrin ligand (Cyclic RGDF or XT199 and/or to the liver may use Glycyrrhetinic or Lactobionic Acids.

FIG. 13 depicts a sketch illustrating the Design of fatty acids (FA) nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 14:
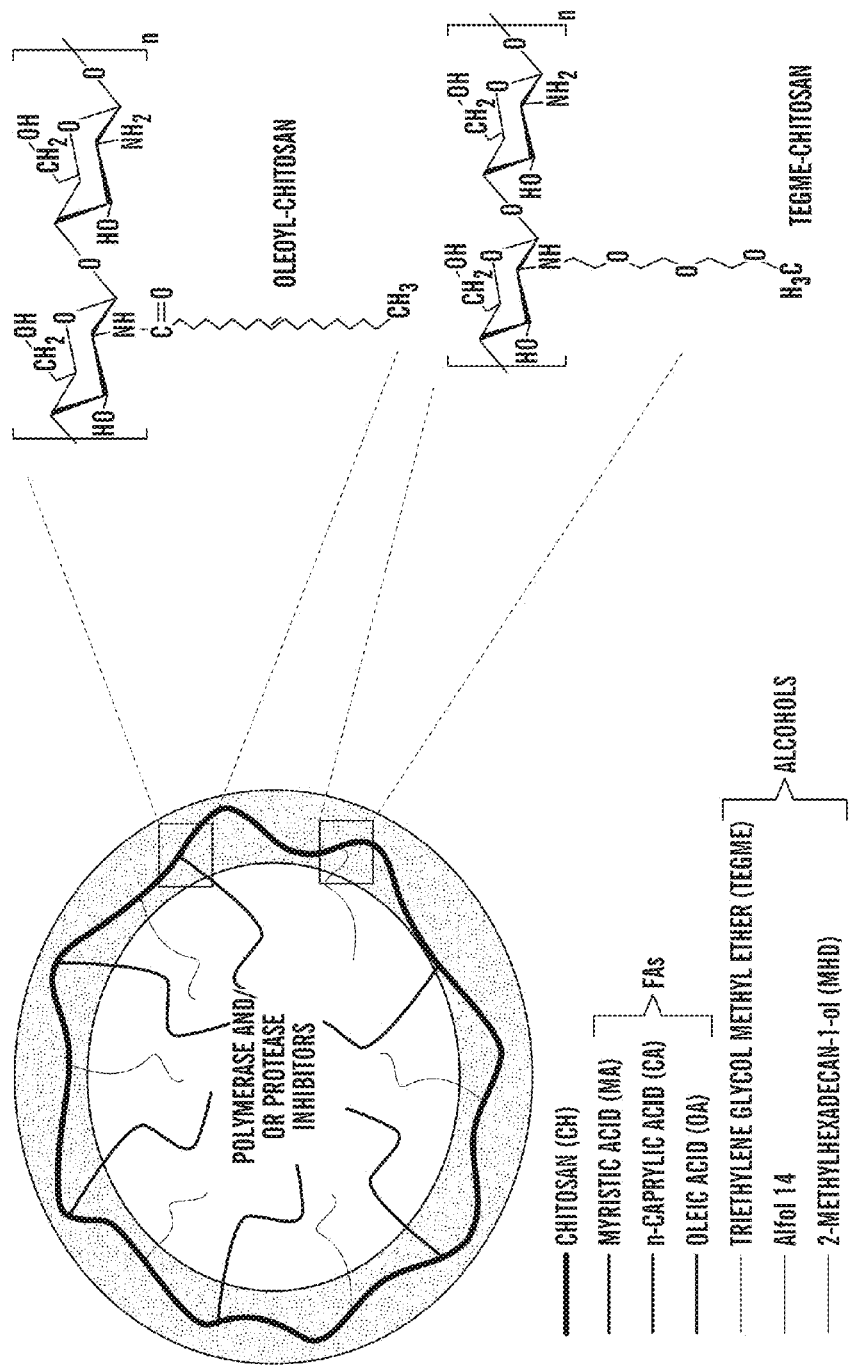

FIG. 14 depicts a sketch illustrating the Design of fatty acids (FA) cross linked to alcohol nanoparticles for drug delivery wherein nanoformulations are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 15:
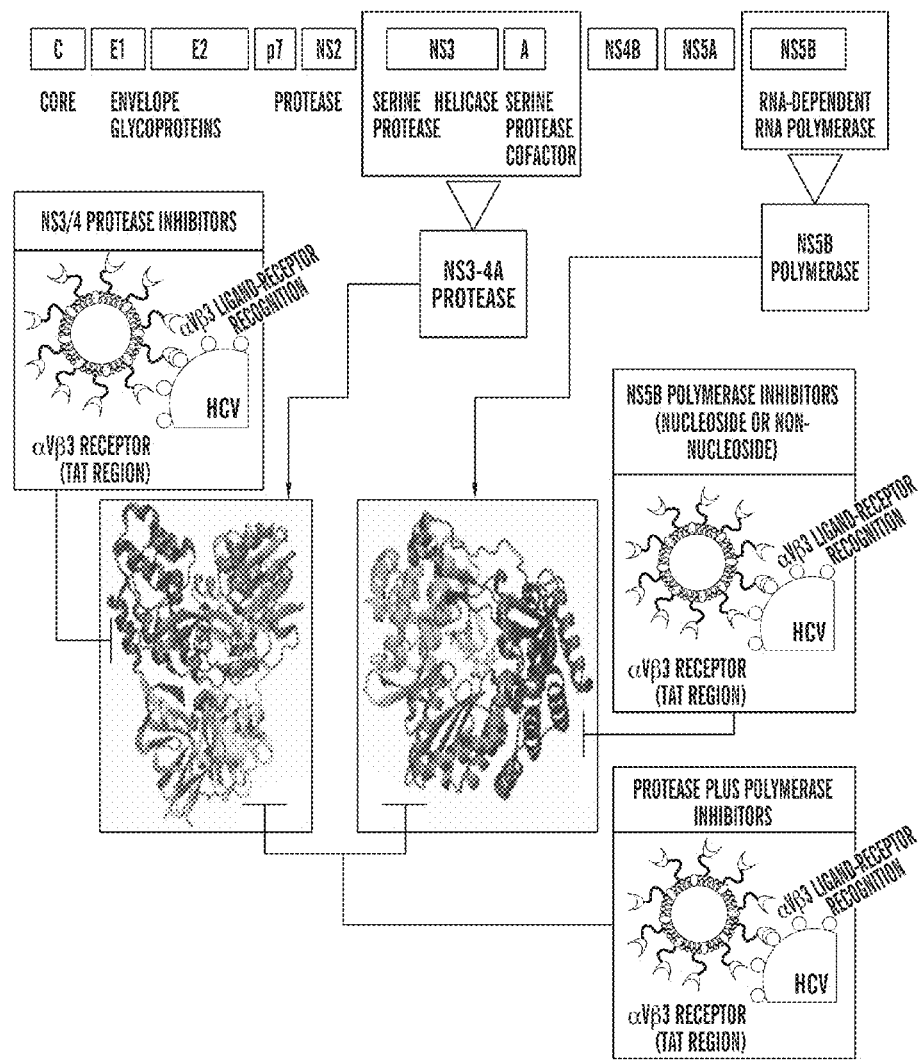

FIG. 15 depicts various anti-viral compounds that could be encapsulated for hepatic and/or viral targeting, in accordance with embodiments of the present invention.

EXAMPLE 1

Qualitative in Vitro anti-HCV screening: Detection of the Effect of the prepared Compounds on Cancer Cell Line: HepG2 cells were washed twice in RPMI 1640 (Cambrex) media supplemented with 200 µM L-glutamine (Cambrex) and 25 µM HEPES buffer; N-[2-hydroxyethyl] piperazine-N'-[2-ethanesulphonic acid] (Cambrex) and were suspended at $2\times10^5$ cells $ml^{-1}$ in RPMI culture media (RPMI supplemented media, 10% fetal bovine serum (FBS); GIBCO-BRL). The cells were left to adhere on the polystyrene 6-well plates for 24 hours in 37° C., 5% $CO_2$, 95% humidity incubator. After 24 hr. the cells were washed twice from debris and dead cells by using RPMI supplemented media. Different concentrations (100, 50, 20, 10 or 5 µg/ml) from each prepared compound were added in 6-well plates. Positive and negative control cultures were included. Cultures were incubated for 72 hours in 37° C., 5% $CO_2$, 95% humidity. For examining the cell cycle of control and treated cells, the adherent cells were detached from the plate using 1 ml trypsin EDTA (200 mg/L for EDTA, 500 mg/L for trypsin in a ratio 1:250) for 1-3 minutes, the action of trypsin is stopped by the addition of 5 ml RPMI culture media. The cells were scrapped and collected in 15 ml falcon tube, then washed twice by RPMI supplemented media and once by phosphate buffer saline (PBS), after each wash centrifuge at 1000 rpm for 5 minutes. Resuspended the pellet in 1 ml Propidium iodide (Sigma) with concentration (50 ml/l in 0.1% sodium citrate and 01% triton X100), incubate the tubes in dark at 4° C. for at least 60 min. The effect of the compounds on HepG2 cell line was examined using FACS flow cytometer (BD Bioscience, San Diego, Calif., USA).

EXAMPLE 2

Qualitative in Vitro anti-HCV screening: Prepared compounds in the present study were investigated for its In Vitro action as anti-HCV using the hepatocellular carcinoma HepG2 cell line infected with the hepatitis-C virus. During the last few years, a number of cell culture systems showed to have the ability to harbor and support reliable and efficient progression of this virus. Among several human hepatocyte cell lines analyzed, the hepatocellular carcinoma HepG2 cell line was found to be most susceptible to the HCV infection. On the other hand, monitoring of the HCV viremia pre- and post-antiviral therapy through the detection of viral (+) and/or (−) RNA strands by the use of qualitative reverse transcription-polymerase chain reaction (RT-PCR) has become the most frequently-used, reliable and sensitive technique. Recently, it has been reported that the detection of the (−) strand HCV-RNA using the RT-PCR is a very important tool for understanding the life cycle of the HCV and provides a reliable marker for the diagnosis of HCV and monitoring the viral response to antiviral therapy.

Based on the preceding facts in EXAMPLE 2, the adopted method in the present study contributes to the simultaneous detection of the (+) and/or (−) HCV-RNA strands in HepG2 hepatoma cells infected with HCV. Inhibition of viral replication was detected by amplification of viral RNA segments using the RT-PCR technique, both in the cultivated cells alone (as a positive control) and in the presence of variable concentrations of the test compounds at optimal temperature. The test compound is considered to be active when it is capable of inhibiting the viral replication inside the HCV-infected HepG2 cells, as evidenced by the disappearance of the (+) and/or (−) strands viral RNA-amplified products detected by the RT-PCR (compared with the positive control). Using the same method, HCV replication was examined in peripheral blood cells from 10-20 HCV infected patients before and after the blood cells of the infected patients were subjected in an In Vitro culture to different concentrations of the prepared compounds.

EXAMPLE 3

Flow cytometry analysis of intracellular staining of HCV core antigen in infected HepG2 cells: The intracellular staining of HCV core antigen in HCV infected HepG2 cells were quantified before and after incubation with the different concentrations of the test compounds by using a fluorescence activated cell sorting (FACS) based assay. Intracellular staining labeling was performed by direct immunofluorescence. HepG2 cells (collected after addition of trypsin) were centrifuged and supernatants were removed. Cell pellets were washed 4 times with PBS. For intracellular staining, cells were incubated with 4% paraformaldehyde for 10 min and 0.1% Triton X-100 in Tris buffer (pH 7.4) for 6 min. After washed with PBS, cells were incubated with FITC-labeled F (ab)2 portion of HCV core antibody (at 1:2000 dilutions or according to previous standardization) for 30 min at 4° C. Cells were washed with PBS containing 1% normal goat serum and suspended in 500 µl and were analyzed by flow cytometry (FACS Calibure, BD). Mean fluorescence intensity were determined using Cell Quest software (Becton Dickinson)

EXAMPLE 4

Synthesis of chitosan grafted poly (lactic-co-glycolic acid) (PLGA) nanoparticles: Synthesis of chitosan grafted PLGA nanoparticles using a modification a double emulsion-diffusion-evaporation technique. Thus, with slight modification of this method we have already demonstrated our ability to synthesis chitosan grafted PLGA nanoparticles. Thus, using emulsion technique we can synthesis nanoparticles of size of around ~250 nm in diameter. The size of the nanoparticles is determined using dynamic light scattering (DLS) (see FIG. 1). FIG. 1 depicts size measurement of chitosan grafted PLGA nanoparticles by dynamic light scattering (DLS), in accordance with embodiments of the present invention.

EXAMPLE 5

Cellular uptake of chitosan grafted PLGA nanoparticles: Cell Culture: HepG2 cells grown in Eagle's Minimum Essential Medium (EMEM) (Invitrogen, Grand Island, N.Y.) supplemented with 10% fetal calf serum (Atlanta Biologicals, Lawrenceville, Ga., USA). Penicillin/streptomycin (1%) was also present in the culture media. The cells were trypsinized, subjected to centrifugation, and then the cell pellet was resuspended in suitable media. An aliquot (1 mL) of the suspension was transferred to a 35-mm glass bottom culture dishes, and the cells incubated for 24 hours (hours) at 37° C. under a 5% $CO_2$ atmosphere.

Figure 2:
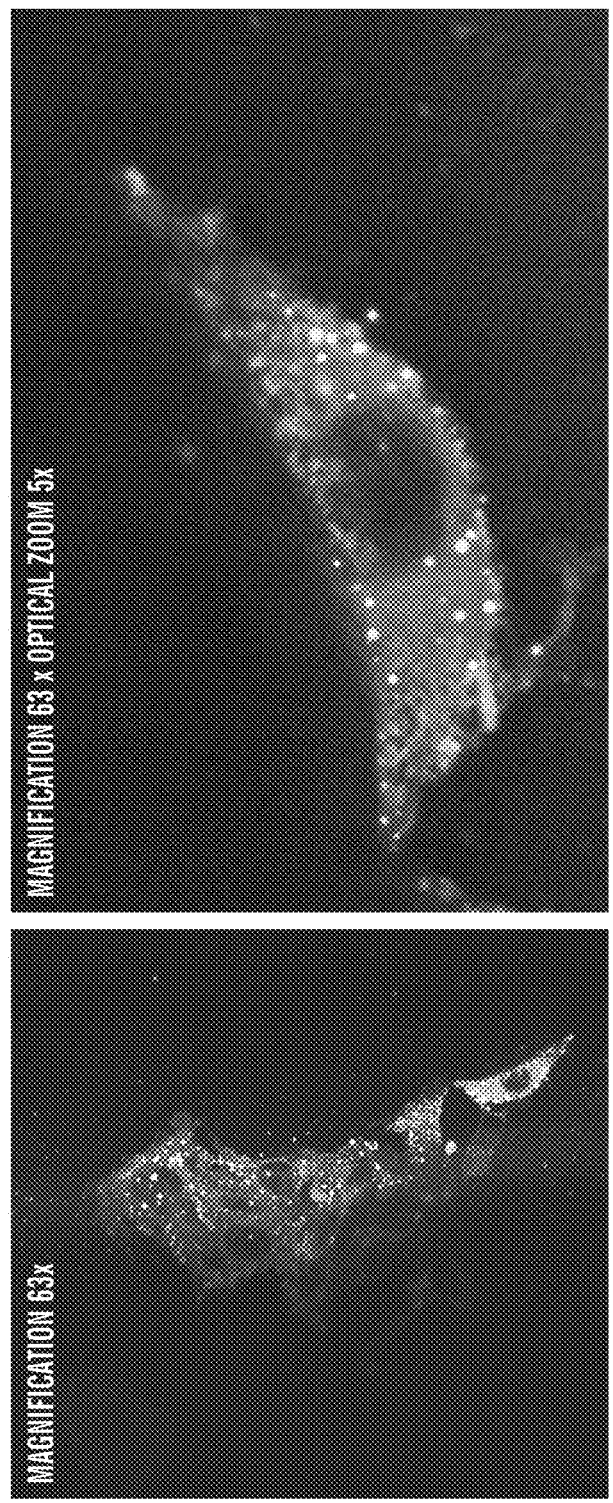
FIG. 2 depicts confocal imaging of HepG2 cell showing the uptake of Cy3-labeled chitosan grafted poly (lactic-co-glycolic acid) (PLGA) nanoparticles, in accordance with embodiments of the present invention.

Confocal Imaging: HepG 2 cells cultured as described above and treated with Cy3 dye-labeled chitosan grafted PLGA nanoparticles (37° C., 5% $CO_2$) for 2 hrs. After 2 hours, cells were washed several time with phosphate buffered saline (PBS), and then fixed in 1% formaldehyde (Sigma, St. Louis Mo., USA). Confocal images were taken using a Leica TCS SP5 confocal microscope equipped with a 63×(NA=1.3 glycerol immersion) objective, a 543 nm excitation wavelength and an emission filter for detection between 555 nm and 620 nm (see FIG. 2). FIG. 2 depicts confocal imaging of HepG2 cell showing the uptake of Cy3-labeled chitosan grafted poly(lactic-co-glycolic acid) (PLGA) nanoparticles, in accordance with embodiments of the present invention.

EXAMPLE 6

Three different polymeric nano-formulations were synthesized, as listed below. The present invention combines known polymerase inhibitor such as Sofosbuvir (Isopropyl (2S)-2-[(2R, 3R, 4R, 5R)-5-(2, 4-dioxopyrimidin-1-yl)-4-fluoro-3-hydroxy-4-methyl-tetrahydrofuran-2-yl] methoxyphenoxy-phosphoryl] amino] propionate) with known protease inhibitor such as 1-[(2R,3R,4S, 5R)-3,4-dihydroxy-5-(hydroxymethyl)oxolan-2-yl]-1H-2,4-triazole-3-carbox amide at 400 mg and 1000 mg, respectively, were co-encapsulated in the following nanoparticles along with viral entry inhibitors, anti-fibrotic/anti-hemolytic agents' combination of naturally driven Polyphenol/Thiols, and Non-anticoagulant GAGs:
  a) cross-linked, via covalent bonding, polyvinyl pyrrolidone (PVP) hydrogel nanoparticles;
b) cross-linked, via covalent bonding, alginate-chitosan nanoparticles;
c) chitosan grafted poly(lactic-co-glycolic acid) (PLGA) nanoparticle.

The nanoparticles were synthesized and characterized using dynamic light scattering (DLS) and transmission electron microscopy (TEM). Uptake of the nanoparticles was examined in the human hepatocellular HepG2 cell line using confocal microscopy. Based on in vitro release kinetics, entrapment efficiency and in vitro uptake in HepG2 cells, the three most effective formulations were chosen for further studies.

EXAMPLE 7

Synthesis of alginate-chitosan nanoparticles: Alginate-chitosan nanoparticles encapsulating IFN γ were synthesized using the ionic gelation method (33-34). Low viscosity sodium alginate and low molecular weight chitosan were used for the synthesis of the nanoparticles. The alginate solution was prepared in deionized water; the chitosan solution was prepared in 1% v/v acetic acid. The pH of both solutions were adjusted to approximately 6.0, and the solutions were filtered (0.22 μm pore size) prior to use. Nanoparticles were prepared under sterile conditions by mixing appropriate volumes of 0.005% (w/w) sodium alginate and IFN followed by the addition of 1% (w/w) chitosan under stirring for 2 hours (hours) at room temperature. The amount of IFN was adjusted until we achieve maximum loading efficiency. Nanoparticles were characterized by DLS, zeta size and TEM. For co-encapsulation of Sofosbuvir, ribavirin with or without EGCG, an appropriate amount of Sofosbuvir and ribavirin were added to the solution.

EXAMPLE 8

Synthesis of hybrid cross-linked PVP hydrogel nanoparticles: Nanoparticles encapsulating IFN were synthesized by in situ polymerization of various monomers, as described below. Polymerization reactions were carried in a reverse micelle environment. Sodium bis-ethyl hexyl sulphosuccinate or aerosol OT (AOT; Sigma Aldrich, St. Louis, Mo., USA) were used as a surfactant for micelle formation. Surfactant (either sodium bisethylhexylsulphosuccinate or AOT) was dissolved in n-hexane (typically 0.03M to 0.1M AOT in hexane). Aqueous solutions of monomer were added together with the cross-linking reagent N' methylenebisacrylamide (MBA), the initiator ammonium per-sulphate (APS), the activator ferrous ammonium sulphate (FAS), and where indicated, an aqueous solution of IFN. The polymerization reaction was carried out in the presence of $N_2$ gas. The monomers to be tested are vinylpyrrolidone (VP), N-isopropyl acrylamide (NIPAAM) and N-3 amino propyl methyl acrylamide (APAAM). For co-encapsulation, taribavirin were added along with IFN to the reverse micelles. To initiate the polymerization reaction, 15 μl of a saturated solution of APS (2% w/w of monomers) and 20 μl of a 0.05% w/v solution FAS (0.07% w/w of monomers) was used. The reaction was allowed to proceed at room temperature for 2-3 hrs.

EXAMPLE 9

Synthesis of chitosan grafted PLGA nanoparticles: In brief, this double emulsion-diffusion-evaporation technique of synthesis of nanoparticles is as follows: 50 mg of PLGA was dissolved in 2 mL of ethyl acetate, and then 200 microliter of a solution of IFN was added. The mixture was sonicated for 5 seconds using a probe sonicator, and then the emulsion was immediately be added to an aqueous stabilizer mixture, containing 100 mg of polyvinyl alcohol (PVA) and 10 mg of chitosan in 10 ml of water, drop wise with stirring. The entire solution was sonicated again for approximately 10 seconds using a probe sonicator. The emulsion was stirred at room temperature for 1 hour, and then the organic phase was removed using a rotatory evaporator. For co-encapsulation of taribavirin, an appropriate amount of taribavirin was added.

EXAMPLE 10

Entrapment efficiency: Entrapment efficiency for taribavirin were determined by filtering a known amount of the nanoparticles through a 0.1 m filter membrane to separate free taribavirin. The amount of taribavirin was determined using high performance liquid chromatography (HPLC). Entrapment efficiency (E %) were determined based on the total concentration of drug (taribavirin) in the system (free+ encapsulated; $[Drug]_0$) and the concentration of drug in the filtrate ($[Drug]_f$) using the following formula:

$E\% = (([Drug]_0 - [Drug]_f)/[Drug]_0) \times 100$

EXAMPLE 11

Release kinetics of ribavirin or taribavirin and sofosbuvir from the nanoparticles: The in vitro release kinetics of the nanoparticles was evaluated in phosphate buffered saline (PBS) and fetal bovine serum (FBS). A defined amount of IFN and taribavirin encapsulated in nanoparticles was suspended in 10 ml of PBS, and the solution was kept at room temperature. At various time intervals, the solution was vortexed, and an aliquot (1 mL) of the solution removed and subjected to centrifugation at 10,000×g to separate released drug (taribavirin or ribavirin) from nanoparticle-encapsulated material. The concentration of released drug was determined using HPLC (for taribavirin). The percent release of ribavirin was determined according to the following formula:

% Release=$([Drug]_{f,t}/([Drug]_0) \times 100$

Where $[Drug]_{f,t}$ is the concentration of taribavirin in the supernatant at time t. Similarly, to determine the release kinetics in FBS, a defined amount of taribavirin encapsulated in nanoparticles was suspended in 10 ml of 20% FBS. Release kinetics was analyzed as described for PBS.

EXAMPLE 12

Analysis of particle size by DLS and TEM: Size distribution of IFN and taribavirin-encapsulated nanoparticles in an aqueous dispersion was determined using a Malvern zeta sizer (Malvern Instrumentation Co, Westborough, Mass., USA). The size and morphology of the nanoparticles were also examined using a JEOL JEM-100CX transmission electron microscope.

EXAMPLE 13

Figure 3:
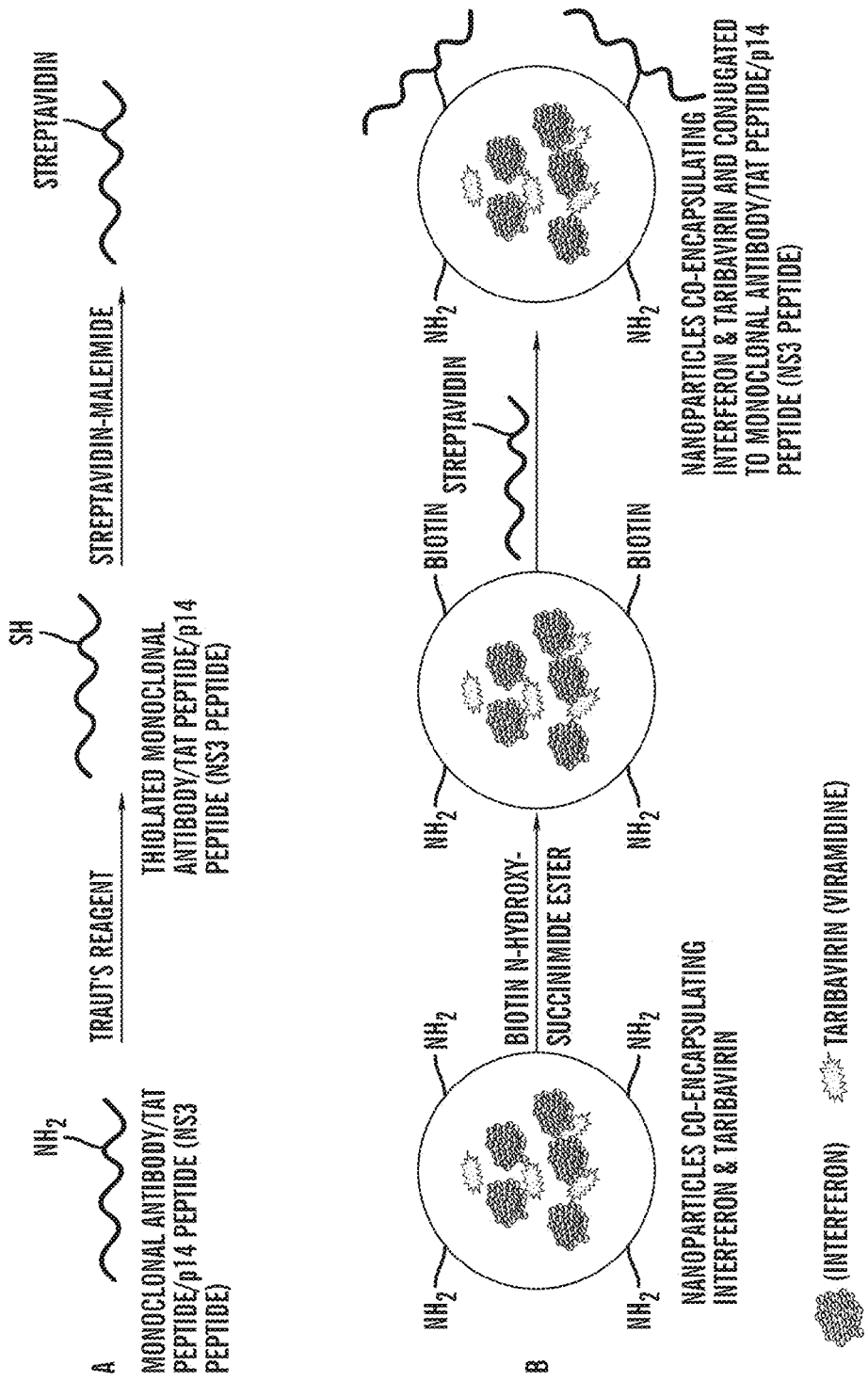
FIG. 3 depicts a schematic diagram showing conjugation strategy for linking monoclonal antibody/TAT Peptide/p14 peptide (NS3 peptide) nanoparticles, in accordance with embodiments of the present invention.
Figure 4:
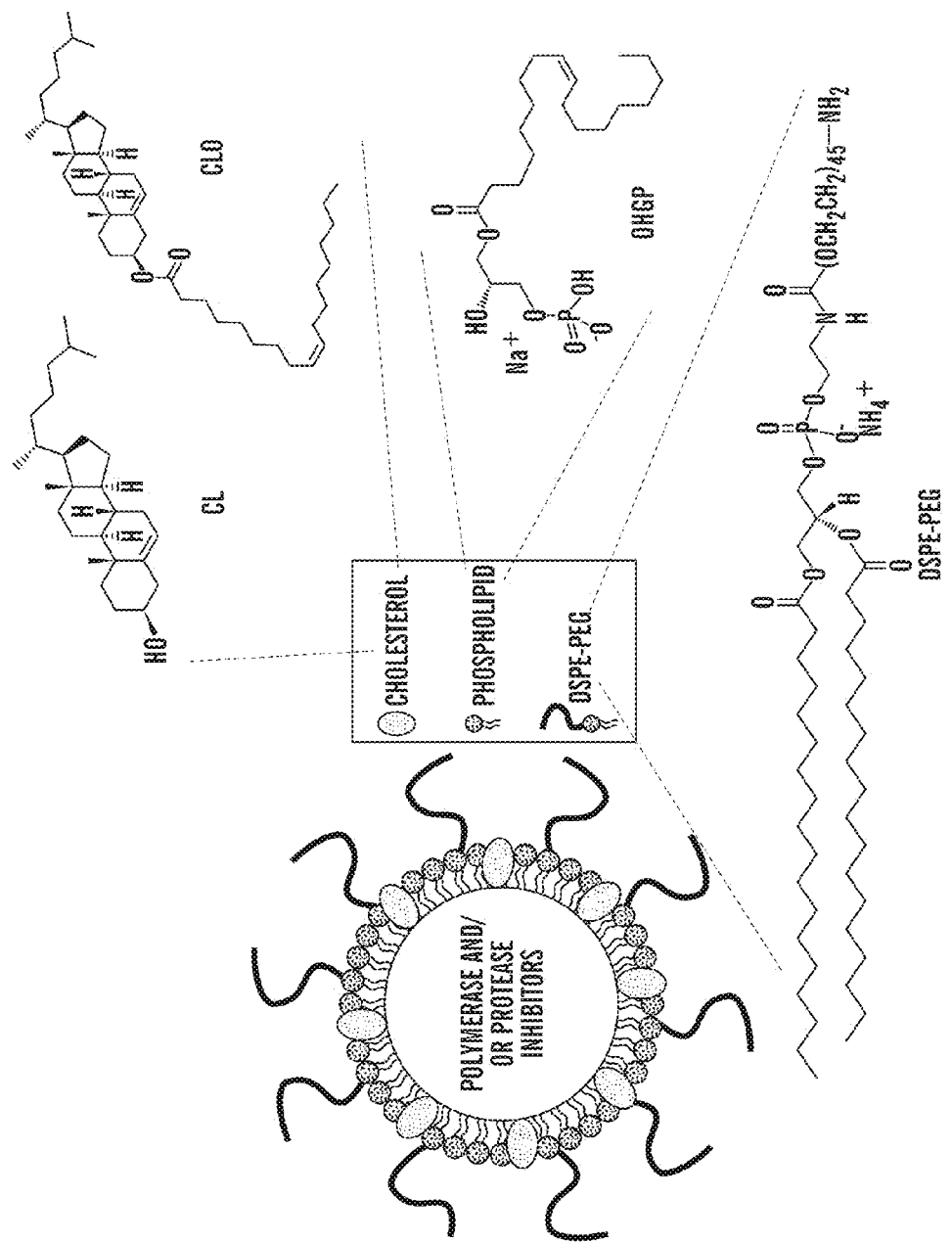
FIG. 4 depicts a sketch illustrating design of Solid Lipid Nanoparticles (SLN) for drug delivery wherein nanoformulations are synthesized for the encapsulation of antiviral polymerase and protease inhibitors containing anti-fibrotic/anti-hemolytic agents, and along with targeting for hepatic cells using Lactobionic acid, glycyrrhizin, and/or Galactosylated, in accordance with embodiments of the present invention.
Figure 5:
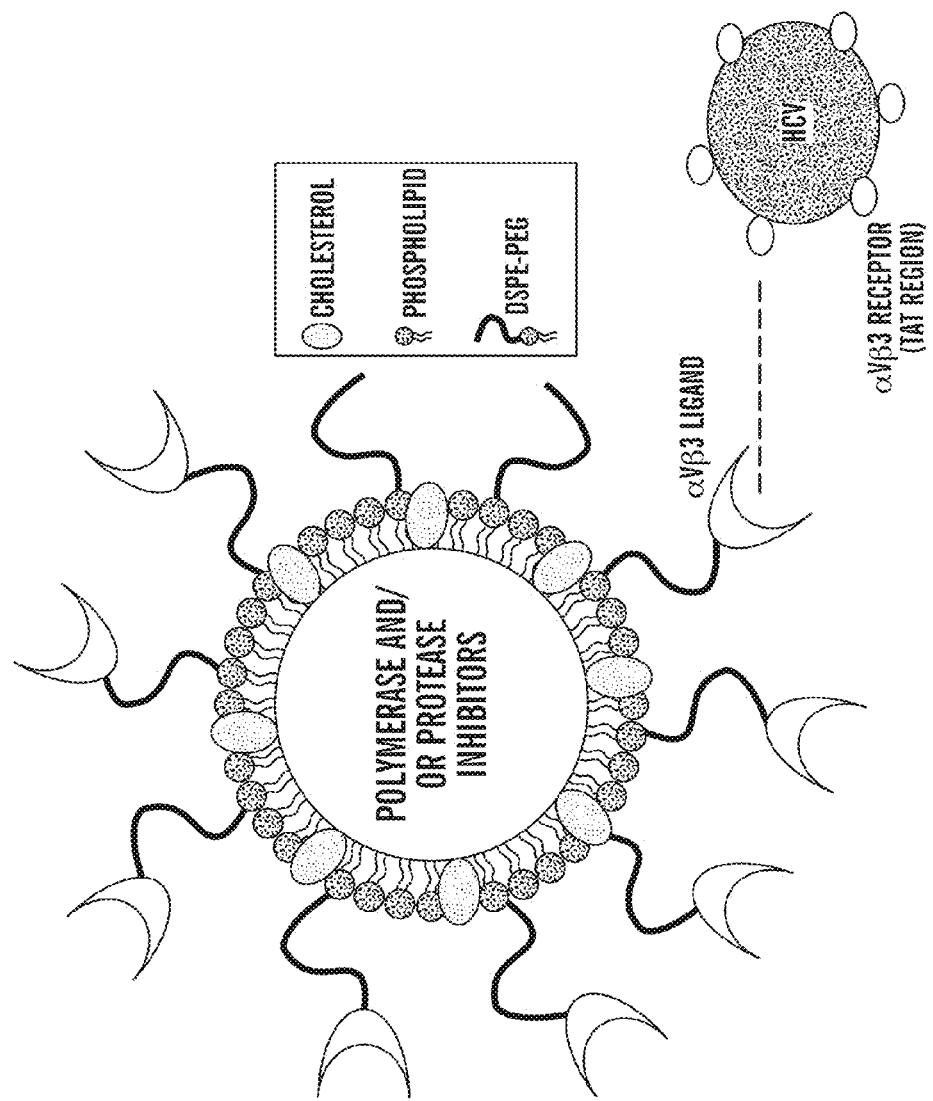
FIG. 5 depicts a sketch illustrating design of Solid lipid nanoparticles (SLN) for drug delivery wherein nanoformulations are synthesized for the encapsulation of polymerase and protease inhibitors containing viral entry inhibitors, anti-fibrotic agents, and along with targeting for hepatitis C virus which can be targeted by conjugation of high affinity αvβ3 ligand and coating/conjugation for hepatic cells using Lactobionic acid, glycyrrhizin, and/or Galactosylated, in accordance with embodiments of the present invention.
Figure 6:
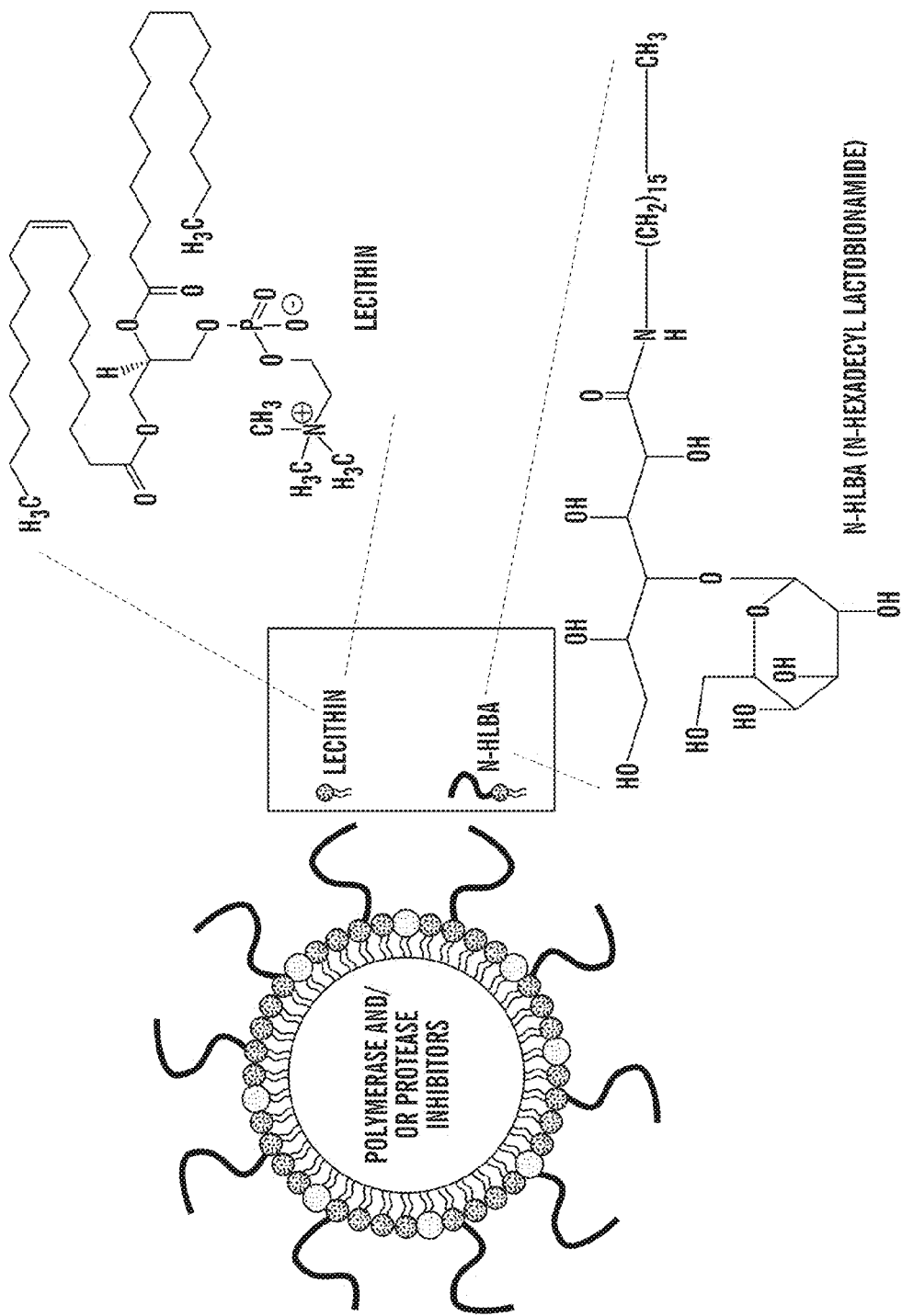
FIG. 6 depicts a sketch illustrating the design of nanoparticles for drug delivery wherein nanoformulations are synthesized for the encapsulation of antiviral polymerase and protease inhibitors containing viral entry inhibitors anti-fibrotic agents, and along with targeting for hepatic cells using coating/conjugation with Lactobionic acid, glycyrrhizin, and/or Galactosylated, in accordance with embodiments of the present invention.
Figure 7:
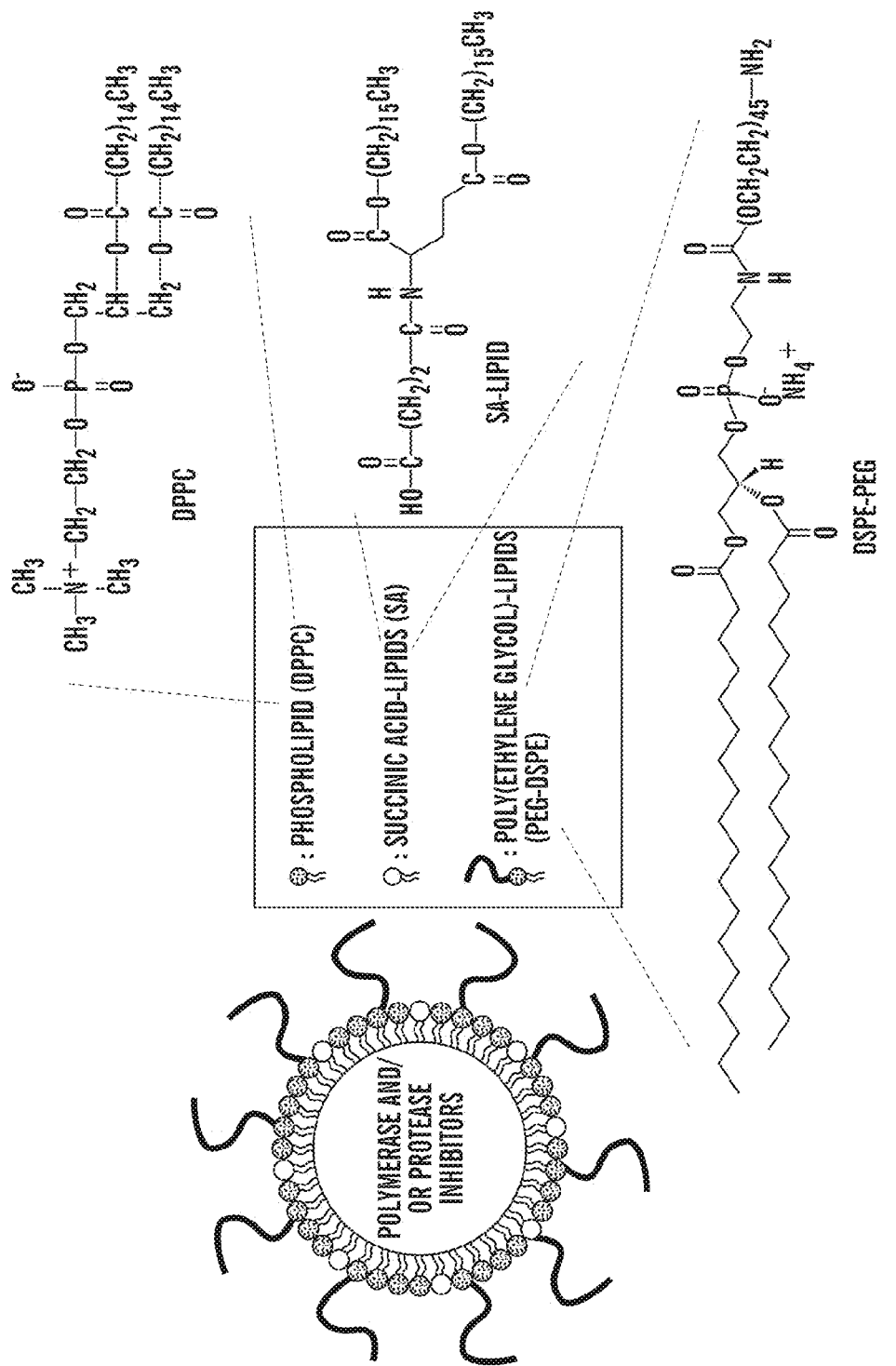
FIG. 7 depicts a sketch illustrating the design of nanoparticles for drug delivery wherein nanoformulations are synthesized for the encapsulation of antiviral polymerase and protease inhibitors containing viral entry inhibitors and anti-fibrotic agents along with targeting for hepatic cells using coating/conjugation with Lactobionic acid, glycyrrhizin, and/or Galactosylated, in accordance with embodiments of the present invention.

Conjugation of monoclonal antibody/TAT Peptide/p14 peptide (NS3 peptide): A schematic diagram of the nanoparticle conjugation scheme is shown in FIG. 3 which depicts a schematic diagram showing conjugation strategy for linking monoclonal antibody/TAT Peptide/p14 peptide (NS3 peptide) nanoparticles, in accordance with embodiments of the present invention. Surface functionalization and different conjugation chemistries were used to obtain nanoformulations co-encapsulating IFN and taribavirin, monoclonal antibody/TAT Peptide/p14 peptide (NS3 peptide).

Nanoparticles were conjugated monoclonal antibody/TAT Peptide/p14 peptide (NS3 peptide) using streptavidin/biotin chemistry. The three types of nanoparticles described above contain free amino groups on their surface. Thus, aminofunctionalized nanoparticles can be readily biotinylated using the appropriate amount of N-hydroxysuccinimidobiotin (Sigma-Aldrich, Saint Louis, Mo., USA) monoclonal antibody/TAT Peptide/p14 peptide (NS3 peptide) were first thiolated in side-by-side reactions using Traut's reagent (Pierce Biotechnology, Inc., Rockford, Ill., USA) (35-37), followed by the addition of streptavidin-maleimide (Sigma-Aldrich) to generate streptavidin-conjugated monoclonal antibody/TAT Peptide/p14 peptide (NS3 peptide) (FIG. 3). Thus, nanoparticles can be further subdivided into three different categories from each above mentioned type of nanoparticles (based on the targeted moiety). All the nanoformulations co-encapsulate IFN and taribavirin and A) Nanoformulation 1: conjugated to monoclonal antibody; B) Nanoformulation 2: conjugated to TAT Peptide and) Nanoformulation 3: conjugated to p14 peptide (NS3 peptide).

EXAMPLE 14

In vitro efficacy test: In vitro uptake were determined by confocal microscopy using dye-labeled nanoparticles. The human hepatocellular liver carcinoma cell line HepG2 was used, and all of the nanoparticle formulations described above were conjugated to Alexa Fluor 488. All of the nanoparticles contain a sufficient amount of free amino groups on their surface. Thus, the commercially available (Invitrogen Corp, Carlsbad, Calif., USA) Alexa Fluor 488

N-hydroxysuccinimide ester was used for conjugating the dye to the nanoparticles, according to the manufacturer's instructions.

EXAMPLE 15

Cell Culture: HepG2 cells were grown in Eagle's Minimum Essential Medium (EMEM) (Invitrogen, Grand Island, N.Y., USA) supplemented with 10% fetal calf serum (Atlanta Biologicals, Lawrenceville, Ga., USA). Penicillin/streptomycin (1%) was also present in the culture media (Invitrogen). The cells were trypsinized and collected by centrifugation, and then the cell pellet was resuspended in suitable media. An aliquot (1 mL) of the cell suspension was transferred to 35-mm glass-bottom culture dishes (MatTek Corp., Ashlan, Mass., USA) and the cells was allowed to incubate for 24 hours at 37° C. in a 5% $CO_2$ atmosphere (Thermo Electron Corp., Forma Series II).

EXAMPLE 16

Confocal Imaging: HepG2 cells were incubated with dye-labeled nanoparticles at 37° C., 5% $CO_2$ for pre-determined periods of time. After each specific time interval (1, 2, 4, and 6 hrs.), the plates were washed several times with PBS and then the cells were fixed in 1% formaldehyde (Sigma-Aldrich). Confocal images were taken using a Leica TCS SP5 confocal microscope equipped with a 63× objective (NA=1.3 glycerol immersion). Excitation was run at 405 nm and was detected between 508 nm and 530 nm. Based on the results obtained from size measurement, release kinetics, entrapment efficiency and confocal imaging, 2 nanoformulations from each category (3×3=9) were selected for further studies.

EXAMPLE 17

Cell cycle effect of the prepared compounds: HepG2 cells were washed twice in RPMI1640 (Cambrex) supplemented with 200 µM L-glutamine (Cambrex) and 25 µM HEPES buffer (Cambrex), and then suspended at a density of $2 \times 10^5$ cells/ml in RPMI culture media (RPMI supplemented with 10% FBS (Gibco-BRL/Invitrogen, Carlsbad, Calif., USA). Cells were allowed to adhere to 6-well polystyrene plates for 24 hours at 37° C. under 5% $CO_2$, 95% humidity. After 24 hours the cells were washed twice to remove debris and dead cells using RPMI supplemented media. Different concentrations (100, 50, 20, 10 or 5 µg/ml) of each prepared compound were added to the plates. Positive and negative control cultures were included. Cultures were incubated for 72 hours at 37° C., 5% $CO_2$, 95% humidity. To determine the effect of the compounds on the cell cycle, adherent control and treated cells were detached from the plate using 1 mL of trypsin: EDTA (200 mg/L EDTA, 500 mg/L trypsin; 1:250) for 1-3 minutes, and then trypsin was inhibited by the addition of 5 mL of RPMI culture media. The cells were scraped and collected in a 15 ml falcon tube, then washed twice using RPMI supplemented media, followed by washing once in PBS. After each wash, cells were collected by centrifugation at 1000 rpm for 5 minutes. Cells were resuspended in 1 ml of propidium iodide (PI; Sigma) (50 ml/L in 0.10% sodium citrate, 01% triton X-100), and then incubated in the dark at 4° C. for at least 60 minutes. The cell cycle effect of the compounds on HepG2 cells were examined by FACS Calibur flow cytometry (BD Bioscience, San Diego, Calif., USA) and data were analyzed using MOD Fit (BD Bioscience).

EXAMPLE 18

Qualitative in vitro anti-HCV screening: Compounds were investigated for their activity in vitro as anti-HCV agents using HepG2 cells infected with HCV. Among several human hepatocyte cell lines analyzed, HepG2 cells found to be the most susceptible to HCV infection. Detection of positive (+) and/or negative (−) viral RNA strands by qualitative reverse transcription-polymerase chain reaction (RT-PCR) has become the most frequently-used, reliable and sensitive technique for monitoring HCV viremia pre- and post-antiviral therapy. Recently, it was shown that detection of (−) strand HCV mRNA using RT-PCR is a very important tool for understanding the life cycle of HCV, and provides a reliable marker for the diagnosis of HCV and for monitoring viral response to antiviral therapy. The method adopted for the current study allows for simultaneous detection of (+) and/or (−) strand HCV mRNA in HepG2 cells infected with HCV. Viral replication were detected by amplification of specific viral RNA segments using RT-PCR from cells cultivated alone (as a positive control) and in the presence of variable concentrations of test compound at optimal temperature. The test compound was considered active when the test compound is capable of inhibiting viral replication in HCV-infected HepG2 cells, as evidenced by the disappearance of amplified (+) and/or (−) strand viral mRNA products (as compared to the positive control). Using the same method, HCV replication was examined in peripheral blood cells isolated from 10-20 HCV-infected patients before and after the cells are cultured in vitro in the presence of different concentrations of prepared compounds.

EXAMPLE 19

Flow cytometry analysis of intracellular HCV core antigen in infected HepG2 cells: The presence of intracellular HCV core antigen in HCV infected HepG2 cells were quantified before and after incubation with different concentrations of test compounds using fluorescence activated cell sorting (FACS). Intracellular localization of HCV core antigen was carried out using direct immunofluorescence staining. HepG2 cells (after trypsinization) were collected by centrifugation, and the supernatants were removed. Cell pellets were washed 4 times with PBS. For intracellular staining, cells were incubated in 4% paraformaldehyde for 10 minutes, followed by 0.1% Triton X-100 in Tris buffer (pH 7.4) for 6 minutes. After washing with PBS, cells were incubated with FITC-labeled anti-HCV core antibody (F (ab)2 portion; 1:2000 dilution, or as determined by prior standardization) for 30 minutes at 4° C. Cells were washed with PBS containing 1% normal goat serum, resuspended in 500 µL, and then analyzed by flow cytometry (FACS Calibur, BD). Mean fluorescence intensity were determined using Cell Quest software (Becton Dickinson).

The immunodeficient uPA mouse model were used to determine the in vivo efficacy of nanoformulations incorporating IFN and taribavarin. The uPA/SCID mouse model is one of the models most closely related to human physiology, as the humanized liver contains as high as 75% human hepatocytes. Thus, this model has tremendous potential to serve as a bridge between the in vitro work and clinical research.

EXAMPLE 20

Chimeric uPA-SCID mice engrafted with human hepatocytes were used to determine the in vivo efficacy of selected nanoformulations. The uPA-SCID mice engrafted with human hepatocytes were generated. Mice were maintained in a barrier facility in HEPA-filtered racks. The animals were fed a sterilized laboratory rodent diet.

Treatments: Mice that are infected with HCV were treated with the best from the nanoformulation chosen from each category of the nanoformulation 1, 2 or 3 or controls (see below), by intraperitoneal injection of the optimum dose every other day for 14 days. To determine anti-HCV efficacy, a pilot study was performed to determine the optimum dose needed in the mouse model. Blood samples were collected from the tail vein in every other day for 10 days after the conclusion of treatment.

HCV viremia in the blood samples before and after administration of nanoformulations (or controls) were monitored by detection of (+) and/or (−) viral mRNA using RT-PCR.

EXAMPLE 21

Statistical analysis: Values were computed for individual animals and for groups of animals, and differences between groups were analyzed using the Student's t-test or Mann Whitney-U test based on the distribution of data. Mean values for each treatment group were derived by combining single experimental values for each animal within the group. ANOVA were used to test differences among several treatment group means. A P value <0.05 was considered statistically significant.

In vitro and in vivo studies identified 2'-C methylcytidine prodrugs of a polymerase inhibitor that could help treat HCV. In cell-based assays, the prodrugs inhibited HCV NS5B polymerase with 10- to 200-fold better potency than the parent compound. In hamsters and rats, subcutaneous administration of the prodrug led to accumulation of the active compound in the liver without the generation of toxic metabolites.

EXAMPLE 22

Galactosylated Solid Lipid Nanoparticles (SLN): Preparations (1): 100 mg Lactobionic acid calcium salt/5 ml D.D.$H_2O$, 150 mg N-Hydroxysuccinimide (NHS), 150 mg N-(3-Dimethyl amino propyl)-N'-ethyl-carbodiimide hydrochloride, Mixing them together and stirring were done for 1 hr. and then 100 mg Hexadecylamine was added. Preparations (II): 1.5 g Lecithin, 10 ml Pluronic F68, 5 ml Tween 80, Mix and complete them to 100 ml DD.$H_2O$, and Stirring for 72 hrs.

Figure 16:
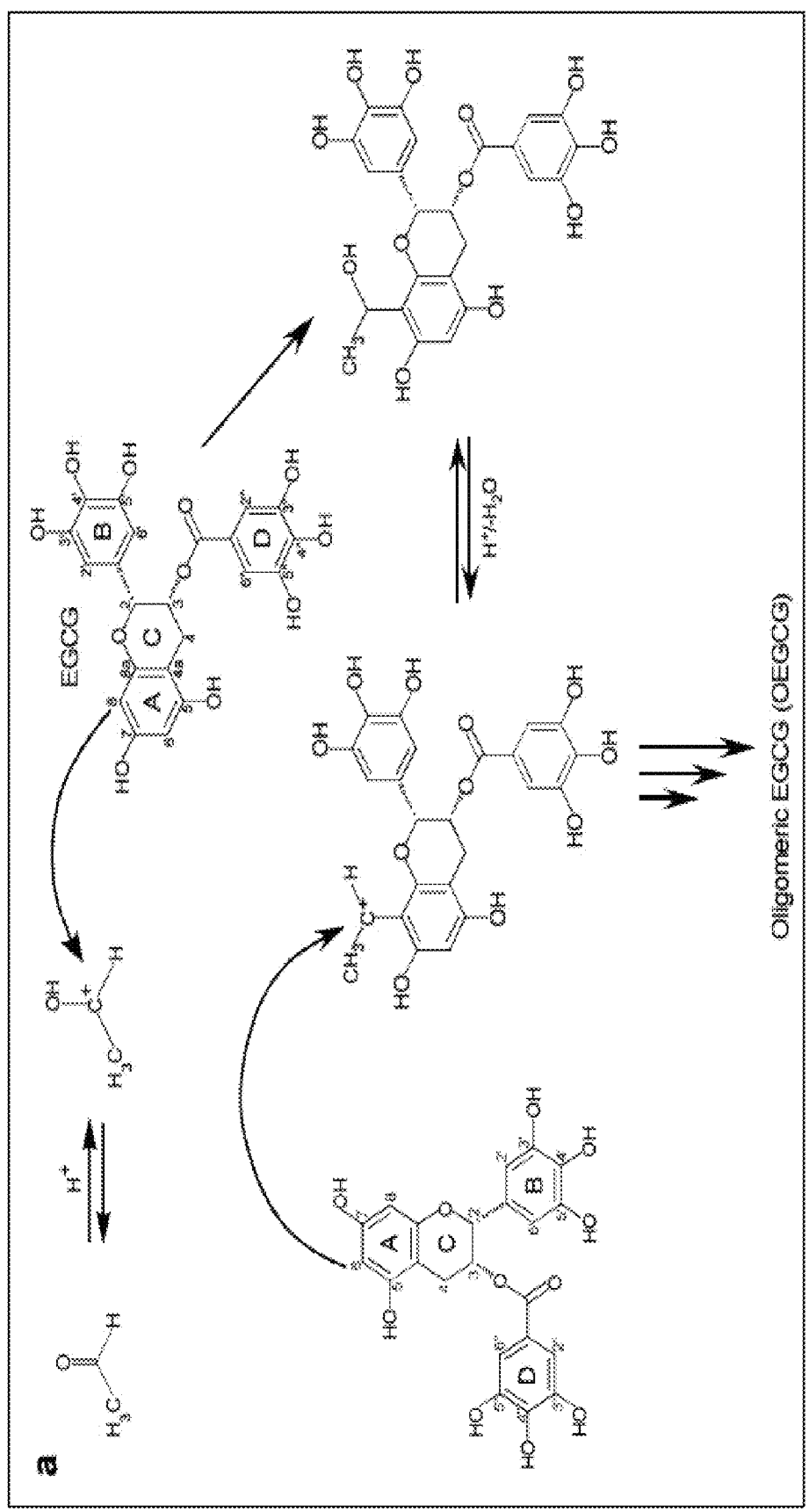

FIG. 16: depicts the chemical structure and schematic illustration of OEGCG synthesized from the intermolecular poly condensation reaction of epigallocatechin gallate (EGCG), in accordance with embodiments of the present invention.

Synthesis of oligomerized EGCG: EGCG (0.65 mmol) was first dissolved in 3 mL of DMSO and 10 mL of water. Then 0.84 mL of acetic acid and 0.14 mL of 1 mol/L HCl was added to lower the pH of the solution from 7 to 2. Acetaldehyde (2.4 mL, 40 mmol) was added drop wise under regular stirring. The mixture was degassed under vacuum for 10 min and then filled with nitrogen. The reaction mixture was stirred for 48 h at 20° C. under nitrogen. Afterwards the solution was dialyzed to remove free EGCG. The oligomerized EGCG (OEGCG) was collected and lyophilized.

Figure 17:
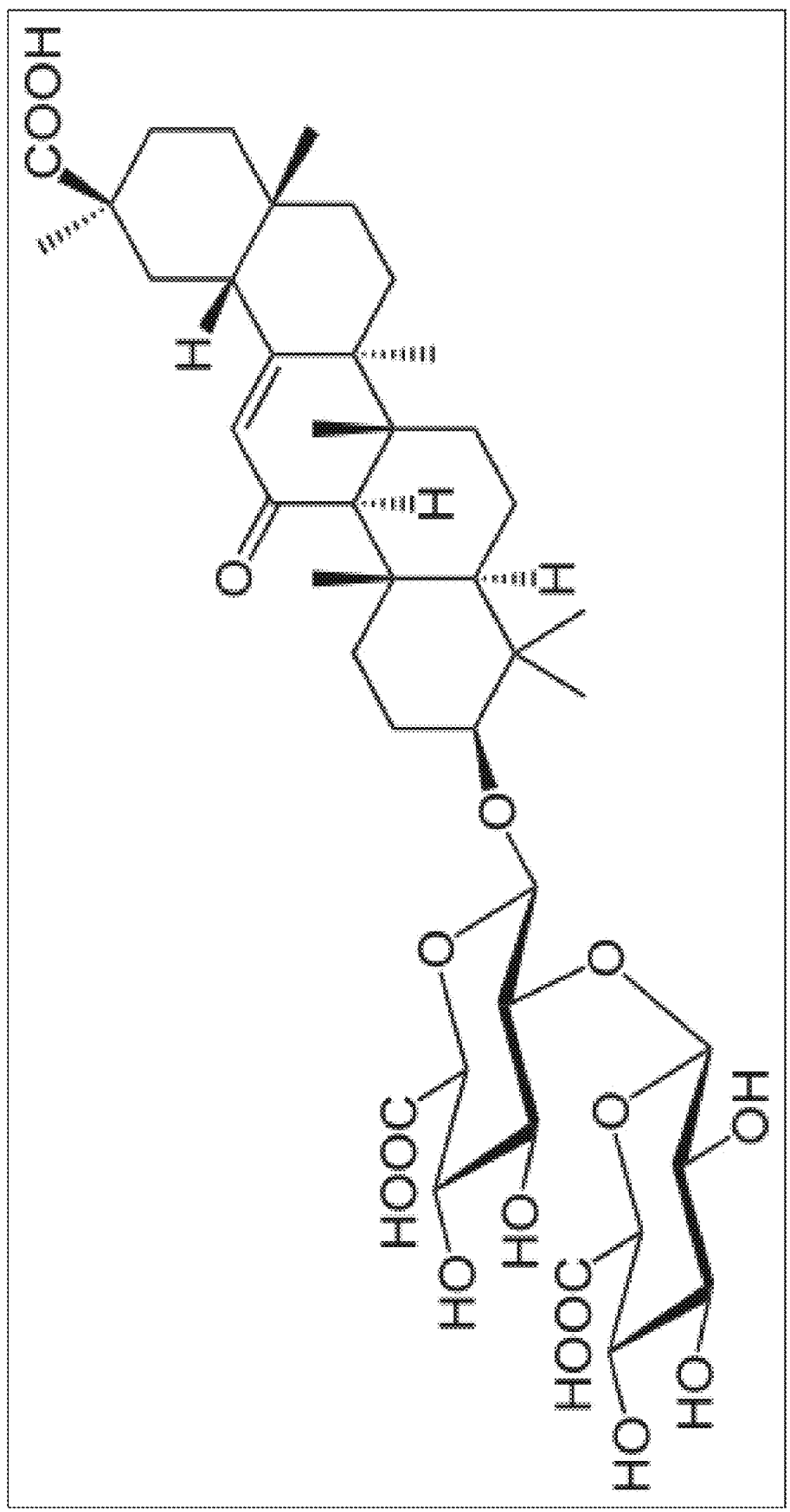

FIG. 17 depicts the conjugation of Oligomer EGCG to Glycyrrhetinic acid, in accordance with embodiments of the present invention.

Figure 18:
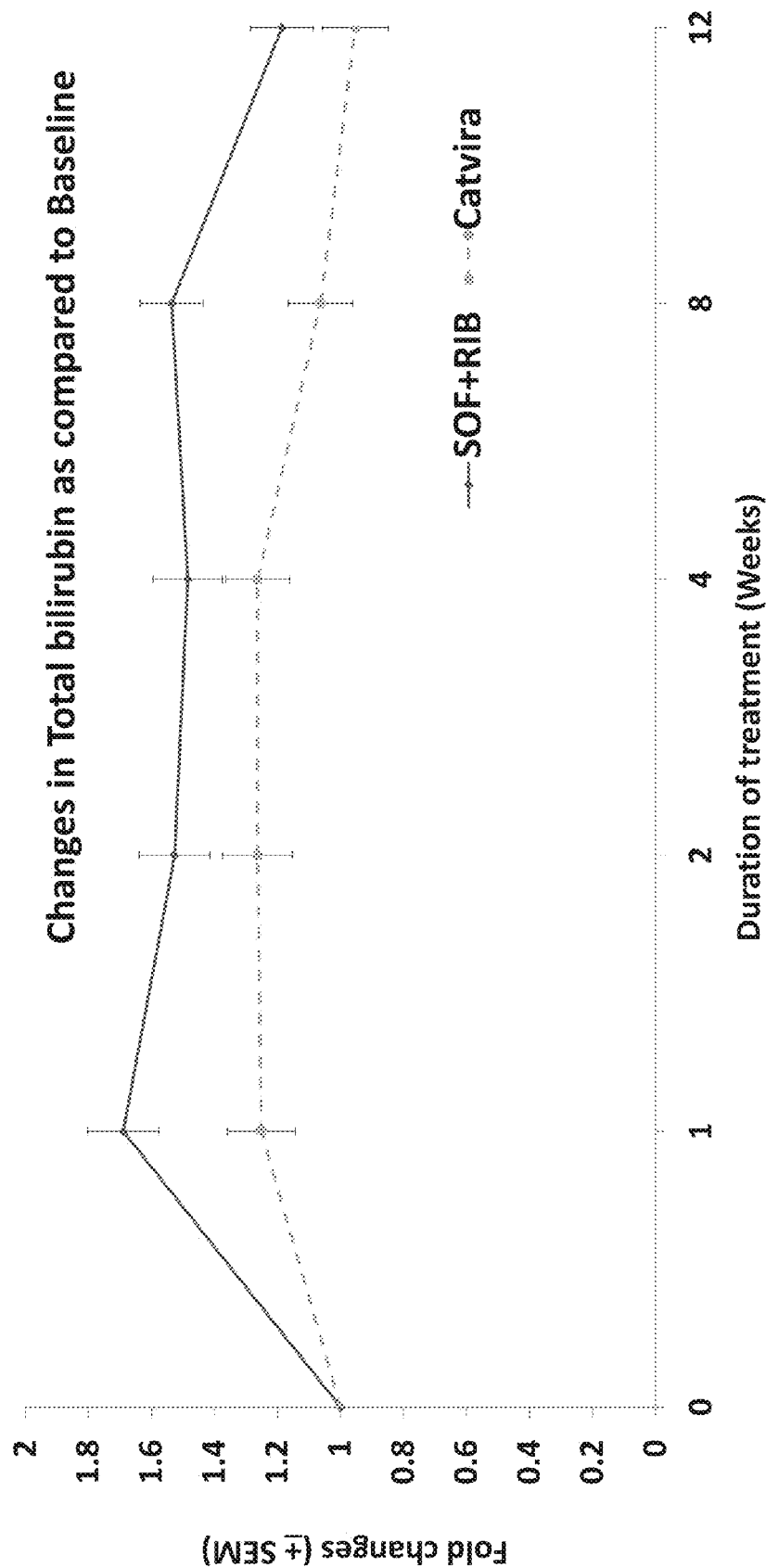

FIG. 18 depicts the fold changes in total Bilirubin relative to the base line in the SOF+Rib arm of the trial versus Catvira arm after 12 weeks of treatment in naïve HCV patients, in accordance with embodiments of the present invention.

Figure 19:
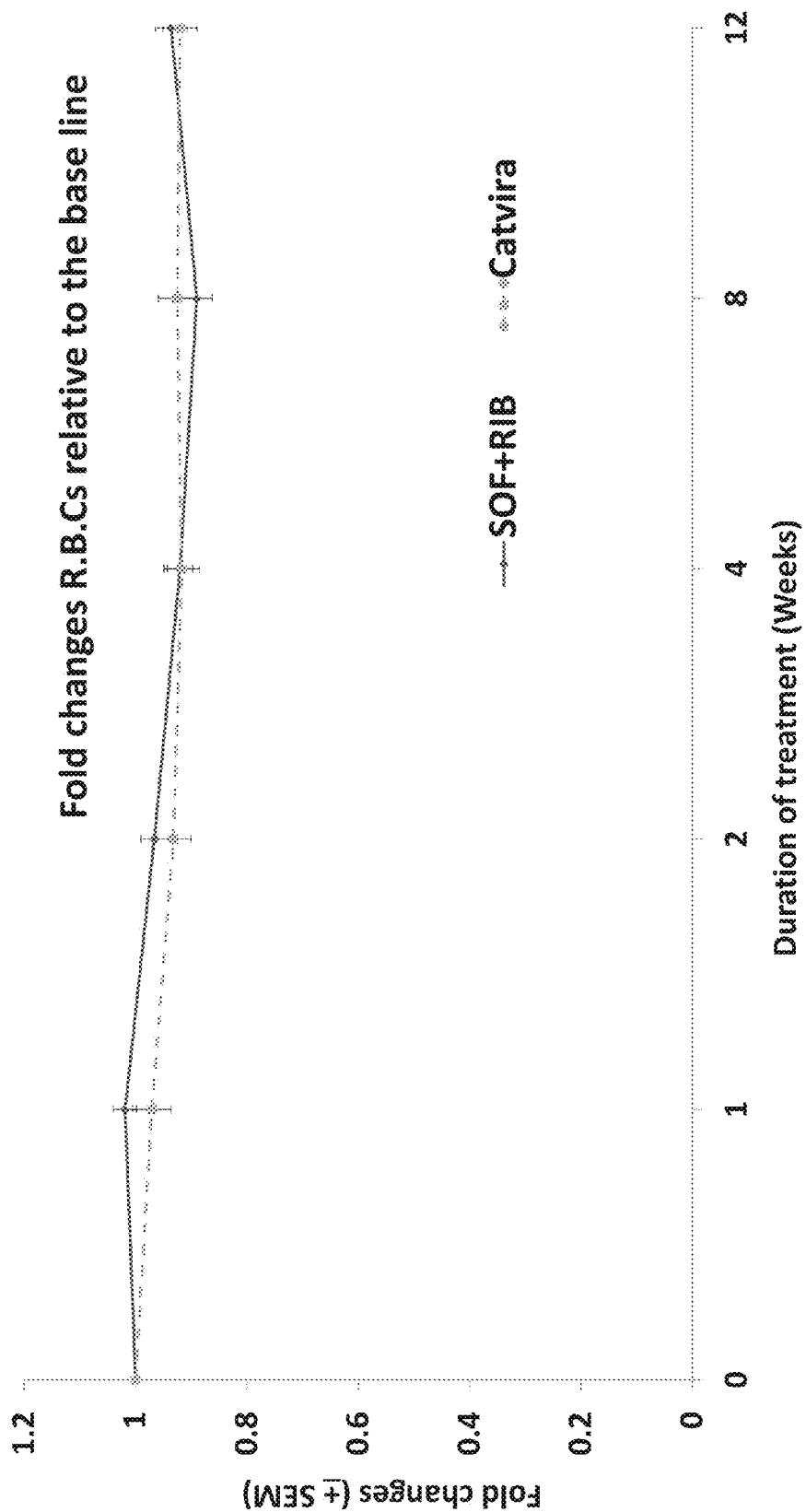

FIG. 19 depicts the fold changes in Red Blood Cells (RBCs) count relative to base line in the SOF+Rib arm of the trial versus Catvira arm after 12 weeks of treatment in naïve HCV patients, in accordance with embodiments of the present invention.

Figure 20:
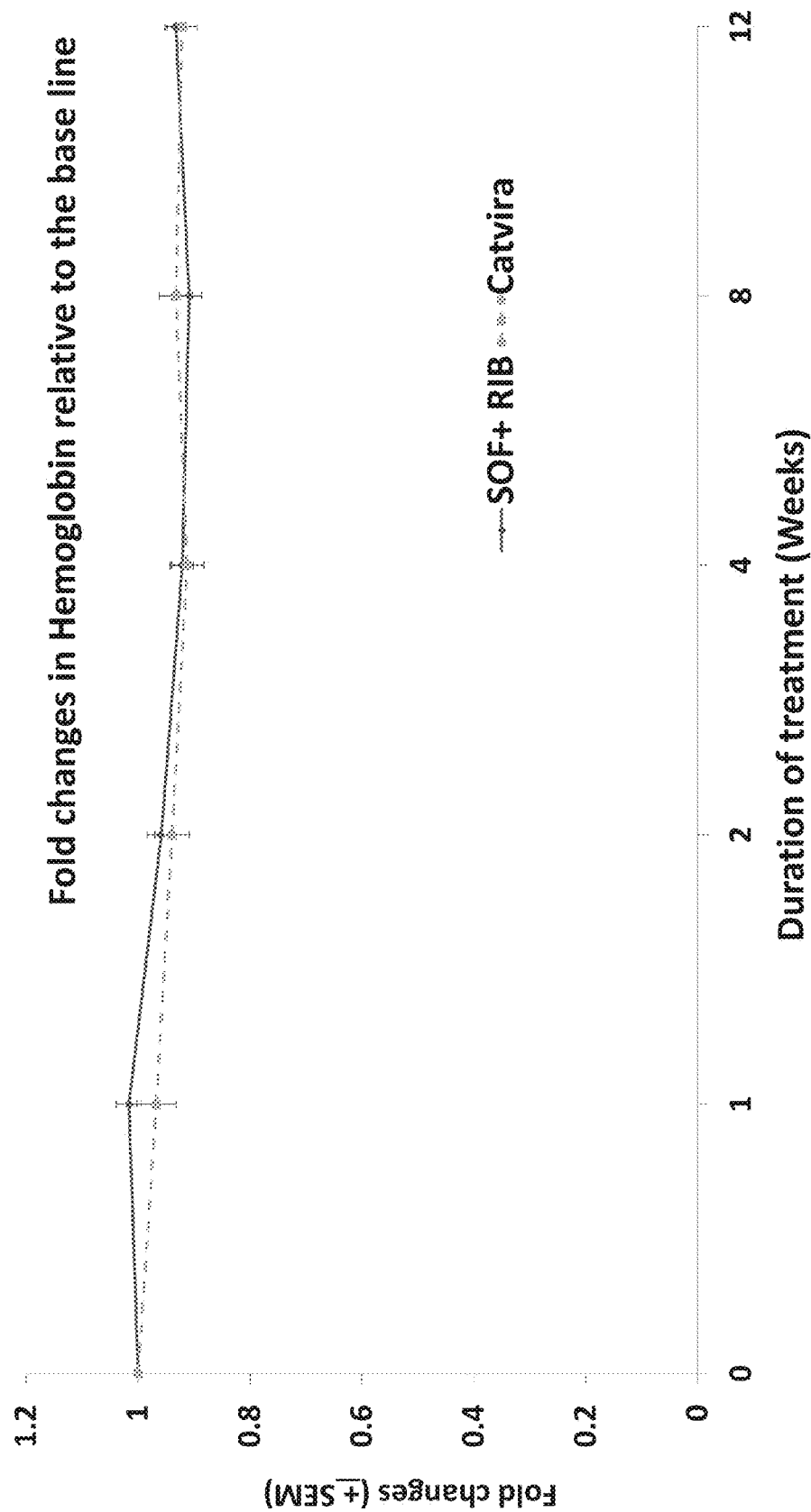

FIG. 20 depicts the fold changes in hemoglobin relative to base line in SOF+Rib arm of the trial versus Catvira arm after 12 weeks of treatment in naïve HCV patients, in accordance with embodiments of the present invention.

Figure 21:
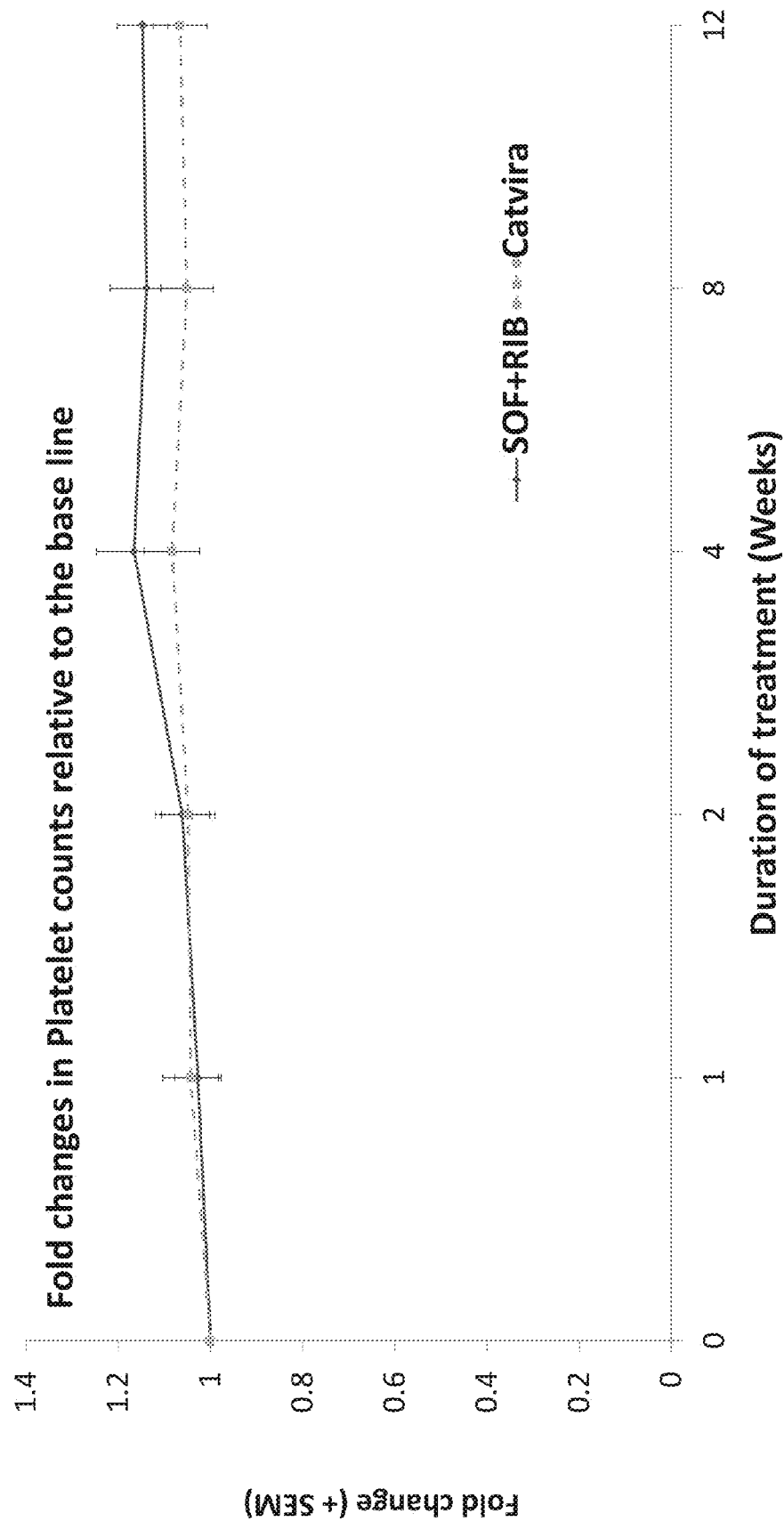

FIG. 21 depicts the fold changes in Platelet count relative to base line in SOF+Rib arm of the trial versus Catvira arm after 12 weeks of treatment in naïve HCV patients, in accordance with embodiments of the present invention.

Figure 22:
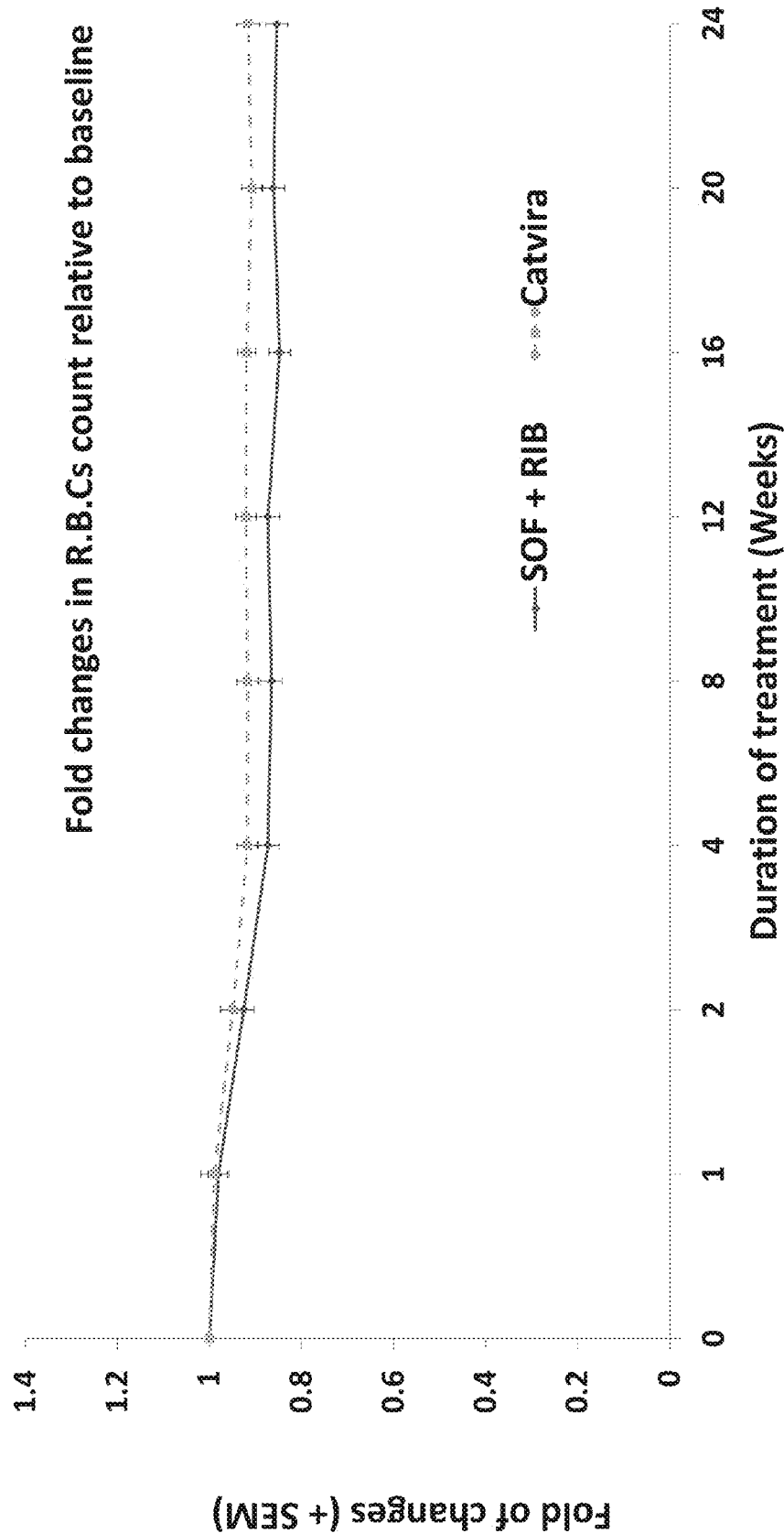

FIG. 22 depicts the fold changes in Red Blood Cells (RBCs) count relative to base line in the SOF+Rib arm of the trial versus the Catvira arm after 24 weeks of treatment in experienced (previously treated) HCV patients, in accordance with embodiments of the present invention. The data shows significant trend for improved RBCs count in the Catvira arm vs. SOF+Rib arm.

Figure 23:
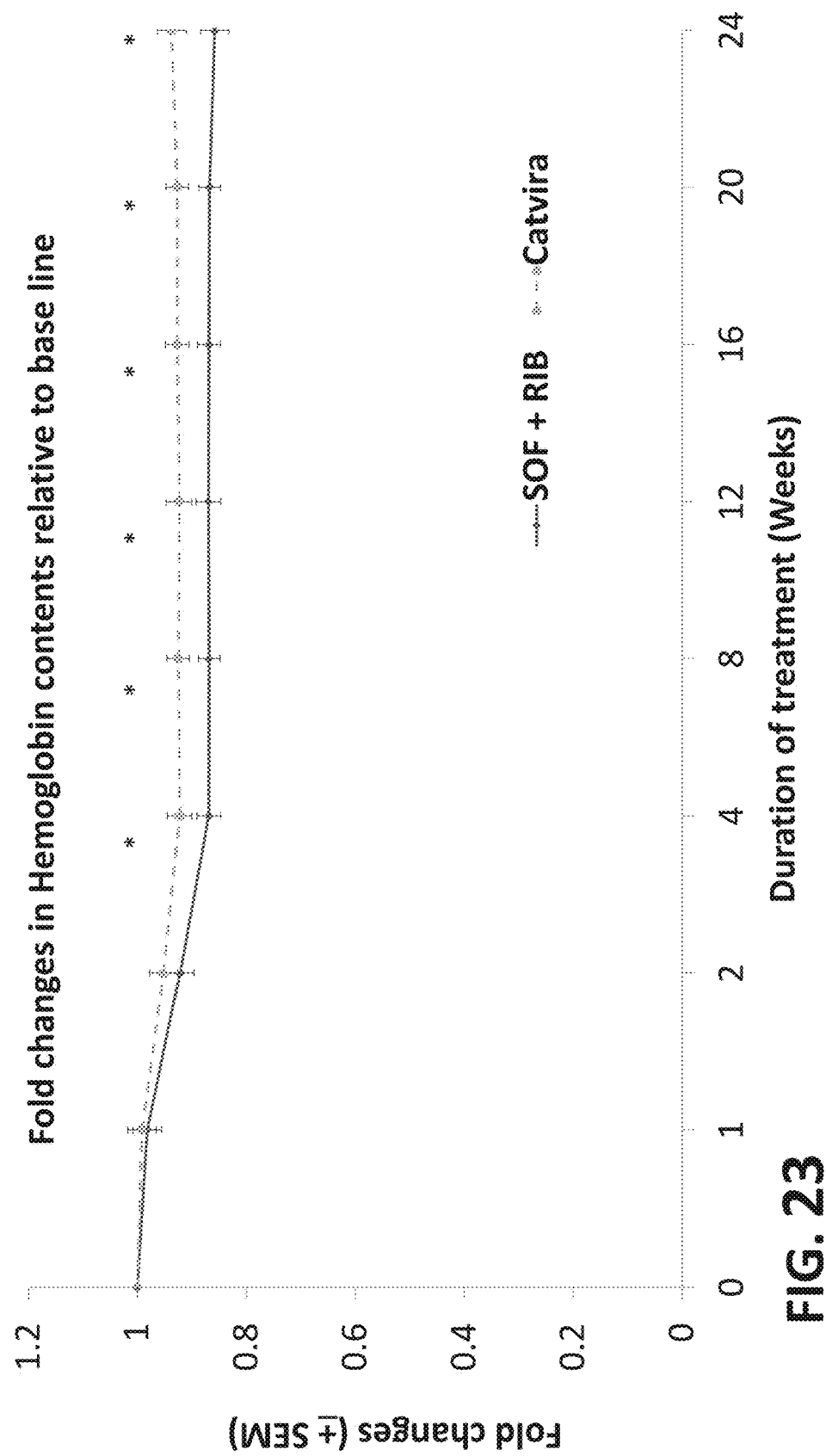

FIG. 23 depicts the Fold Changes in Hemoglobin relative to base line in the SOF+Rib arm of the trial versus the Catvira arm after 24 weeks of treatment in experienced (previously treated) HCV patients, in accordance with embodiments of the present invention. The data showed statistically significant trend for improved Hemoglobin in the Catvira arm vs. SOF+Rib arm, * P<0.05.

EXAMPLE 23

Clinical Study: The standard of care until 2011 was restricted to the combination of injectable pegylated interferon-a (PEG IFN-a) and oral ribavirin, which showed limited sustained viral response, poor tolerability and differential success rates dependant on infecting viral genotype. The emergence of new molecules act directly on the virus itself such as anti-HCV polymerase sofosbuvir improved the treatment regimens. In addition to the extremely high cost of this therapy there is also a risk of selecting viral escape mutants so a new combination is needed that, ideally, should include inhibitors targeting different steps of the HCV infectious cycle, entry, replication, and assembly/secretion, and should be efficient against all HCV genotypes. Therefore, the development of novel, inexpensive, better-tolerated, and more-effective anti-HCV agents is urgently needed.

The efficacy and safety of the new drug a fixed dose tablet (Catvira) in relation to the standard of care (sofosbuvir+ribavirin) multiple tablets per day was evaluated in HCV Egyptian patients (genotype 4). Each Catvira contains 400 mg of sofosbuvir, 1000 mg Ribavirin and 400 mg NBI (EGCG) plus 200 mg excipients and coating per 2 tablets.

EXAMPLE 24

Methods: Treatment-naïve or treatment-experienced patients with genotype 4 HCV infection (n=81) were randomly assigned to receive either 12 or 24 weeks of single fixed dose of Catvira (400 mg sofosbuvir+1000 mg ribavirin+400 mg EGCG+exceipients) versus the standard of care sofosbuvir at 400 mg tablet per day and ribavirin at 1000 mg multiple tablets pe day. Randomization was stratified by prior treatment experience and by presence or absence of cirrhosis. The primary endpoint was the percentage of patients with HCV RNA and safety profiles.

Results: Catvira for 12 or 24 weeks is effective and safe in either naïve or treatment experienced Egyptian patients with genotype 4 HCV. Catvira showed comparable results to the standard of care but with faster and sustained viral response along with noticable reducation of adverse events.

The following description of a clinical study utilized an embodiment of the composition of the present invention.

The novel composition was given the name Catvira composed of Sofosbuvir/Ribavirin/NBI tablets (2 tablets) or one chewable tablet for oral administration. Each tablet contains 400 mg of sofosbuvir, 1000 mg Ribavirin and 400 mg NBI (EGCG). The tablets include the following inactive ingredients: magnesium stearate, mannitol, and microcrystalline cellulose. The Catvira tablets are film-coated with a coating material containing the following inactive ingredients: polyethylene glycol, polyvinyl alcohol, and yellow iron oxide.

NBI prevent the complications associated with Ribavirin: Patients with certain types of heart disease should not use ribavirin because it can lower a patient's red blood cell level (anemia). Ribavirin may worsen the patient's condition and can lead to a possibly fatal heart attack. Additionally, the used polyphenol EGCG from the Catchin family effectively suppressed HCV viral entry into human host cells, which is critical in the prevention of relapse.

EXAMPLE 25

Each tablet of Catvira, a chewable tablet (2.0 grams each) or 1.0 gram (2 tablets), contain: 1000 mg. Ribavirin+400 mg Sofosbuvir+400 mg. EGCG+200 mg. Excipients (Table 1-5). Natural Bioactive ingredients (NBI) prevented HCV viral entry into human host cell, prevented ribavirin-mediated anemia and reduced hepatic fibrosis, which is a major improvement than the current medicine, and the excipients to be added for taste and cohesiveness of the tablet. Additionally, data unexpectedly showed an enhanced anti-viral response within the first two weeks after treatment as compared to the standard of care (using 400 mg Sofosbuvir, along with multiple tablets of Ribavirin, totaling 1000 mg/subject per day).

TABLE 1

Each Catvira film coated tablet contains:

| No. | Ingredient Name | Quantity/tablet | specification |
|---|---|---|---|
| Active ingredient | | | |
| 1 | Sofosbuvir | 200 mg | In house specs |
| 2 | Ribavirin | 500 mg | USP36/NF 30 |
| 3 | Epigallocatechin gallate | 200 mg | USP36/NF 30 |
| Inactive ingredient | | | |
| 4 | Avicel ph102 | 20 mg | USP36/NF 30 |
| 5 | Croscarmellose sodium | 50 mg | USP36/NF 30 |
| 5 | Aerosil 200 | 10 mg | USP36/NF 30 |
| 6 | Magnesium stearate | 10 mg | USP36/NF 30 |
| Composition of coat | | | |
| 7 | Opadry AMP II | 10 mg | In house specs |

EXAMPLE 26

TABLE 2

| Specifications | |
|---|---|
| Items | Limits |
| Appearance | Film coat tablet |
| Color | Yellow to deep yellow |
| Average weight of a tablet | (950-1050) mg |
| Hardness | (NLT4 Kp) |
| Dissolution | NTL 70% |
| Content uniformity | Meets USP requirement |
| Identification for: | Positive |
| Sofosbuvir | |
| Ribavirin | |
| Epigallocatechin gallate | |
| Assay for: | (90-110) % Labeled amount |
| Sofosbuvir | |
| Ribavirin | |
| Epigallocatechin gallate | |

EXAMPLE 27

TABLE 3

Manufacturing Formula

| No. | Ingredient Name | Quantity/tablet | specification | Quantity/ 3000 tablets |
|---|---|---|---|---|
| Active ingredient | | | | |
| 1. | Sofosbuvir | 200 mg | In house spec | 600 gm |
| 2. | Ribavirin | 500 mg | USP36/NF30 | 1.5 kg |
| 3. | Epigallocatechin gallate | 200 mg | USP36/NF30 | 600 gm |
| Inactive ingredient | | | | |
| 4. | Avicel ph102 | 20 mg | USP36/NF30 | 60 gm |
| 5. | Croscarmellose sodium | 50 mg | USP36/NF30 | 150 gm |
| 6. | Aerosil 200 | 10 mg | USP36/NF30 | 30 gm |
| 7. | Magnesium stearate | 10 mg | USP36/NF30 | 30 gm |
| Composition of coat | | | | |
| | Opadry AMP II | 10 mg | In house spec | 30 gm |

EXAMPLE 28

TABLE 4

List of Equipment

| Equipment |
|---|
| Dispensing booth |
| Weighing balance |
| Single cone mixer |
| Stirrer with S.S. Vessel |
| Sifter |
| Granulating machine |
| Dryer or fluid bed dryer |
| Multi mill |
| Compression machine |
| Tablet hardness tester |
| Friability tester |
| Disintegration test apparatus |
| Coating pan |
| Strip packing machine |

EXAMPLE 29

TABLE 5

| Time (min) | Ribavirin | | | Sofosbuvir | | |
|---|---|---|---|---|---|---|
| | pH 1.2 | pH 4.5 | pH 6.8 | pH 1.2 | pH 4.5 | pH 6.8 |
| 5 | 25.34% | 29.46% | 59.24% | 13.82% | 15.00% | 36.18% |
| 10 | 43.13% | 47.54% | 76.73% | 28.77% | 33.94% | 65.56% |
| 15 | 62.29% | 68.75% | 88.40% | 44.57% | 52.46% | 83.04% |
| 20 | 80.69% | 85.33% | 92.31% | 63.43% | 74.22% | 97.55% |
| 30 | 100.74% | 101.35% | 93.23% | 85.39% | 98.95% | 99.80% |
| 45 | 101.36% | 101.42% | 93.09% | 86.07% | 100.44% | 100.04% |
| 60 | 101.87% | 102.72% | 93.31% | 88.13% | 101.08% | 100.47% |
| 90 | 101.97% | 102.97% | 94.02% | 90.79% | 102.04% | 100.39% |

Dissolution time Interval

EXAMPLE 30

Manufacturing Processing Instruction
1) Precautions:
1.1—the working area and all equipment required should be cleaned before starting the manufacturing process.
1.2—Be sure that a clean label signed by QA is present.
1.3—the operator and checker must be sign initial where each step.
1.4—the labels for the used raw materials must be removed and stacked to the back of the production batch.
1.5—the in process sheets are integral part of the record.
1.6—Workers must wear gloves and masks during the production.
1.7—All process must be protect from light.
1.8—Relative humidity must be less than 50%.

EXAMPLE 31

2) Manufacturing Process
1) Dispensing
a) Ensure the dispensing and line clearance as per the standard operating procedure.
b) Dispense the required quantity of approved raw material under dispensing laminar air flow.
c) Collect the weighed raw material to clean double poly bag and label all of products.
d) Cross check the weighted raw material on a calibrated balance and record the gross weight.
2) Sofosbuvir Solution
Ensure the line clearance of the stales steel vessel then add 200 ml isopropanol then dissolve sofosbuvir and continue stirring to get clear solution.
3) Solid Dispersion Method
a) Check the line clearance for dispersion.
b) Installs steel tray dispersion for sofosbuvir solution on ribavirin raw material for granulation.
c) Place in drying in oven at 40 degree C. moisture.
4) Milling and Sieving
After drying, make milling for granular powder on Fitz mill; then make sieving for milled powder with Epigallocatechin gallate, Avicel ph 102, Croscarmellose and Aerosil 200; then make mixing for powder in single con mixer.
5) Lubrication:
In single container add magnesium stearate then do final mixing.

6) Compression
a) Ensure line clearance for compression after checking all the parameters transfer the approved blended material into the tablet compression room for compression.
b) Carry out compression using suitable machine with oblong punches.
c) Transfer the blended material into the hopper and compress the powder into tablet by operating tablet compression machines.
d) Set the machine and adjust the parameters to obtain the following specification

EXAMPLE 32

TABLE 6

Tablet Core Specification

| Items | Limits |
|---|---|
| Appearance | Oblong tablets |
| Color | White to off white tablet |
| Average weight of a tablet | (940.5-1039.5) mg |
| Hardness | (NLT4 Kp) |
| Friability | N.M.T 1% |
| Dissolution | N.L.T 70% |
| Content uniformity | Meets USP requirement |
| Identification for: | Positive |
| Sofosbuvir | |
| Ribavirin | |
| Epigallocatechin gallate | |
| Assay for: | 90-110 Labeled amount |
| Sofosbuvir | |
| Ribavirin | |
| Epigallocatechin gallate | |

Checks for weight variation, hardness, friability, and thickness to meet the parameter, collect the tablet into a clean double poly bag. Then place label in between the two poly bags indicating the product name, cross weight, and net weight and record the room temperature and relative humidity. Submit 75 compressed tablet from the containers to QC for analysis.

EXAMPLE 33

5) Coating
a) Stir 1 liter purified water in a vessel to form vortex without drawing air into liquid. Disperse opadry AMP II by using stirrer and then pass mixture through colloidal mill.
b) Coat the core tablet in the coating pan.
c) 2% of initial tablet weight gain during the process of coating using the following specification.
1—Pan with baffles
2—Pan R.P.M: 6 to 8
3—Inlet temperature: 50° C. to 60° C.
4—Outlet temperature: 45° C. to 55° C.
5—Air pressure: 4 Kg/Cm$^2$ to 5 Kg/Cm$^2$
d) Visual checking and collect the tablet into a clean double poly bag. Place label in between the two poly bags indicating the product name, cross weight, and net weight

EXAMPLE 34

Storage
Store at 25° C. (77° F.); excursions permitted to 15-30° C. (59-86° F.) [see USP Controlled Room Temperature]. Keep container tightly closed.

TABLE 7

Finish Product specification

| Items | Limits |
|---|---|
| Appearance | Film coat tablet |
| Color | Yellow to deep yellow tablet |
| Average weight of a tablet | (950-1050) mg |
| Hardness | NUT 4 Kp |
| Friability | Not More Than. 1% |
| Dissolution | Not Less Than 70% is dissolved in 30 min. |
| Disintegration time | NMT 30 minutes |
| Content uniformity | Meets USP requirement |
| Identification for: | Positive |
| Sofosbuvir | |
| Ribavirin | |
| Epigallocatechin gallate | |
| Assay for: | 90-110 Labeled amount |
| Sofosbuvir | |
| Ribavirin | |
| Epigallocatechin gallate | |

EXAMPLE 35

CATVIRA Tablet Characteristics: HPLC Analytical method for Assay of Ribavirin, Epigallocatechin gallate and Sofosbuvir in CATVIRA Film Coated Tablets. Validation of high performance liquid chromatographic Methods used for the assay of Ribavirin, Epigallocatechin gallate and Sofosbuvir in CATVIRA Film Coated Tablets.

Method Description & Principle: This report describes the validation of high performance liquid chromatographic Method for Assay of Ribavirin, Epigallocatechin gallate and Sofosbuvir in CATVIRA Film Coated Tablets.

Analytical Standards: Ribavirin, Epigallocatechin gallate and Sofosbuvir working standard standardized using Ribavirin, Epigallocatechin gallate and Sofosbuvir Reference standard.

EXAMPLE 36

Reagent & Materials:
Methanol HPLC Grade, Acetonitrile HPLC Grade, Tetrahydrofuran HPLC Grade, Ammonium acetate, Sofosbuvir, Epigallocatechin gallate and Ribavirin working standard.

EXAMPLE 37

Chromatographic Conditions:—
Column: Symmetry (C18 (5 µm) 4.6×250 mm) or equivalent.
Flow rate: 0.8 ml/min.
Detector: UV at λ242 nm
Injection volume: 10 µl
Mobile phase: (Acetonitrile: Tetrahydrofuran: Ammonium Acetate) (10:40:50)
Acetate Buffer: into 1000 ml volumetric flask, weight 1 gm of Ammonium Acetate buffer, add 900 ml purified water shake to dissolve then complete to the volume by the same solvent. Adjust pH 3.5 by Glacial Acetic acid

EXAMPLE 38

Standard Preparation:
Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then complete to volume with the same solvent, and mix.

Transfer 5 ml of stock into volumetric flask 100 ml and complete to volume with mobile phase, and mix (Sofosbuvir Conc. 50 µg/ml, Epigallocatechin gallate Conc. 50 µg/ml and Ribavirin Conc. 125 µg/ml) working standard.

EXAMPLE 39

Test Preparation:—
Grind 20 tablets to fine powder; transfer quantitatively a weight of the powder equivalent to one tablet into a 200 ml volumetric flask, add 50 ml of Diluent, Sonicate 15 min, cool to room temperature, then complete to volume with the same solvent mix and filter. Take 5 ml of above solution into 100 ml volumetric flask, complete to the volume by Mobile phase and mix (Sofosbuvir Conc. 50 µg/ml, Epigallocatechin gallate Conc. 50 µg/ml and Ribavirin Conc. 125 µg/ml) working standard.

EXAMPLE 40

Procedure:—
Equilibrate the column, inject the specified volume (10 µl) of the working standard solution three times, and calculate the relative standard deviation of the each peak areas, which should not be more than 2%.

Inject the test solution and the standard solution in the following sequence (St, St, St, t, t, St)
Calculations:—

$$\% \text{ of Ribavirin} = \frac{At1}{Ast1} \times \frac{Cst1}{Ct1} \times P$$

Where:—
$At_1$: Peak Area of Ribavirin Test
$Ast_1$: Average Peak Area of Ribavirin Standard
$Cst_1$: Concentration of Ribavirin Standard
$Ct_1$: Concentration of Ribavirin Test
P: Potency of Standard.
Limit: 90%-110%
Claim: 500 mg Ribavirin $$\% \text{ of Epigallocatechin gallate} = \frac{At2}{Ast2} \times \frac{Cst2}{Ct2} \times P$$

Where:—
$At_2$: Peak Area of Epigallocatechin gallate Test
$Ast_2$: Average Peak Area of Epigallocatechin gallate Standard
$Cst_2$: Concentration of Epigallocatechin gallate Standard
$Ct_2$: Concentration of Epigallocatechin gallate Test
P: Potency of Standard.
Limit: 90%-110%
Claim: 200 mg Epigallocatechin gallate $$\% \text{ of Sofosbuvir} = \frac{At3}{Ast3} \times \frac{Cst3}{Ct3} \times P$$

Where:—
$At_3$: Peak Area of Sofosbuvir Test
$Ast_3$: Average Peak Area of Sofosbuvir Standard $Cst_3$: Concentration of Sofosbuvir Standard
$Ct_3$: Concentration of Sofosbuvir Test
P: Potency of Standard.
limit: 90%-110%
Claim: 200 mg Sofosbuvir

EXAMPLE 41

Documentation Required:—
Analytical monograph for Ribavirin, Epigallocatechin gallate and Sofosbuvir in CATVIRA Film Coated Tablets
Equipment operation, cleaning, and calibration procedures.
Reference standards handling procedure.
Chemicals, reagents and solutions in QC.

EXAMPLE 42

Validation Protocol

Analytical Method Validation

Assay of Ribavirin, Epigallocatechin gallate and Sofosbuvir in Catvira Film Coated Tablets by HPLC.

TABLE 8

Analytical Performance Characteristics and Acceptance Criteria

| Parameters | Acceptance criteria | Reference |
|---|---|---|
| Precision repeatability | RSD ≤ 2% or as specified in the individual monograph. | FDA |
| Linearity and range | $R^2$ ≥ 0.999 | FDA |
| Specificity/Selectivity | No interference/resolution NLT 2 | FDA |
| Accuracy and Recovery | 98-102% | In house |
| Limit of Detection | (3.3 × Standard error)/Slope | ICH |
| Limit of Quantitation | (10 × Standard error)/Slope | IC |
| Ruggedness | Pooled RSD ≤ 3% in every change item. | In house |
| Robustness | Pooled RSD ≤ 3% in every change item. | In house |
| Stability indicating properties | The method is stability indicating. | FDA |

EXAMPLE 43

Safety Measures:—
 Safety instructions.
Procedure:—
Precision: (Repeatability)
 Definition: Repeatability is usually demonstrated by repeated measurements of a single sample (e.g. use of the analytical procedure within a laboratory over a short period of time using the same analyst with the same equipment). A minimum of three determinations at each of three concentrations across the intended range, or a minimum of six determinations at the test concentration is recommended.

EXAMPLE 44

Experimental Conduct: This study was conducted by performing multiple analyses on the same portion of a homogeneous sample. The system precision was assessed using 6 replicates of the 100% Test concentration.

TABLE 9

Precision results: (Repeatability)

Acceptance criteria

| Replicate Number | Ribavirin | Epigallocatechin gallate | Sofosbuvir | |
|---|---|---|---|---|
| Replicate # 1 | 321.05472 | 689.00159 | 306.82468 | |
| Replicate # 2 | 320.06686 | 686.39966 | 304.17117 | |
| Replicate # 3 | 320.80652 | 687.62341 | 304.68091 | |
| Replicate # 4 | 321.54575 | 686.9068 | 306.41183 | |
| Replicate # 5 | 321.37299 | 684.82056 | 306.67056 | |
| Replicate # 6 | 322.33078 | 685.17017 | 307.35703 | |
| Mean | 321.20 | 686.65 | 306.02 | |
| SD | 0.76 | 1.56 | 1.28 | |
| RSD %: | 0.237% | 0.227% | 0.419% | RSD % ≤ 2% |

Comment: The method was found to be precise, as the RSD is less than 2%.

EXAMPLE 45

Linearity and Range:—
 Definition: Linearity of an analytical procedure is its ability, within a given range, to obtain test results which are directly proportional to the concentration of analyte in the sample. Linearity suitable for single point standardization should extend to at least 20% beyond the specification range and include the target concentration. Linearity is defined by the correlation coefficient, which should be found to be ≥0.999, using peak area responses.
 Experimental Conduct: Linearity was performed by preparing a minimum 5 different concentrations, and then making 3 replicates of each concentration.
 Procedure: Linearity is performed by preparing 5 different percent of concentrations (50%, 80%, 100%, 120%, and 150%) and inject in HPLC, 3 replicates of each Concentration.

TABLE 10

Linearity and range results for Ribavirin

| % Working Con. | Concentration (μg/ml) | Replicate T1 | Replicate T2 | Replicate T3 | Mean | Acceptance criteria |
|---|---|---|---|---|---|---|
| 50 | 62.5 | 158.03261 | 154.25015 | 154.23546 | 156 | |
| 80 | 100 | 253.06224 | 251.74188 | 251.67638 | 257 | |
| 100 | 125 | 318.80569 | 320.11548 | 319.4379 | 319 | |
| 120 | 150 | 381.30368 | 381.62775 | 381.67468 | 387 | |

Observed peak Areas of Ribavirin

TABLE 10-continued

Linearity and range results for Ribavirin

| % Working Con. | Concentration (μg/ml) | Observed peak Areas of Ribavirin | | | | Acceptance criteria |
|---|---|---|---|---|---|---|
| | | Replicate T1 | Replicate T2 | Replicate T3 | Mean | |
| 150 | 187.5 | 472.81772 | 472.0192 | 473.08466 | 473 | |
| Slope: | | | 2.54403 | | | |
| Intercept: | | | −1.74488 | | | |
| $R^2$ | | | 0.99960 | | | ≥0.999 |

Comment: The method was found to be linear as the $R^2$ is greater than 0.999 (0.99960).

TABLE 11

Linearity and range results for Epigallocatechin gallate

| % Working Conc. | Conc. (μg/ml) | Observed peak Areas of Epigallocatechin gallate | | | | Acceptance criteria |
|---|---|---|---|---|---|---|
| | | Replicate T1 | Replicate T2 | Replicate T3 | Mean | |
| 50 | 25 | 336.00464 | 320.60452 | 318.08795 | 325 | |
| 80 | 40 | 544.77533 | 542.31067 | 547.4621 | 545 | |
| 100 | 50 | 675.09912 | 675.06488 | 673.47437 | 675 | |
| 120 | 60 | 813.66547 | 810.7735 | 810.12628 | 812 | |
| 150 | 75 | 1013.97992 | 1011.49445 | 1011.86182 | 1012 | |
| Slope: | | | 13.69337 | | | |
| Intercept: | | | −11.01604 | | | |
| $R^2$ | | | 0.99955 | | | ≥0.999 |

Comment: -The method was found to be linear as the $R^2$ is greater than 0.999 (0.99955)

EXAMPLE 46

Chemical Name: (−)-Epigallocatechin Gallate
Abbreviation Name: EGCG
Chemistry:

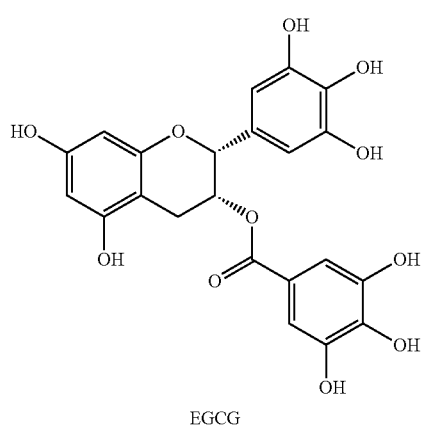 [SMILES: O=C(O[C@@H]1Cc2c(O)cc(O)cc2O[C@@H]1c1cc(O)c(O)c(O)c1)c1cc(O)c(O)c(O)c1]

EGCG

CAS Registry Number: 989-51-5
CAS Index Name: Benzoic acid, 3,4,5-trihydroxy-, (2R, 3R)-3,4-dihydro-5,7-dihydroxy-2-(3,4, 5-trihydroxyphenyl)-2H-1-benzopyran-3-yl ester
Molecular Weight: 458.37 g/mol
pKa (Predicted): Value: 7.75±0.25|Condition: Most Acidic Temp: 25° C.
Melting Point (Experimental): Value: 217° C.
Boiling Point (Predicted): Value: 909.1±65.0° C.|Condition: Press: 760 Torr
Density (Predicted): Value: 1.90±0.1 g/cm3|Condition: Temp: 20° C. Press: 760 Torr
Purity>98%
It is phytoextraction as the enterprise standard.

Other IUPAC Names:
[(2R, 3R)-5, 7-dihydroxy-2-(3, 4, 5-trihydroxyphenyl) chroman-3-yl] 3, 4, 5-trihydroxybenzoate Epigallocatechol, 3-gallate (7CI), Epigallocatechol, 3-gallate, (−)-(8CI), Epigallocatechol, gallate (6CI), Gallic acid, 3-ester with epigallocatechol, (−)-(8CI), (−)-Epigallocatechin 3-O-gallate, (−)-Epigallocatechin 3-gallate, (−)-Epigallocatechin gallate, (−)-Epigallocatechol gallate, (−)-epi-Gallocatechin 3-O-gallate, and 3-O-Galloyl-(−)-epigallocatechin

EXAMPLE 47

Oligomer EGCG:
Oligomerized EGCG conjugated with Chitosan and the reaction was initiated with the addition of acetaldehyde, and was conducted at room temperature and low pH 2-3 under a nitrogen atmosphere for 2-3 days (FIG. 16).

Chitosan—Oligomeric EGCG complex with Glycyrrhizin (Glycyrrhetinic acid) forming a nanoparticle (100-300 nm, with +10 to +20 zeta potential) (FIG. 17) for encapsulation if Ribavirin and Sofosbuvir.

EXAMPLE 48

TABLE 12

Linearity and range results for Sofosbuvir

| % Working Conc. | Conc. (μg/ml) | Observed peak Areas of Sofosbovir Replicate T1 | Replicate T2 | Replicate T3 | Mean | Acceptance criteria |
|---|---|---|---|---|---|---|
| 50 | 25 | 147.74237 | 150.03767 | 149.88536 | 149 | |
| 80 | 40 | 238.71823 | 239.08977 | 239.89888 | 239 | |
| 100 | 50 | 302.17963 | 303.26328 | 302.99454 | 303 | |

TABLE 12-continued

Linearity and range results for Sofosbuvir

| % Working Conc. | Conc. (µg/ml) | Observed peak Areas of Sofosbovir | | | | Acceptance criteria |
| --- | --- | --- | --- | --- | --- | --- |
| | | Replicate T1 | Replicate T2 | Replicate T3 | Mean | |
| 120 | 60 | 365.27634 | 366.28247 | 366.21646 | 366 | |
| 150 | 75 | 450.27753 | 451.25446 | 451.34259 | 451 | |
| Slope: | | | 6.07607 | | | |
| Intercept: | | | −2.17296 | | | |
| $R^2$ | | | 0.99956 | | | ≥0.999 |

Comment: The method was found to be linear as the $R^2$ is greater than 0.999 (0.99956)

EXAMPLE 49

Accuracy and Recovery:

Definition: Accuracy was evaluated by spiking standard solution. The measurements are made at a concentration of Ribavirin, Epigallocatechin gallate and Sofosbuvir in CAT-VIRA Film Coated Tablets, which is found to be the target concentration, and at suitable intervals around this point.

Experimental Conduct:—

Placebo except the active ingredient was spiked with known quantities of Ribavirin, Epigallocatechin gallate and Sofosbuvir working standard.

Accuracy was assessed using nine determinations over three Concentrations level Covering the specified range (i.e. three concentrations and three replicates).

The measurements were made at a concentration, which is to be the (100%) specification, and at suitable concentration intervals around this concentration.

Accuracy and Recovery Results:—

TABLE 13

Ribavirin

| Working Concentration | | Observed | Found concentration | % | Acceptance |
| --- | --- | --- | --- | --- | --- |
| % | (µg/ml) | peak Areas | (µg/ml) | Recovery | criteria |
| 80% | 80 | 251.34544 | 78.73 | 98.41 | |
| | | 251.65329 | 78.83 | 98.53 | |
| | | 251.51596 | 78.78 | 98.48 | |
| 100% | 100 | 319.99435 | 100.23 | 100.23 | |
| | | 319.53372 | 100.09 | 100.09 | |
| | | 320.41434 | 100.37 | 100.37 | |
| 120% | 120 | 381.28662 | 119.43 | 99.53 | |
| | | 385.16199 | 120.65 | 100.54 | |
| | | 386.87228 | 121.18 | 100.99 | (98.0-102.0%) |

EXAMPLE 50

TABLE 14

Epigallocatechin gallate

| Working Concentration | | Observed | Found concentration | % | Acceptance |
| --- | --- | --- | --- | --- | --- |
| % | (µg/ml) | peak Areas | (µg/ml) | Recovery | criteria |
| 80% | 80 | 533.28894 | 81.35 | 101.69 | |
| | | 533.09717 | 81.32 | 101.65 | |
| | | 531.73505 | 81.11 | 101.39 | |
| 100% | 100 | 661.39655 | 100.89 | 100.89 | |
| | | 662.34644 | 101.03 | 101.03 | |
| | | 663.63428 | 101.23 | 101.23 | |

TABLE 14-continued

Epigallocatechin gallate

| Working Concentration | | Observed | Found concentration | % | Acceptance |
| --- | --- | --- | --- | --- | --- |
| % | (µg/ml) | peak Areas | (µg/ml) | Recovery | criteria |
| 120% | 120 | 800.86377 | 122.16 | 101.80 | |
| | | 801.30817 | 122.3 | 101.86 | |
| | | 800.25696 | 122.07 | 101.73 | (98.0-102.0%) |

EXAMPLE 51

TABLE 15

Sofosbuvir

| Working Concentration | | Observed | Found concentration | % | Acceptance |
| --- | --- | --- | --- | --- | --- |
| % | (µg/ml) | peak Areas | (µg/ml) | Recovery | criteria |
| 80% | 80 | 241.58926 | 80.35 | 100.44 | |
| | | 242.54837 | 80.67 | 100.84 | |
| | | 242.35535 | 80.61 | 100.76 | |
| 100% | 100 | 305.91193 | 101.75 | 101.75 | |
| | | 300.70554 | 100.01 | 100.01 | |
| | | 299.4812 | 99.61 | 99.61 | |
| 120% | 120 | 364.64575 | 121.28 | 101.07 | |
| | | 364.30817 | 121.17 | 100.97 | |
| | | 365.74869 | 121.65 | 101.37 | (98.0-102.0%) |

Comment: The method was found to be accurate within (98%-102%) at the range of about 80% to 120% of the working concentration.

EXAMPLE 52

Selectivity & Specificity:—

Definition:

Forced degradation studies were performed to provide an indication of the stability-indicating properties, selectivity and specificity of the procedure. Accelerated degradation was attempted using acid and base hydrolysis, effect of heat and oxidation, in addition to injection of well-known degradation products (resolution solution).

EXAMPLE 53

Acceptance Criteria:—

The method to be selective and stability indicating, the peaks of Ribavirin, Epigallocatechin gallate and Sofosbuvir, mix standard should be resolute from any other peak that may appear due to degradation.

Experimental Conduct:—

Placebo Preparation: Grind 20 tablets to fine powder, transfer quantitatively a weight of the powder equivalent to one Placebo of tablet into a 200 ml volumetric flask, add 50 ml of Diluent, Sonicate 15 min, cool to room temperature, then complete to volume with the same solvent mix and filter, Take 5 ml of above solution into 100 ml volumetric flask, complete to the volume by Mobile phase and mix

EXAMPLE 54

Basic Hydrolysis of CATVIRA Film Coated Tablets:
—Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then add 25 ml of 0.1 N NaOH put in water path at 60 C.° for 30 min, then neutralized with 0.1 N HCl solution, then complete to volume with Diluent, and mix. Transfer 5 ml of stock into volumetric flask 100 ml and complete to volume with mobile phase, and mix

EXAMPLE 55

Acid Hydrolysis of CATVIRA Film Coated Tablets: Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then add 25 ml of 0.1 N HCl put in water path at 60 C.° for 30 min, then neutralized with 0.1 N NaOH solution, then complete to volume with Diluent, and mix. Transfer 5 ml of stock into volumetric flask 100 ml and complete to volume with mobile phase, and mix

EXAMPLE 56

Oxidation of CATVIRA Film Coated Tablets: Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then add 10 ml of Hydrogen peroxide (30%) put in water path at 60 C.° for 30 min, then complete to volume with Diluent, and mix.

Transfer 5 ml of stock into volumetric flask 100 ml and complete to volume with mobile phase, and mix

EXAMPLE 57

Heating Degradation of CATVIRA Film Coated Tablets: Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then put in oven at 60 C.° for 30 min, then complete to volume with Diluent, and mix.

Transfer 5 ml of stock into volumetric flask 100 ml and complete to volume with mobile phase, and mix

EXAMPLE 58

Limit of Detection:—
Definition: The concentration at which Ribavirin, Epigallocatechin gallate and Sofosbuvir can be detected but not necessarily quantified.
Experimental Conduct:
Limit of Detection (LOD)=(3.3×Standard error)/Slope

EXAMPLE 59

Limit of Quantitation:—
Definition: LOQ is the concentration at which the. Peak of Paraben Ribavirin, Epigallocatechin gallate and Sofosbuvir detected and quantified.
Experimental Conduct:—
Limit of Quantitation(LOQ)=(10×Standard error)/Slope

TABLE 16

Limit of detection and limit of quantitation for the API

| Name of the active | Ribavirin | Epigallocatechin gallate | Sofosbuvir |
|---|---|---|---|
| Limit Of Detection | 3.61 µg/ml | 1.53 µg/ml | 1.52 µg/ml |
| Limit of Quantitation | 10.93 µg/ml | 4.65 µg/ml | 4.60 g/ml |

EXAMPLE 60

Ruggedness:
Definition: The ruggedness of analytical method is determined by analysis of the same samples from Homogeneous lot of materials, under different conditions but typical test conditions.
Acceptance Criteria:—
The method to be rugged, at any of the following items the pooled % RSD of the total number of replicates that have been made in this item should be ≤3%
Experimental Conduct:
Ruggedness of an analytical method is the degree of reproducibility of test results obtained by the analysis of the same samples under a variety of conditions, such as different laboratories, different analysts, different Column, different instruments, different lots of reagents, different elapsed assay time different days, etc.

Day to Day: First day: 6 replicates of a single sample of powder material or product (100%) are used for each determination. Then on a second day: 6 replicates of freshly prepared test from the same sample are analyzed. The same analyst performs both tests.

Analyst to Analyst: It is performed to provide information about ruggedness between different analysts. Six (6) replicates of a single sample are analyzed then the other person analyzed 6 replicates from the same sample prepared by him.

Column to Column: The same analytical method is performed on columns of the same packing material and length but of different batch number or supplier

TABLE 17

| | Day to day results: | | | | | | |
|---|---|---|---|---|---|---|---|
| | Ribavirin | | Epigallocatechin gallate | | Sofosbuvir | | Acceptance |
| Replicate # | First day | Second day | First day | Second day | First day | Second day | criteria |
| Replicate # 1 | 321.0170 | 331.6282 | 646.7464 | 658.28589 | 320.4861 | 308.59796 | |
| Replicate # 2 | 320.9103 | 324.0331 | 662.41559 | 645.76794 | 304.3353 | 302.48746 | |
| Replicate # 3 | 320.4938 | 329.9692 | 658.08588 | 682.52917 | 315.5145 | 302.01242 | |
| Replicate # 4 | 320.0612 | 328.0512 | 658.55048 | 651.54401 | 314.7174 | 302.70016 | |

TABLE 17-continued

| | Day to day results: | | | | | | |
|---|---|---|---|---|---|---|---|
| | Ribavirin | | Epigallocatechin gallate | | Sofosbuvir | | Acceptance |
| Replicate # | First day | Second day | First day | Second day | First day | Second day | criteria |
| Replicate # 5 | 319.5959 | 324.7946 | 677.39343 | 644.19336 | 307.7964 | 308.29837 | |
| Replicate # 6 | 319.7175 | 327.7118 | 671.86005 | 652.98035 | 313.0821 | 305.15982 | |
| POOLED AV. | 324.00 | | 659.20 | | 308.77 | | |
| STD: | 4.36 | | 12.45 | | 5.97 | | |
| RSD: | 1.344% | | 1.889% | | 1.935% | | Pooled RSD ≤3% |

Comment: The analytical method is found to be rugged from day to another day, as the pooled RSD of the result of two different days is lower than 3%.

TABLE 18

| | Analyst-to-Analyst results: | | | | | | |
|---|---|---|---|---|---|---|---|
| | Ribavirin | | Epigallocatechin gallate | | Sofosbuvir | | Acceptance |
| Replicate # | Analyst -1 | Analyst -2 | Analyst -1 | Analyst -2 | Analyst -1 | Analyst -2 | criteria |
| Replicate # 1 | 321.0170 | 319.8675 | 646.7464 | 661.99969 | 320.4860 | 318.7009 | |
| Replicate # 2 | 320.9103 | 319.5574 | 662.41559 | 667.77502 | 304.3353 | 306.1590 | |
| Replicate # 3 | 320.4938 | 320.2339 | 658.08588 | 668.68683 | 315.5145 | 321.3010 | |
| Replicate # 4 | 320.0612 | 321.0060 | 658.55048 | 659.92285 | 314.7174 | 311.6148 | |
| Replicate # 5 | 319.5959 | 320.1773 | 677.39343 | 658.20697 | 307.7965 | 317.7582 | |
| Replicate # 6 | 319.7176 | 319.5368 | 671.86005 | 648.9566 | 313.0821 | 314.6374 | |
| POOLED AV. | 320.18 | | 661.72 | | 313.84 | | |
| STD: | 0.56 | | 8.84 | | 5.51 | | |
| RSD: | 0.176% | | 1.336% | | 1.757% | | Pooled |

Comment: the method is found to be rugged between different analysts as the pooled RSD of the result obtained from two different analysts is lower than 3%.

TABLE 19

| | Column to column results: | | | | | | |
|---|---|---|---|---|---|---|---|
| | Ribavirin | | Epigallocatechin gallate | | Sofosbuvir | | Acceptance |
| Replicate # | Column1 | Column2 | Colmnn1 | Column2 | Column1 | Column2 | criteria |
| Replicate # 1 | 321.05472 | 326.7 | 689.00159 | 681.6 | 306.82468 | 307.9 | |
| Replicate # 2 | 320.06686 | 328.0 | 686.39966 | 681.9 | 304.17117 | 308.6 | |
| Replicate # 3 | 320.80652 | 328.9 | 687.62341 | 671.2 | 304.68091 | 309.2 | |
| POOLED | 324.2 | | 683.0 | | 306.9 | | |
| STD: | 4.0 | | 6.5 | | 2.1 | | |
| RSD: | 1.241% | | 0.950% | | 0.677% | | Pooled |

Comment: The analytical method is found to be rugged from a column to another as the Pooled % RSD of the results obtained from two different columns is lower than 3%.

EXAMPLE 61

Robustness:

Definition: Robustness is determined by observing how a method stands up to slight variations in normal operating parameters. For HPLC for instance, this could be change if slight variation in mobile phase composition or pH variation and flow rate.

TABLE 20

Change in Flow Rate

| Replicate # | Ribavirin | | | Epigallocatechin gallate | | | Sofosbuvir | | | Acceptance criteria |
| --- | --- | --- | --- | --- | --- | --- | --- | --- | --- | --- |
| | Flow 0.8 ml/min | Flow 0.82 ml/min | Flow 0.78 ml/min | Flow 0.8 ml/min | Flow 0.82 ml/min | Flow 0.78 ml/min | Flow 0.8 ml/min | Flow 0.82 ml/min | Flow 0.78 ml/min | |
| Replicate # 1 | 321.05 | 322.24 | 317.53 | 689.00 | 680.52 | 677.80 | 306.82 | 316.06 | 310.05 | |
| Replicate # 2 | 320.06 | 319.86 | 313.88 | 686.40 | 678.68 | 670.91 | 304.17 | 315.43 | 306.95 | |
| Replicate # 3 | 320.80 | 318.41 | 313.93 | 687.62 | 677.47 | 670.54 | 304.68 | 316.68 | 306.57 | |
| POOLED AV. | 319 | | | 680 | | | 310 | | | Pooled RSD ≤3% |
| STD: | 3 | | | 7 | | | 5 | | | |
| RSD; | 0.949% | | | 0.994% | | | 1.269% | | | |

Comment: The analytical method is found to be robust from different flow rate as the Pooled % RSD of the results obtained from two different columns is lower than 3%.

EXAMPLE 62

Stability Indicating:

Stability indicating studies are performed to provide an indication of the stability-indicating properties of the procedure. This is carried out by using known concentration of degradation product or by accelerated degradation of parent product using stress test conditions (acid and base hydrolysis, Oxidation and Effect of Heat). Acceptable resolution of the Ribavirin, Epigallocatechin gallate and Sofosbuvir from the degradation products was obtained (the resolution between peak and the nearest peak is more than 2).

The analytical method of determination of Ribavirin, Epigallocatechin gallate and Sofosbuvir in CATVIRA Film Coated Tablets was examined for precision, repeatability, linearity, accuracy, ruggedness, Robustness, specificity and sensitivity. The system was found to be precise as the RSD of 6 replicate injections of the standard solution is less than 2%. The method was found to be linear for Ribavirin, Epigallocatechin gallate and Sofosbuvir at the specified range, as the r is greater than 0.999.

The method was found to be accurate as the percentage recovery is ranged within (98%-102%) at the range of 80% to 120%

The method was robust for slight change in the concentration of the organic modifier in the mobile phase, change in the flow rate as the RSD is less than 3%

The proposed analytical method of Ribavirin, Epigallocatechin gallate and Sofosbuvir in CATVIRA Film Coated Tablets was found to be precise, repeatable, linear, accurate, rugged, robust, specific and sensitive. Results demonstrate that the method is suitable for its intended use.

EXAMPLE 63

Method of Analysis CATVIRA Film Coated Tablets
1. Physical Properties:
1.1. Description: Yellow to deep yellow, oblong, biconvex, film coated tablets
1.2. Determination of Average of Weight: (Limit: 1000 mg±5%) Proceed as BP2014
1.3. Determination of Disintegration Time: (Limit: NMT 30 min) Proceed as USP 35
1.4. Determination of Dissolution test for Sofosbuvir and Ribavirin:
Conditions of Dissolution:—
USP Apparatus: II (Paddle)
Speed: 75 rpm
Media: Phosphate buffer PH 6.8
Time: 60 min.
Volume: 900 ml
Reagent & Materials:—
Methanol HPLC Grade.
Acetonitrile HPLC Grade
Tetrahydrofuran HPLC Grade.
Ammonium acetate
Sofosbuvir and Ribavirin working standard.
Apparatus & Equipement:—
  Calibrated Analytical balance accurate to±0.1 mg
  HPLC:—Waters UV detector or equivalent
  Column: Symmetry (C18 (5 µm) 4.6×250 mm) or equivalent.
  Sonicator with temperature control
  Volumetric flasks
  Pipettes class A
Chromatographic Conditions:—
  Column: Symmetry (C18 (5 µm) 4.6×250 mm) or equivalent.
  Flow rate: 0.8 ml/min.
  Detector: UV at λ242 nm
  Injection volume: 10 µl
  Mobile phase: (Acetonitrile: Tetrahydrofuran: Ammonium Acetate) (10:40:50)
  Acetate Buffer: into 1000 ml volumetric flask, weight 1 gm of Ammonium Acetate buffer, add 900 ml purified water shake to dissolve then complete to the volume by the same solvent, adjust pH 3.5 by Glacial Acetic acid.
  Diluent: (H2O: Methanol) (50:50)
  Standard Solution: Weigh about 22.2 mg Sofosbuvir working standard and about 55.5 mg of Ribavirin into 100 ml volumetric flask, add 20 ml Diluent, Sonicate 15 min, cool to room temperature, then complete to volume with the media, and mix
  Transfer 5 ml of above solution into 25 ml volumetric flask complete to volume with dissolution medium (Sofosbuvir Conc. 44.4 µg/ml and Ribavirin Conc. 111.1 µg/ml) working standard.

EXAMPLE 64

Test Solution:

Transfer quantitatively 900 ml of the dissolution media in each dissolution vessel and heat till temperature reaches 37° C.±0.5° C., Put one tablet in each vessel and start the apparatus, after 60 min, pipette 20 ml from each vessel then filter.

Transfer 5 ml of above solution into 25 ml volumetric flask complete to volume with dissolution medium (Sofosbuvir Conc. 44.4 µg/ml and Ribavirin Conc. 111.1 µg/ml) working standard.

Procedure: Equilibrate the column, inject the specified volume (10 μl) of the working standard solution three times, calculate the relative standard deviation of the each peak areas, should not be more than 2%.

Inject the test solution and the standard solution in the following sequence (St, St, St, t, t, t, St, t, t, t, St).

Calculations:

$$\% \text{ of Sofosbuvir} = \frac{At1}{Ast1} \times \frac{Cst1}{Ct1} \times P$$

Where:—
$At_1$: Peak Area of Sofosbuvir Test
$Ast_1$: Average Peak Area of Sofosbuvir Standard
$Cst_1$: Concentration of Sofosbuvir Standard
$Ct_1$: Concentration of Sofosbuvir Test
P: Potency of Standard.
Dissolution test: NLT 75% after 60 min from the labeled claim
Claim: 200 mg Sofosbuvir $$\% \text{ of Ribavirin} = \frac{At2}{Ast2} \times \frac{Cst2}{Ct2} \times P$$

Where:—
$At_2$: Peak Area of Ribavirin Test
$Ast_2$: Average Peak Area of Ribavirin Standard
$Cst_2$: Concentration of Ribavirin Standard
$Ct_2$: Concentration of Ribavirin Test
P: Potency of Standard.
Dissolution test: NLT 75% after 60 min from the labeled claim
Claim: 500 mg Ribavirin.

Chemical Properties:
Identification Test for Ribavirin, Epigallocatechin Gallate and Sofosbuvir.
The retention time of the major peaks in the chromatogram of the Test preparation corresponding to that of the standard preparation as obtained in the assay.

EXAMPLE 65

Assay of Sofosbuvir, Epigallocatechin Gallate and Ribavirin Working Standard F C.T by HPLC:—
Reagent & Materials:—
  Methanol HPLC Grade.
  Acetonitrile HPLC Grade
  Tetrahydrofuran HPLC Grade.
  Ammonium acetate
  Sofosbuvir, Epigallocatechin gallate and Ribavirin working standard.
Chromatographic Conditions:—
  Column: Symmetry (C18 (5 μm) 4.6×250 mm) or equivalent.
  Flow rate: 0.8 ml/min.
  Detector: UV at λ242 nm
  , Injection volume: 10 μl
  Mobile phase: (Acetonitrile: Tetrahydrofuran: Ammonium Acetate) (10:40:50)
  Acetate Buffer: into 1000 ml volumetric flask, weight 1 gm of Ammonium Acetate buffer, add 900 ml purified water shake to dissolve then complete to the volume by the same solvent. Adjust pH 3.5 by Glacial Acetic acid Standard Preparation:—
Weigh about 100 mg Sofosbuvir working standard and about 100 mg Epigallocatechin gallate working standard and about 250 mg of Ribavirin working standard into 100 ml volumetric flask, add 70 ml Diluent, Sonicate 15 min, cool to room temperature, then complete to volume with the same solvent, and mix.

Transfer 5 ml of stock into volumetric flask 100 ml and complete to volume with mobile phase, and mix (Sofosbuvir Conc. 50 μg/ml, Epigallocatechin gallate Conc. 50 μg/ml and Ribavirin Cone. 125 μg/ml) working standard.

Test Preparation: Grind 20 tablets to fine powder; transfer quantitatively a weight of the powder equivalent to one tablet into a 200 ml volumetric flask, add 50 ml of Diluent, Sonicate 15 min, cool to room temperature, then complete to volume with the same solvent mix and filter, Take 5 ml of above solution into 100 ml volumetric flask, complete to the volume by Mobile phase and mix (Sofosbuvir Conc. 50 μg/ml, Epigallocatechin gallate Conc. 50 μg/ml and Ribavirin Conc. 125 μg/ml) working standard.

Procedure: Equilibrate the column, inject the specified volume (10 μl) of the working standard solution three times, calculate the relative standard deviation of the each peak areas, should not be more than 2%.

Inject the test solution and the standard solution in the following sequence (St, St, St, t, t, St)

Calculations:—

$$\% \text{ of Ribavirin} = \frac{At1}{Ast1} \times \frac{Cst1}{Ct1} \times P$$

Where:—
$At_1$: Peak Area of Ribavirin Test
$Ast_1$: Average Peak Area of Ribavirin Standard
$Cst_1$: Concentration of Ribavirin Standard
$Ct_1$: Concentration of Ribavirin Test
P: Potency of Standard.
Limit: 90%-110%
Claim: 500 mg Ribavirin $$\% \text{ of Epigallocatechin gallate} = \frac{At2}{Ast2} \times \frac{Cst2}{Ct2} \times P$$

Where:—
$At_2$: Peak Area of Epigallocatechin gallate Test
$Ast_2$: Average Peak Area of Epigallocatechin gallate Standard
$Cst_2$: Concentration of Epigallocatechin gallate Standard
$Ct_2$: Concentration of Epigallocatechin gallate Test
P: Potency of Standard.
Limit: 90%-110%
Claim: 200 mg Epigallocatechin gallate $$\% \text{ of Sofosbuvir} = \frac{At3}{Ast3} \times \frac{Cst3}{Ct3} \times P$$

Where:—
$At_3$: Peak Area of Sofosbuvir Test
$Ast_3$: Average Peak Area of Sofosbuvir Standard
$Cst_3$: Concentration of Sofosbuvir Standard
$Ct_3$: Concentration of Sofosbuvir Test
P: Potency of Standard.
limit: 90%-11/o
Claim: 200 mg Sofosbuvir

EXAMPLE 66

2. Microbiology (B.P 2014)
3.1 Total Viable Aerobic Bacterial Count
Preparation of Diluting Fluids (Buffered Sodium Chloride-Peptone Solution pH 7.0):

Into 1 liter flask, Weigh accurately 3.56 g of Potassium dihydrogen phosphate, 7.23 g of disodium hydrogen phosphate dihydrate, 4.30 g Sodium chloride, 1.0 g of Peptone (meat or casein) then make the volume with Purified water 1000 ml.

To this solution surface-active agents or in activators of antimicrobial agents may be added, (If needed) such as: Polysorbate 80 (1 g/L w/v to 10 g/L w/v). Sterilize by heating in an autoclave at 121° C. for 20 min.

Preparation of the Sample:

Water Soluble Products: Dissolve or dilute 10 g of the product to be examined in buffered sodium chloride-peptone solution pH 7.0 or in another suitable liquid.

In general a one in ten dilution is prepared. However, the characteristics of the product or the required sensitivity may necessitate the use of other ratios.

If the product is known to have antimicrobial activity, an inactivating agent shall be added to the diluents. If necessary adjust the pH to about pH 7 and prepare further serial tenfold dilution using the same diluent Examination of the Sample:

Plate Count Method:

Pour-plate method: using Petri dishes 9 cm in diameter, add to each dish 1 ml of the sample prepared and 15 ml to 20 ml of a liquefied agar medium suitable for the cultivation of bacteria (such as Casein soybean digest agar) not more than 45° C.

Prepare for each medium at least two Petri dishes for each level of dilution. Incubate the plates at 30° C. to 35° C. for bacteria and incubate from two to three days.

Take the arithmetic average of the counts and calculate the number of cfu/ml of product.

Limit: <$10^3$ cfu/ml for bacteria.

EXAMPLE 67

Molds and Yeasts Count:
Preparation of Diluting Fluids (Buffered Sodium Chloride-Peptone Solution pH 7.0):

Into 1 liter flask, Weigh accurately 3.56 g of Potassium dihydrogen phosphate, 7.23 g of disodium hydrogen phosphate dihydrate, 4.30 g Sodium chloride, 1.0 g of Peptone (meat or casein) then make the volume with Purified water 1000 ml.

To this solution a surface-active agents or in activators of antimicrobial agents may be added, (If needed) such as: Polysorbate 80 (1 g/L w/v to 10 g/L w/v).

Sterilize by heating in an autoclave at 121° C. for 20 min.

Water Soluble Products:

Dissolve or dilute 10 g of the product to be examined in buffered sodium chloride-peptone solution pH 7.0 or in another suitable liquid.

In general a one in ten dilution is prepared. However, the characteristics of the product or the required sensitivity may necessitate the use of other ratios.

If the product is known to have antimicrobial activity, an inactivating agent shall be added to the diluents. If necessary adjust the pH to about pH 7 and prepare further serial tenfold dilution using the same diluent.

Examination of the Sample:

Plate Count Method: Pour-plate method: using Petri dishes 9 cm in diameter, add to each dish 1 ml of the sample prepared and 15 ml to 20 ml of a liquefied agar medium suitable for the cultivation of fungi (such as Sabouraud dextrose agar) not more than 45° C.

Prepare for each medium at least two Petri dishes for each level of dilution. Incubate the plates at (20° C. to 25° C. for fungi) for five days.

Take the arithmetic average of the counts and calculate the number of cfu/ml of product.

Limit: <$10^2$ cfu/ml for fungi.

Pathogenic Micro-Organisms

*Escherichia coli:*

Use 10 g of the product to be examined (as preparation of the product under total viable count) to inoculate 100 ml of Casein soybean digest broth, homogenize and incubate at 35-37° C. for 18-48 h.

Shake the container, transfer 1 ml to 100 ml of MaCconkey broth and incubate at 43-45° C. for 18-24 h.

Subculture on plates of MaCconkey agar at 35-37° C. for 18-72 h. Growth of red, non-mucoid colonies of gram-negative rods indicates the possible presence of *E. coli*. This is confirmed by suitable biochemical tests, such as indole production.

The product passes the test if such colonies are not seen or if the confirmatory biochemical tests are negative.

Limit: Pathogens Free

TABLE 21

Quality Control: Specification
Name: CATVIRA Film Coated Tablets

| ACTIVE NAME | Ribavirin Epigallocatechin gallate Sofosbuvir | |
|---|---|---|
| Tests | Specification | Reference |
| A) Physical Test | | |
| 1. Appearance | Yellow to deep yellow, oblong, biconvex, film coated tablets | Mash Specs |
| 2. Average Weight | 1000 mg ± 5% | — |
| 3. Disintegration time | NMT 30 min | — |
| 4. Dissolution test for | | |
| Ribavirin | NLT 75% after 60 min | — |
| Sofosbuvir | NLT 75% after 60 min | — |
| B) Chemical Test | | |
| 1. Identification for | | |
| Ribavirin | Positive | — |
| Epigallocatechin gallate | Positive | — |
| Sofosbuvir | Positive | — |
| 2. Assay for | | |
| Ribavirin | 90-110% | — |
| Epigallocatechin gallate | 90-110% | — |
| Sofosbuvir | 90-110% | — |
| C) Microbiology Test | | |
| 1. Total Bacterial Count | NMT 1000 CFU/ml | — |
| 2. Total Fungal Count | NMT 100 CFU/ml | — |
| 3. Pathogenic organisms | Absent | — |

Single Tablet Sofosbuvir/Rabivarin/anti-hemolytic and viral entry inhibitor Catvira tablet

EXAMPLE 68

Catvira—Clinical Study Protocol

Study Title: Randomized, Open-Label, Study to Evaluate the Safety and Efficacy of Sofosbuvir tablet Plus Ribavirin tablet (Part A) versus single tablet of Catvira containing Sofosbuvir, Ribavirin, and Natural Bioactive Ingredient (B) in Egyptian Adults with Chronic Genotype 4 HCV Infection Indication: Hepatitis C Virus Infection

EXAMPLE 69

Protocol Synopsi

Catvira

Study Tide: A Randomized, Open-Label, Study to Evaluate the Safety and Efficacy of Sofosbuvir Plus Ribavirin (Part A) versus single tablet of Catvira containing Sofosbuvir, Ribavirin, and Natural anti-hemolytic (Part B) in Egyptian Adults with Chronic Genotype 4 HCV Infection Number of Subjects Planned: Part A: 40 subjects
  Part B: 40 subjects
    Cohort 1: approximately 40 subjects
    Cohort 2: up to 40 subjects Objectives: The primary objectives of Part A are as follows:
  To determine the efficacy of Sofosbuvir+Ribavirin in treatment-naïve and treatment-experienced subjects with chronic genotype 4 hepatitis C virus (HCV) infection as measured by the proportion of subjects with sustained viral response 12 weeks after discontinuation of therapy (SVR12)
  To assess the safety and tolerability of sofosbuvir+RBV in treatment-naïve and treatment-experienced subjects with chronic genotype 4 HCV infection as measured by review of the accumulated safety data The primary objectives of Part B are as follows:
  To determine the efficacy of Catvira containing Sofosbuvir (SOF)/Ribavirin (RBV)/EGCG (SOF/RBV/EGCG) fixed dose combination in subjects with chronic GT4 HCV infection as measured by the proportion of subjects with sustained viral response 12 weeks after discontinuation of therapy (SVR12)
  To assess the safety and tolerability of SOF/RBV/EGCG as assessed by review of the accumulated safety data The secondary objectives of this study are as follows:
  To determine the proportion of subjects who attain SVR at 4 and 24 weeks after discontinuation of therapy (SVR4 and SVR24)
  To evaluate the kinetics of circulating HCV RNA during treatment and after treatment discontinuation
  To evaluate the emergence of viral resistance to sofosbuvir, as relevant, during treatment and after treatment discontinuation Exploratory objectives of this study are:
  To explore the utility of non-genetic biomarkers, such as IP10, in predicting the natural history of disease, virological response to therapy, and/or the tolerability of medical therapies Study Design: Part A
  Randomized, open-label study in treatment-naïve and treatment-experienced, adults with chronic genotype 4 HCV infection.
  Treatment-naïve is defined as having never received treatment for HCV with any interferon (IFN), RBV, or other approved or experimental HCV-specific direct acting antivirals.
  Treatment-experienced is defined as:
    a) IFN Intolerant
    b) Non-response
    c) Relapse/Breakthrough It is planned that 40+40 subjects will be enrolled in the study such that an approximate even number of treatment-naïve and treatment-experienced subjects will be enrolled across the 2 treatment arms:
Arm 1
Sofosbuvir 400 mg once daily+RBV (1000 mg/day) for 12-24 weeks
Arm 2
Single Tablet containing SOF 400 mg, RBV 1000 mg, and Natural viral entry inhibitor, anti-fibrotic and anti-hemolytic (EGCG) at 400 mg for 12-24 weeks Treatment assignments will be stratified according to prior treatment experience and the presence or absence of cirrhosis.

Cohorts:
Cohort is a single-arm, open-label, non-randomized design in subjects who completed treatment in Part A of the study with SOF+RBV for 12-24 weeks or in Part B of the study with single Catvira Tablet containing SOF/RBV/EGCG FDC for 12-24 weeks.

Diagnosis and Main Eligibility Criteria: HCV RNA>$10^4$ IU/mL or HCV RNA>LLOQ and did not achieve SVR 12 after completing prior treatment in this study with chronic genotype 4 HCV infection. Treatment-naïve or treatment-experienced adults, male and non-pregnant/non-lactating female subjects, ages 18 years or older. See Section 0 and 1.2 of the protocol for detailed Inclusion and Exclusion criteria.

Study Procedures/Frequency: Study visits for all subjects will occur at screening, Baseline/Day 1.
  On-treatment visits will occur as follows:
    Part A, Arm 1 and 2—at the end of Weeks 1, 2, 4, 6, 8, 10, 12, 16, 20, and 24
  All subjects will complete a 4-Week Post-treatment visit regardless of treatment duration. Subjects with HCV RNA<LLOQ will continue to 12-Week and 24-Week Post-treatment visits unless confirmed viral relapse occurs at which time subjects will be early terminated from the study.
  Screening assessments include safety laboratory tests (chemistry, hematology, coagulation, and urinalysis), 12-lead ECG, HCV RNA, serology (HCV, HBV, and HIV), hemoglobin A1c, urine drug screen, liver imaging (cirrhotic), serum β-hCG (for all female subjects of child-bearing potential), physical examination (with height and bodyweight), vital signs, medical history, concomitant medications, and adverse events. In addition, subjects being screened for Part A and Part B (Cohort 1) will have HCV genotyping and IL28B genotyping performed.
  On-treatment assessments include safety laboratory tests (chemistry, hematology, and coagulation), HCV RNA, urine pregnancy tests (for all female subjects of child-bearing potential), physical examination, vital signs, concomitant medications, and adverse events.
  Post-treatment assessments include HCV RNA, urine pregnancy tests (for all female subjects of child-bearing potential), vital signs, concomitant medications, and adverse events.
  Samples will be collected at Baseline/Day 1 and every visit thereafter for viral RNA sequencing. Plasma samples will be collected during treatment visits for pharmacokinetic (PK) analysis of study drug (Part A only). Untested samples will be archived for up to 10 years.

Test Product, Dose, and Mode of Administration: SOF is manufactured as a 400-mg tablet for oral administration. Subjects will take 1 tablet for a total dose of 400 mg orally once daily in the morning with RBV (1000 mg.) and with food for 12-24 weeks.

The fixed dose Catvira combinations of SOF (400 mg)/RBV (100 mg)/EGCG (400 mg) in single tablet. Subjects will take 1 tablet with food for 12-24 weeks.

Reference Therapy, Dose, and Mode of Administration: None

Criteria for Evaluation:

Safety: Adverse events will be collected from baseline through the 4-Week Post-Treatment Visit and AEs related to study procedures, will be collected from when subjects sign the consent form. Clinical laboratory tests will be performed during treatment through the 12-Week Post-Treatment Visit.

Efficacy: Efficacy will be evaluated using scheduled assessments of HCV RNA performed using COBAS' TaqMan® HCV Test, v2.0 for Use with the High Pure System.

Statistical Methods: The primary efficacy endpoint is SVR12 (i.e., HCV RNA<LLOQ 12 weeks post-treatment) in all subjects who are randomized and treated. No statistical hypothesis testing will be performed. For each of the two treatment groups, a 2-sided 95% confidence interval using the exact binomial distribution will be constructed.

Part A: With a sample size of 40 subjects in each arm, a two-sided 95% exact confidence interval will extend at most 29% in length.

Part B: With a sample size of 40 subjects in each treatment group in Cohort 1, a 2-sided 95% exact confidence interval will extend at most 32% in length.

Secondary efficacy endpoints include the proportion of subjects with SVR4 and SVR24.

All continuous endpoints will be summarized using an 8-number summary (n, mean, standard deviation, median Q1, Q3, minimum, maximum) by treatment duration. All categorical endpoints will be summarized by number and percentage of subjects who meet the endpoint definition.

Safety endpoints will be analyzed by the number and percent of subjects with events or abnormalities for categorical values or using an 8-number summary (n, mean, standard deviation, median, Q1, Q3, minimum, maximum) for continuous data by treatment group.

Data from Part B will be analyzed separately from Part A and may be reported separately.

This study were conducted in accordance with the guidelines of Good Clinical Practices (GCPs) including archiving of essential documents.

EXAMPLE 70

Inclusion/Exclusion Criteria 1.1. Inclusion Criteria
1.1.1. Inclusion Criteria for Part A
Subjects must meet all of the following inclusion criteria to be eligible for participation in this study.
1. Willing and able to provide written informed consent.
2. Male or female, age ≥18 years.
3. HCV RNA≥$10^4$ IU/mL at screening.
4. Confirmed chronic HCV infection as documented by either:
   a. a positive anti-HCV antibody test or positive HCV RNA or positive HCV genotyping test at least 6 months prior to the Baseline/Day 1 visit, or
5. HCV genotype 4 at screening as determined by the Central Laboratory. Any non-definitive results will exclude the subject from study participation.
   i) IFN-intolerant: subject had documented intolerance to IFN during prior IFN therapy of up to 12 weeks duration
   ii) Non-response: subject did not achieve undetectable HCV RNA levels on treatment
   iii) Relapse/Breakthrough: subject achieved undetectable HCV RNA levels during treatment or within 4 weeks after treatment and later showed detectable HCV RNA
   a Absence of cirrhosis is defined as any one of the following:
      Liver biopsy within 2 years of Screening showing absence of cirrhosis
      Fibroscan® with a result of ≤12.5 kPa within 6 months of Baseline/Day 1
      FibroTest® score of ≤0.48 AND APRI of ≤1 performed during Screening
   In the absence of a definitive diagnosis of the presence or absence of cirrhosis by the above criteria, a liver biopsy is required. Liver biopsy results supersede the results obtained by Fibroscan or FibroTest®.
6. Body mass index (BMI)≥18 kg/m$^2$.
7. Screening ECG without clinically significant abnormalities.
8. Subjects must have the following laboratory parameters at screening:
   ALT<10× the upper limit of normal (ULN)
   AST≤10×ULN
   Hemoglobin≥12 g/dL for male, ≥11 g/dL for female subjects
   Platelets>50,000 cells/mm$^3$
   INR≤1.5×ULN unless subject has known hemophilia or is stable on an anticoagulant regimen affecting INR
   Albumin≥3 g/dL
   Direct bilirubin≤1.5×ULN
   HbA1c≤10%
   Creatinine clearance (CLcr)≥60 mL/min, as calculated by the Cockcroft-Gault equation
9. Subject has not been treated with any investigational drug or device within 30 days of the screening visit.
10. A female subject is eligible to enter the study if it is confirmed that she is:
   a Not pregnant or nursing
   b Of non-childbearing potential (i.e., women who have had a hysterectomy, both ovaries removed or medically documented ovarian failure, or are postmenopausal women >50 years of age with cessation [for ≥12 months] of previously occurring menses), or
   c Of childbearing potential (i.e., women who have not had a hysterectomy, both ovaries removed, or no medically documented ovarian failure). Women ≤50 years of age with amenorrhea will be considered to be of childbearing potential. These women must have a negative serum pregnancy test at screening and a negative urine pregnancy test on the Baseline/Day 1 visit prior to randomization. They must also agree to one of the following from 3 weeks prior to Baseline/Day 1 until 6 months after last dose of RBV:
      Complete abstinence from intercourse. Periodic abstinence from intercourse (e.g., calendar, ovulation, symptothermal, post-ovulation methods) is not permitted.

Or

Consistent and correct use of 1 of the following methods of birth control listed below in addition to a male partner who correctly uses a condom from the date of screening until 6 months after the last dose of RBV. Women of childbearing potential must not rely on hormone-containing contraceptives as a form of birth control during the study. Female subjects using a hormone-containing contraceptive prior to screening may continue their contraceptive regimen in addition to the study-specified methods of birth control.

intrauterine device (IUD) with a failure rate of <1% per year female barrier method: cervical cap or diaphragm with spermicidal agent tubal sterilization vasectomy in male partner 11. All male study participants must agree to consistently and correctly use a condom, while their female partner agrees to use either 1 of the non-hormonal methods of birth control listed above or a hormone-containing contraceptive listed below, from the date of screening until 7 months after their last dose of RBV:

implants of levonorgestrel injectable progesterone oral contraceptives (either combined or progesterone only)

contraceptive vaginal ring transdermal contraceptive patch

12. Male subjects must agree to refrain from sperm donation for at least 7 months after the last dose of RBV.
13. Subject must be of generally good health as determined by the Investigator.
14. Subject must be able to comply with the dosing instructions for study drug administration and able to complete the study schedule of assessments.

1.1.2. Inclusion Criteria for Part B

Subjects must meet all of the following inclusion criteria to be eligible for participation in this study.

1. Willing and able to provide written informed consent.
2. Male or female, age ≥18 years.
3. HCV genotype 4 at screening as determined by the Central Laboratory. Any non-definitive results will exclude the subject from study participation. Historical result from prior participation in this study is acceptable, if applicable.
4. Cohort 1 only: HCV RNA≥$10^4$ IU/mL at screening.
5. Cohort 1 only: HCV treatment naïve, defined as no prior exposure to any IFN, RBV, or other approved or experimental HCV-specific direct acting antiviral agent
6. BMI ≥18 kg/m$^2$ Absence of cirrhosis is defined as any one of the following:

a Liver biopsy within 2 years of Screening showing absence of cirrhosis b Fibroscan® with a result of ≤12.5 kPa within 6 months of Baseline/Day 1 c FibroTest® score of ≤0.48 AND APRI of ≤1 performed during Screening

In the absence of a definitive diagnosis of the presence or absence of cirrhosis by the above criteria, a liver biopsy is required. Liver biopsy results supersede the results obtained by Fibroscan or FibroTest®.

7. Screening ECG without clinically significant abnormalities.
8. Subjects must have the following laboratory parameters at screening:

ALT≤10× the upper limit of normal (ULN)

AST≤10×ULN

Hemoglobin≥12 g/dL for male, ≥11 g/dL for female subjects

Platelets>50,000 cells/mm$^3$

INR≤1.5×ULN unless subject has known hemophilia or is stable on an anticoagulant regimen affecting INR Albumin≥3 g/dL Direct bilirubin≤1.5×ULN HbA1c≤10%

Creatinine clearance (CLcr)≥60 mL/min, as calculated by the Cockcroft-Gault equation Subjects who received prior treatment in this study and who currently do not fulfill all of the above requirements may be enrolled in Part B Cohort 2 at the request of the Investigator and with the approval of the Medical Monitor or Study Director.

9. Subject has not been treated with any investigational drug or device within 28 days of the Baseline/Day 1 visit.
10. A female subject is eligible to enter the study if it is confirmed that she is:

d Not pregnant or nursing e Of non-childbearing potential (i.e., women who have had a hysterectomy, both ovaries removed or medically documented ovarian failure, or are postmenopausal women >50 years of age with cessation [for ≥12 months] of previously occurring menses), or f Of childbearing potential (i.e., women who have not had a hysterectomy, both ovaries removed, or no medically documented ovarian failure). Women ≤50 years of age with amenorrhea will be considered to be of childbearing potential. These women must have a negative serum pregnancy test at screening and a negative urine pregnancy test on the Baseline/Day 1 visit prior to randomization. They must also agree to one of the following from 3 weeks prior to Baseline/Day 1 until 30 days after the last dose of LDV/SOF or 6 months after last dose of RBV:

Complete abstinence from intercourse. Periodic abstinence from intercourse (e.g., calendar, ovulation, symptothermal, post-ovulation methods) is not permitted.

Or

Consistent and correct use of 1 of the following methods of birth control listed below in addition to a male partner who correctly uses a condom from the date of screening until 30 days after the last dose of LDV/SOF or 6 months after the last dose of RBV.

intrauterine device (IUD) with a failure rate of <1% per year female barrier method: cervical cap or diaphragm with spermicidal agent tubal sterilization vasectomy in male partner implants of levonorgestrel injectable progesterone oral contraceptives (either combined or progesterone only)

contraceptive vaginal ring transdermal contraceptive patch

11. All male study participants must agree to consistently and correctly use a condom from Baseline until 90 days after their last dose of LDV/SOF or 7 months after their last dose of RBV. If their female partner is of childbearing potential (as defined above), she must use 1 of the methods of birth control listed above from the date of screening until 90 days after their last dose of LDV/SOF or 7 months after their last dose of RBV.
12. Male subjects must agree to refrain from sperm donation for at least 7 months after the last dose of RBV or 90 days after their last dose of LDV/SOF, as applicable.
13. Subject must be of generally good health as determined by the Investigator.
14. Subject must be able to comply with the dosing instructions for study drug administration and able to complete the study schedule of assessments.

1.2. Exclusion Criteria
1.2.1. Exclusion Criteria for Part A

Subjects who meet any of the following exclusion criteria are not to be enrolled in this study.

1. For treatment-naïve subjects only: Prior exposure to IFN, RBV, or other approved or experimental direct-acting antiviral targeting the HCV.
2. For treatment-experienced subjects: prior exposure to a NS5a inhibitor, NS5b nucleotide inhibitor, or NS5b non-nucleotide inhibitor targeting the HCV
3. Pregnant or nursing female or male with pregnant female partner.
4. Chronic liver disease of a non-HCV etiology (e.g., hemochromatosis, Wilson's disease, α1 antitrypsin deficiency, cholangitis).
5. Infection with hepatitis B virus (HBV) or human immunodeficiency virus (HIV).
6. Contraindication to RBV therapy e.g., history of clinically significant hemoglobinopathy (sickle cell disease, thalassemia).
7. History of malignancy diagnosed or treated within 5 years (recent localized treatment of squamous or non-invasive basal cell skin cancers is permitted; cervical carcinoma in situ is allowed if appropriately treated prior to screening); subjects under evaluation for malignancy are not eligible.
8. Chronic use of systemically administered immunosuppressive agents (e.g., prednisone equivalent >10 mg/day).
9. Clinically-relevant drug or alcohol abuse within 12 months of screening. A positive drug screen will exclude subjects unless it can be explained by a prescribed medication; the diagnosis and prescription should be approved by the investigator.
10. History of solid organ transplantation.
11. Current or prior history of clinical hepatic decompensation (e.g., ascites, hemorrhage, hepatic encephalopathy, hepato-renal syndrome and hepato-pulmonary syndrome).
12. History of clinically-significant illness or any other major medical disorder that may interfere with subject treatment, assessment or compliance with the protocol.
13. History of a gastrointestinal disorder (or post-operative condition) that could interfere with the absorption of the study drug.
14. History of significant pulmonary disease, significant cardiac disease or *porphyria*.
15. Excessive alcohol ingestion, defined as □3 glasses/day (1 glass is equivalent to 284 mL beer, 125 mL wine, or 25 mL distilled spirits) for females and U 4 glasses/day for males.
16. History of difficulty with blood collection and/or poor venous access for the purposes of phlebotomy.
17. Donation or loss of more than 400 mL blood within 2 months prior to Baseline/Day 1.
18. Known hypersensitivity to RBV, the study investigational medicinal product, the metabolites, or formulation excipients.

1.2.2. Exclusion Criteria for Part B

Subjects who meet any of the following exclusion criteria are not to be enrolled in this study.

1. For treatment-naïve subjects only (Cohort 1): Prior exposure to IFN, RBV, or other approved or experimental direct-acting antiviral targeting the HCV.
2. Current or prior history of any of the following:
   a Clinical hepatic decompensation (i.e., ascites, encephalopathy or hemorrhage)
   b Clinically-significant illness (other than HCV) or any other major medical disorder that may interfere with subject treatment, assessment or compliance with the protocol, or, current evaluation for a potentially clinically significant illness (other than HCV)
   c Gastrointestinal disorder or post-operative condition that could interfere with the absorption of the study drug
   d Solid organ transplantation
   e Significant pulmonary disease, significant cardiac disease or *porphyria*
   f Psychiatric hospitalization, suicide attempt, and/or a period of disability as a result of their psychiatric illness within the last 5 years
      Subjects with psychiatric illness (without the prior mentioned conditions) that is well-controlled on a stable treatment regimen for at least 6 months prior to Baseline/Day 1 or that has not required medication in the last 12 months may be enrolled.
   g Any malignancy within the 5 years prior to screening, with the exception of specific cancers that are cured by surgical resection (basal cell skin cancer, etc.), or current evaluation for possible malignancy
   h Difficulty with blood collection and/or poor venous access for the purposes of phlebotomy
   i Significant drug allergy (such as anaphylaxis or hepatotoxicity)
3. Chronic liver disease of a non-HCV etiology (e.g., hemochromatosis, Wilson's disease, al antitrypsin deficiency, cholangitis)
4. Infection with hepatitis B virus (HBV) or human immunodeficiency virus (HIV)
5. Contraindication to RBV therapy, including significant history of clinically significant hemoglobinopathy (e.g., sickle cell disease, thalassemia)
6. In the judgment of the investigatory, any clinically-relevant drug or alcohol abuse within 12 months of screening that may interfere with subject treatment, assessment of compliance with the protocol
7. Pregnant or nursing females or male with pregnant female partner
8. Known hypersensitivity to RBV, SOF, or formulation excipients Study Procedures Table

TABLE 22

| | Screen | Baseline (Day 1)[a] | 1 | 2 | 4 | 6 | 8 | 10 | 12 | 16[b] | 20[b] | 24[b] | Unscheduled Visit/Early Termination |
|---|---|---|---|---|---|---|---|---|---|---|---|---|---|
| Screening and On-Treatment Study Visits for Part A | | | | | | | | | | | | | |
| Clinical Assessments | | | | | | | | | | | | | |
| Informed Consent | X | | | | | | | | | | | | |
| Determine Eligibility | X | X | | | | | | | | | | | |
| Medical History | X | | | | | | | | | | | | |
| Cirrhosis Determination | X | | | | | | | | | | | | |
| Physical Examination | X | X | | | | | | | X | | X | | X |
| Height | X | | | | | | | | | | | | |
| Weight | X | X | | | | | | | X | | | X | X |
| Vital Signs[c] | X | X | X | X | X | X | X | X | X | X | X | X | X |
| 12-Lead ECG | X | | | | | | | | | | | | |
| AEs and Concomitant Medications | X | X | X | X | X | X | X | X | X | X | X | X | X |
| Pregnancy Prevention Counseling | | X | | | | | | | X | | X | | X |
| Review of Study Medication Compliance | | | X | X | X | X | X | X | X | X | X | X | X |
| Study Drug Dispensing[d] | | X | | | X | | X | | X | X | X | | |
| Laboratory Assessments | | | | | | | | | | | | | |
| Hematology, Chemistry | X | X | X | X | X | X | X | X | X | X | X | X | X |
| Coagulation Tests[e] | X | X | | | | | | | X | | X | | X |
| HCV RNA | X | X | X | X | X | X | X | X | X | X | X | X | X |
| Viral Sequencing[f] | | X | X | X | X | X | X | X | X | X | X | X | X |
| Single PK | | X | X | X | X | X | X | X | X | X | X | X | X |
| Serum or Urine Pregnancy[g] | X | X | | | X | | X | | X[i] | X | X | X[i] | X[i] |
| Urinalysis | X | | | | | | | | | | | | |
| Urine Drug Screen | X | | | | | | | | | | | | |
| HCV Genotyping, IL28B | X | | | | | | | | | | | | |
| HCV, HIV, HBV Serology | X | | | | | | | | | | | | |
| HbA1c | X | | | | | | | | | | | | |
| GGT | X | | | | | | | | | | | | |
| TSH | X | | | | | | | | | | | | |
| Fibrotest ® | X | | | | | | | | | | | | |
| Liver Imaging[h] | X | | | | | | | | | | | | |

[a] Day 1 (baseline) assessments must be performed prior to randomization and dispensing/dosing.
[b] For subjects assigned to Arm 2 only (i.e., the 24-Week treatment regimen)
[c] Vital signs include blood pressure, pulse, respiratory rate and temperature
[d] The Randomization Schedule provided will provide direction on the specifics of each subject's study drug dispensing.
[e] PT, APTT, INR
[f] Plasma samples will be collected and stored for potential HCV sequencing and other virology studies
[g] Serum at Screen then urine test. If urine is positive confirm the test with serum b-HCG.
[h] Liver imaging
[i] Female subjects of childbearing potential should be provided with Urine Pregnancy Test Kits, instructed on their use and requested to continue to self-monitor for pregnancy for 6 months after their last dose of RBV. If required by regulations, additional pregnancy tests beyond 6 months may be added. The subject should be contacted every 4 weeks and asked to report results of the urine pregnancy tests. If a positive urine pregnancy test is reported, the subject should return to the clinic for a serum pregnancy test.

TABLE 23

Screening and On-Treatment Study Visits for Part B

| | Screen | Baseline/Day 1[a] | On-treatment Study Week 1 | 2 | 4 | 8 | 12[g] | Early Termination |
|---|---|---|---|---|---|---|---|---|
| Informed Consent | X | | | | | | | |
| Determine Eligibility | X | X | | | | | | |
| Medical History | X | | | | | | | |
| Physical Examination | X | X | | | | X[f] | X | X |
| Weight | X | X | | | | X[f] | X | X |
| Height | X | | | | | | | |
| Vital Signs[b] | X | X | X | X | X | X | X | X |
| 12-Lead ECG | X | | | | | | | |
| AEs | X | X | X | X | X | X | X | X |
| Concomitant Medications | X | X | X | X | X | X | X | X |
| Pregnancy Prevention Counseling | | X | | | | X[f] | X | X |
| Review of Study Medication Compliance | | | X | X | X | X | X | X |
| Study Drug Dispensing | | X | | | X | X[g] | | |
| Liver Imaging[c] | X | | | | | | | |
| Hematology, Chemistry | X | X | X | X | X | X | X | X |
| Coagulation Tests | X | X | | | | X[f] | X | X |
| HCV RNA | X | X | X | X | X | X | X | X |
| Serum or Urine Pregnancy | X | X | | | X | X | X | X |
| Urinalysis, HbA1c, TSH, Fibrotest, Serology, Urine Drug Screen | X | | | | | | | |
| HCV Genotype, IL28B[e] | X | | | | | | | |

[a]Baseline/Day 1 assessments must be performed prior to dosing
[b]Vital signs include resting blood pressure, pulse, respiratory rate and temperature
[c]Plasma samples will be collected and stored for potential HCV sequencing/phenotyping and other virology studies.
[d] For subjects being screened for Part B Cohort 1.
[e]Subjects receiving 8 weeks SOF FDC +/− RBC (Cohort 1 Groups 1 and 2)
[f]Subjects receiving 12 weeks SOF FDC +/− RBC (Cohort 1 Groups 3 and 4, Cohort 2)

TABLE 24

Post-Treatment Visits Following Primary Study

| | 4 Weeks Post-Treatment | 12 Weeks Post-Treatment[a] | 24 Weeks Post-Treatment[a] |
|---|---|---|---|
| Clinical Assessments | | | |
| Vital Signs[b] | X | X | X |
| Weight | | X | X |
| AEs | X | X[e] | X[e] |
| Concomitant Medications | X | | |
| Laboratory Assessments | | | |
| Hematology, Chemistry | X | X | |
| HCV RNA | X | X | X |
| Viral Sequencing[c] | X | X | X |
| Urine Pregnancy Test[d] | X | X | X |
| Pregnancy Prevention Counseling | X | X | X |

[a]Subjects with HCV RNA < LLOQ will continue to 12 Week and 24 Week Post treatment visits unless confirmed viral relapse occurs at which time subjects will be early terminated from the study.
[b]Vital signs include blood pressure, pulse, respiratory rate and temperature
[c]Plasma samples will be collected and stored for potential HCV sequencing and other virology studies
[d]Female subjects of childbearing potential should be provided with Urine Pregnancy Test Kits, instructed on their use and requested to continue to self-monitor for pregnancy for 6 months after their last dose of RBV. If required by regulations, additional pregnancy tests beyond 6 months may be added. The subject should be contacted every 4 weeks and asked to report results of the urine pregnancy tests. If a positive urine pregnancy test is reported, the subject should return to the clinic for a serum pregnancy test.
[e]All SAEs, including deaths, regardless of cause or relationship, must be reported after patient signs the informed consent through the end of the study

EXAMPLE 71

Effect on Viral Load

Our novel single tablet (Catvira) composition produced a 6-week post-treatment sustained virological response (SVR12) rate of 100% for both treatment-naive patients and prior non-responders, without affecting hemoglobin content as compared to separate multiple tablets of Ribavirin and Sofosbuvir. In contrast to the standard of care Ribavirin and Sofosbuvir, our Catvira single administration tablets did not elicit reported side effects with the standard of care including anemia, anorexia, coughing, and leg pain.

HCV/RNA PCR Quantitation During Treatment—CATVIRA

TABLE 25

Treatment Naive Table: HCV PCR: Fold changes from base line of PCR over 12 weeks

| Treatment | Sofosbuvir + Ribavirin | CATVIRA Tablet |
|---|---|---|
| Base line | 1 | 1 |
| 1 week | 0.000178 | 0.0001421 |
| 2 weeks | 3.64E−05 | 4.65E−06 |
| 4 weeks | 7.54E−06 | 0 |
| 8 weeks | 0 | 0 |
| 12 weeks | 0 | 0 |

HCV/RNA PCR Quantitation During Treatment—CATVIRA in Treatment Experienced

TABLE 26

HCV PCR: Fold changes from base line of PCR over 24 weeks

| Time | SOFOSBUVIR + Ribavirin | Catvira |
|---|---|---|
| 1 week | 0.000144 | 0.000119* |
| 2 weeks | 3.39E−05 | 2.05E−05* |
| 4 weeks | 1.23E−05 | 1.26E−06* |
| 8 weeks | 6.49E−07 | 0 * |
| 12 weeks | 0 | 0 |
| 16 weeks | 0 | 0 |
| 20 weeks | 0 | 0 |
| 24 weeks | 0 | 0 |

Significant trend for faster lowering of HCV viral load in the EHCV (Catvira vs. SOF + Rib),
*P < 0.05

EXAMPLE 72

Effect on Red Blood Cell Count and Hemoglobin (Anemia)

Hemoglobin CATVIRA Versus Standard of Care

Experienced

TABLE 27

Fold changes in RBCs in Catvira arm versus standard of Care

| Time | SOFOSBUVIR + Ribavirin | CATVIRA |
|---|---|---|
| Base line | 1 | 1 |
| 1 week | 0.980397 | 0.98983 |

TABLE 27-continued

Fold changes in RBCs in Catvira arm versus standard of Care

| Time | SOFOSBUVIR + Ribavirin | CATVIRA |
|---|---|---|
| 2 weeks | 0.925334 | 0.948911 |
| 4 weeks | 0.872578* | 0.917349 |
| 8 weeks | 0.865496* | 0.916996 |
| 12 weeks | 0.872737* | 0.920706 |
| 16 weeks | 0.847672* | 0.919116 |
| 20 weeks | 0.860881* | 0.908163 |
| 24 weeks | 0.853719* | 0.916247 |

Statistically significant reductions (*P < 0.05) as compared to baseline

TABLE 28

Fold changes in Hemoglobin in Catvira arm versus standard of Care

| Time | SOFOSBUVIR + Ribavirin | Catvira |
|---|---|---|
| Base line | 1 | 1 |
| 1 week | 0.981609 | 0.991444 |
| 2 weeks | 0.921834 | 0.951872 |
| 4 weeks | 0.869425* | 0.922853 |
| 8 weeks | 0.868858* | 0.925443 |
| 12 weeks | 0.870275* | 0.923824 |
| 16 weeks | 0.869142* | 0.927062 |
| 20 weeks | 0.868008* | 0.927062 |
| 24 weeks | 0.85866* | 0.936946 |

Statistically significant reductions (*P < 0.05) as compared to baseline

What is claimed is:

1. A composition, comprising:
an anti-viral agent comprising ribavirin;
a polymerase inhibitor comprising sofosbuvir; and
one or more anti-fibrotic agents and/or anti-hemolytic agents comprising one or more Polyphenols, wherein the one or more Polyphenols comprise epigallocatech gallate (EGCG).

2. The composition of claim 1, further comprising:
one or more non-anticoagulant Glycosaminoglycans (GAGS).

3. The composition of claim 2, wherein the one or more non-anticoagulant Glycosaminoglycans comprise one or more sulfated oligosaccharide non-anticoagulant Glycosaminoglycans.

4. The composition of claim 1, further comprising daclatisvir.

5. The composition of claim 1, further comprising ledipasvir.

6. The composition of claim 1, anti-viral agent further comprises taribavirin.

7. The composition of claim 1, further comprising a protease inhibitor.

8. The composition of claim 7, wherein the protease inhibitor comprises boceprevir, telaprevir, or simeprevir.

9. The composition of claim 1, further comprising sulfated Glycosaminoglycans.

10. The composition of claim 1, wherein the one or more Polyphenols further comprise at least one Polyphenol selected from the group consisting of Resveratrol, Catechin, Ellagic acid, punicagilin, and combinations thereof.

11. The composition of claim 1, further comprising one or more Thiols.

12. The composition of claim 11, wherein the one or more Thiols are selected from the group consisting of allin, N-acetyl cysteine, Sulforaphane, glutathione, and combinations thereof.

13. The composition of claim 1, wherein the one or more Polyphenols are derived from natural sources.

14. The composition of claim 1, wherein the composition comprises a Nanoformulation that includes the anti-viral agent, the polymerase inhibitor, and the one or more anti-fibrotic and/or anti-hemolytic agents.

15. The composition of claim 14, wherein the Nanoformulation includes Galactosylated Solid Lipid Nanoparticles (SLN), with targeting to hepatitis C virus (HCV) using $\alpha v \beta 3$ integrin ligand and/or the liver using Glycyrrhetinic or Lactobionic Acids.

16. The composition of claim 14, wherein the Nanoformulation includes Chitosan cross-linked with alginate or Chitosan cross-linked with Hyaluronic acid, with targeting to hepatitis C virus (HCV) and/or the liver.

17. A method of treating a hepatitis C virus (HCV) infection in a subject who is human being, said method comprising:
   administering to the subject a therapeutic dose of the composition of claim 1 to treat the subject for the HCV infection.

18. The method of claim 17, wherein the composition is in a tablet, and wherein said administering comprises administering the tablet to the subject orally.

* * * * *